US011141473B2

(12) United States Patent
Kania et al.

(10) Patent No.: US 11,141,473 B2
(45) Date of Patent: Oct. 12, 2021

(54) ***STAPHYLOCOCCUS PSEUDINTERMEDIUS* VIRULENCE FACTOR COMPOSITIONS**

(71) Applicant: UNIVERSITY OF TENNESSEE RESEARCH FOUNDATION, Knoxville, TN (US)

(72) Inventors: Stephen A. Kania, Powell, TN (US); David Bemis, Maryville, TN (US); Mohamed A. Abouelkhair, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 16/636,682

(22) PCT Filed: Aug. 10, 2018

(86) PCT No.: PCT/US2018/046281

§ 371 (c)(1),
(2) Date: Feb. 5, 2020

(87) PCT Pub. No.: WO2019/033007

PCT Pub. Date: Feb. 14, 2019

(65) Prior Publication Data

US 2020/0246446 A1 Aug. 6, 2020

Related U.S. Application Data

(60) Provisional application No. 62/543,676, filed on Aug. 10, 2017.

(51) Int. Cl.

| | |
|---|---|
| ***A61K 39/09*** | (2006.01) |
| ***A61K 39/085*** | (2006.01) |
| ***A61K 39/02*** | (2006.01) |
| ***A61K 39/116*** | (2006.01) |
| ***A61K 45/00*** | (2006.01) |
| ***A61K 47/00*** | (2006.01) |
| ***A61P 31/04*** | (2006.01) |
| *A61K 39/00* | (2006.01) |
| *A61K 39/39* | (2006.01) |
| *C07K 14/315* | (2006.01) |

(52) U.S. Cl.

CPC ............ *A61K 39/085* (2013.01); *A61P 31/04* (2018.01); *A61K 39/00* (2013.01); *A61K 39/116* (2013.01); *A61K 39/39* (2013.01); *A61K 2039/522* (2013.01); *A61K 2039/5254* (2013.01); *A61K 2039/552* (2013.01); *A61K 2039/575* (2013.01); *C07K 14/315* (2013.01)

(58) Field of Classification Search

CPC .................................................... A61K 39/085

See application file for complete search history.

(56) References Cited

FOREIGN PATENT DOCUMENTS

WO 2011/045573 A2 4/2011

OTHER PUBLICATIONS

Cleveland Clinic, https://my.clevelandclinic.org/health/diseases/21165-staph-infection-staphylococcus-infection#prevention; accessed on Feb. 10, 2021 (Year: 2021).*

International Search Report and Written Opinion for PCT/US2018/046281 dated Apr. 29, 2019.

NCBI, GenBank accession No. WP_065520714.1, Jul. 21, 2016. Available via URL https://www.ncbi.nlm.nih.gov/protein/WP_065520714.1/.

NCBI, GenBank accession No. WP_020220128.1, Jun. 30, 2013. Available via URL https://www.ncbi.nlm.nih.gov/protein/WP_020220128.1/.

Ruzauskas, M. et al., 'Characterization of *Staphylococcus pseudintermedius* isolated from diseased dogs in Lithuania', Pol. J. Vet. Sci., 2016, vol. 19, No. 1, pp. 7-14.

Garbacz, K. et al., 'Pathogenicity potential of *Staphylococcus pseudintermedius* strains isolated from canine carriers and from dogs with infection signs', Virulence, Jan. 17, 2013, vol. 4, No. 3, pp. 255-259.

* cited by examiner

*Primary Examiner* — Gary B Nickol
*Assistant Examiner* — Lakia J Jackson-Tongue
(74) *Attorney, Agent, or Firm* — Patrick M. Torre

(57) ABSTRACT

A multivalent immunogenic composition is provided, including one or more recombinant proteins selected from the group consisting of a recombinant attenuated *Staphylococcus pseudintermedius* Protein A (SEQ ID NO:2), a recombinant attenuated *Staphylococcus pseudintermedius* Leukotoxin S (SEQ ID NO:4), a recombinant attenuated *Staphylococcus pseudintermedius* Nucleotidase adenosine synthase protein (AdsA) (SEQ ID NO:6), a recombinant attenuated *Staphylococcus pseudintermedius* coagulase (SEQ ID NO:8), a recombinant attenuated *Staphylococcus pseudintermedius* Leukotoxin F (SEQ ID NO: 10), and a recombinant attenuated *Staphylococcus pseudintermedius* exotoxin 15 (SEQ ID NO: 12). Synthetic genes expressing the attenuated recombinant proteins and optimized for expression in *E. coli* are provided. Vaccines and therapeutic compositions comprising the one or more recombinant proteins are provided.

13 Claims, 39 Drawing Sheets

Specification includes a Sequence Listing.

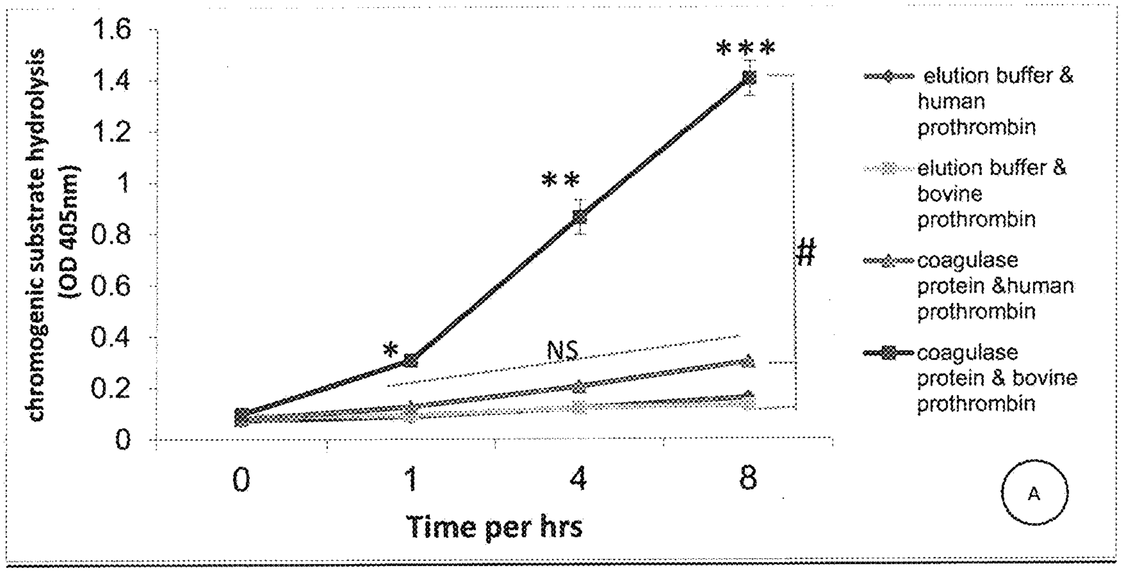
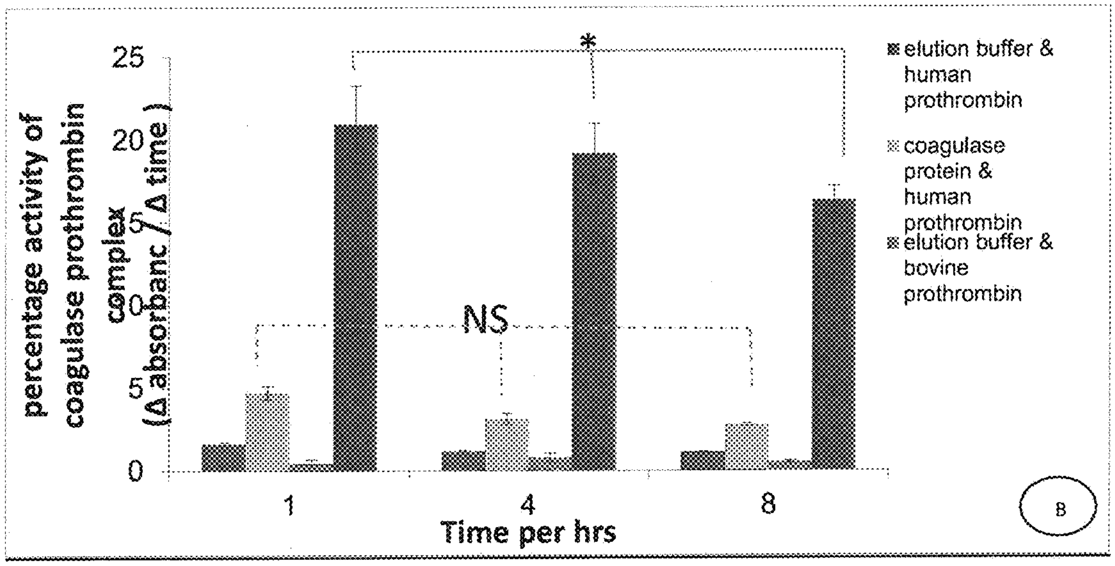
Fig. 5

D.

a
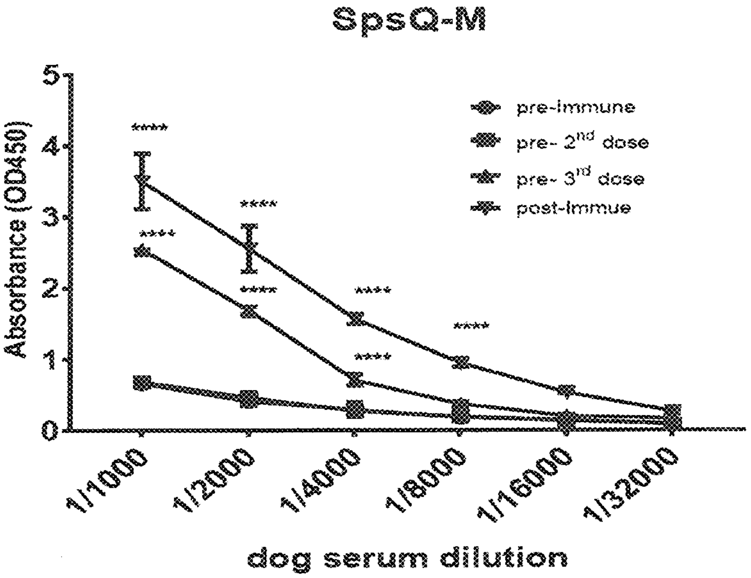
b
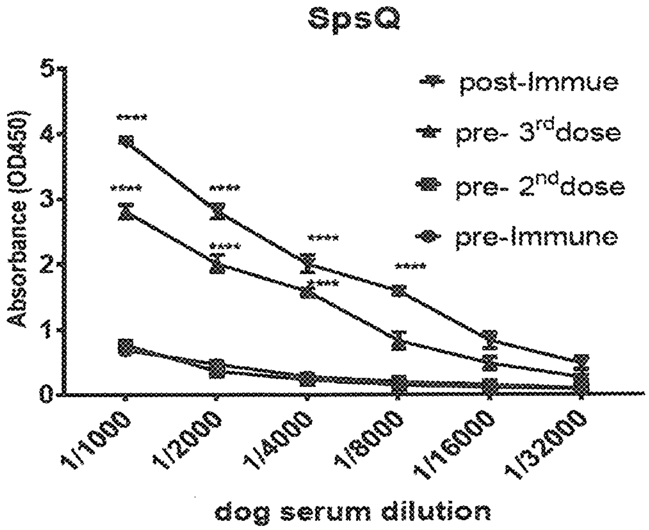
Fig. 12

A, Schematic diagram of the *S. pseudintermedius* 08-1661 SpAdsa

B, binding site prediction

Predicted Binding Site

| Residue | Amino acid | contact | av distance |
|---|---|---|---|
| 154 | ASP | 17 | 0.21 |
| 156 | HIS | 20 | 0.22 |
| 189 | ASP | 26 | 0.19 |
| 221 | ASN | 10 | 0.07 |
| 318 | HIS | 13 | 0.13 |
| 354 | HIS | 15 | 0.16 |
| 356 | HIS | 20 | 0.07 |

C, 3D model of *S. pseudintermedius* SpAdsa protein with amino acid substitutions

D

E

```
S. aureus LUKF-PV   MKIKNIVKSSVATSITFIMLSNTVDAAQHITPVSEKKVDDKITLYKTTATSDSDKLKISQ
S. aureus LUKQ      MKVKKIVKSSIATSIALIMLSNTVDAAQYITPVNEKKVDDKITLYKTTATSINDKLNMSQ
   Canine LukF      MKISKVIKAATATSVALMLFSNPVYAANQITPVSEKKVDDKITLYKTTATADSDKLNISQ

S. aureus LUKF-PV   ILTFNFIKDKSYDKDTLILKAAGNIYSGYTQPTSDSKINSQFYWGAKYNVFVSSESKDSV
S. aureus LUKQ      ILTFNFVKDKSYDKDTLVLKASGNINSGYTKPTSDNKISSQFYWGAKYNVFISSEGNDSV
   Canine LukF      LLTFNFIKDKSYIKDTLVLKAAGNINSGYKSPNPHDYIYSSFYWGAKYNVSISAESKSAV

S. aureus LUKF-PV   NIVDYAPKNQNEEFQVQQTLGYSYGGDINIINGLTGGLNGSKSFSETINYKQESYRTTID
S. aureus LUKQ      NVVDYAPKNQNEEFQVQQTLGYSYGGDINISNGLSGKLNGSESFSETISYKQESYRTTID
   Canine LukF      NVVDYAPKNQNEEFQVQNTLGYSFGGDISISKGLSGGLNGSESFSETINYKQESYRTTID

S. aureus LUKF-PV   RKINHKLIGWGVEAHKIMNNGWGPYGRDSSDSLYGNELFLGGRQSSSNANQNFLPTHQMP
S. aureus LUKQ      RKTDYKTIGWGVEAHKIMNNGWGPYGRDSYDSIYGNELFLGSRQSSSNANQNFLSTHQMP
   Canine LukF      KHTINKTIGWGVEAHKIMNAGWGPYGRDSFHDLYGNELFLGGRQSKLNAGQNFLPTSQMP

S. aureus LUKF-PV   ILARGNFNPEFISVLSHKQKDVKKSKIKVTYQRQMDRYENFWNNLHWIGYNIKNQKRATH
S. aureus LUKQ      ILARGNFNPEFIGVPSHKQNKNKKSKIKVTYQREMDEYVNYWNGIHWIGFNHKAQNIATH
   Canine LukF      LLARGNFNPEFLSVLSHKPNGAKTSKIKVTYQREMDEYTNYWNGFHWMGTNYKNQNNATF

S. aureus LUKF-PV   TSIYEIDWEKHTVKLVASQSSE----
S. aureus LUKQ      TSIYEIDWEKNTVKLIDKQAYEKVPS
   Canine LukF      TSFYEIDWQQHTVKLIKTHSIEKNPS
```

Fig. 19

(a)
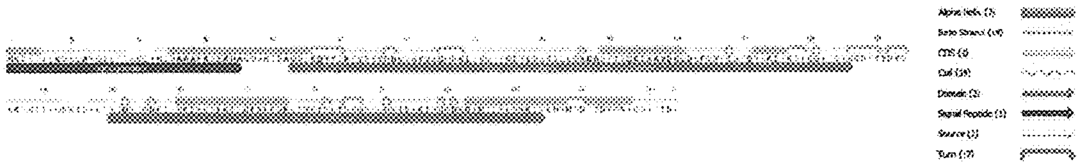
(b)
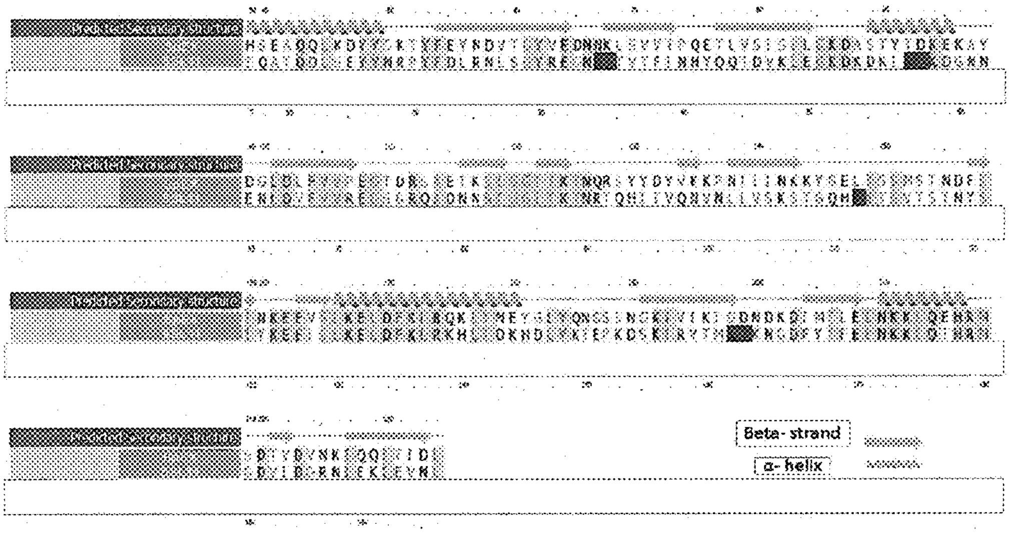
(c)
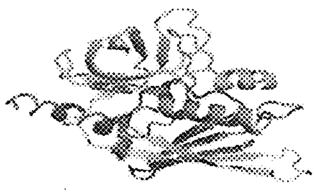
Fig. 24

(a)
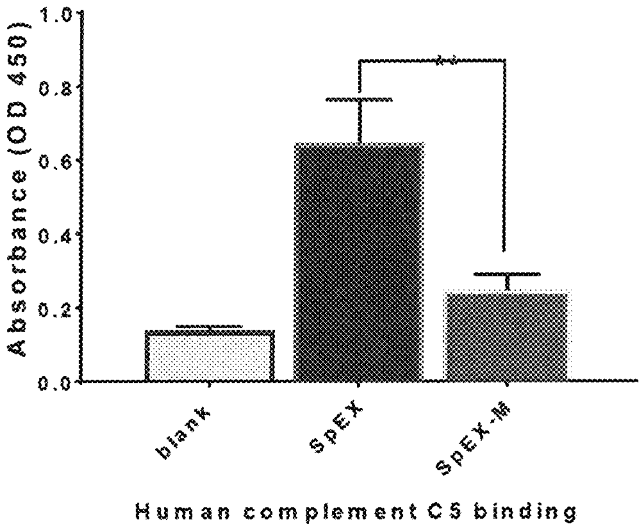
(b)
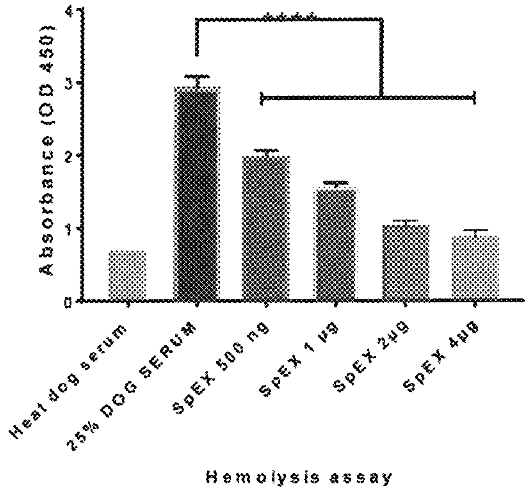
Fig. 25

*S. pseudintermedius* attenuated chimeric protein (SEQ ID NO: 14)

TAAQITAGIALHQSNLNTAVPQTKHEATFEVPQGRNTQTSATANKEQATETVDAPKANGQVQSEQVATPGVQQTHS
MAQQSETPQPVAEETETITGSMVKNKLLAATLSISLVLPLITPYSEEAKAANTIEEIGEGAQIIKRTEDVSSRKWGVFQNIQ
FDFVKDPKYNKDALIIKMQGFIKSRTSFTDVKGKGYESTKRMLWPFQYNIALKTNDPNVSLINYLPANKIESIDVSQTLGY
NVGGNFQSAPLLGGKGAFNYSKKISYTQKNYISEVAQQNSKNIRWEVKANSFNTENGQVSAYDRHLFVRSPIGPNARD
FFVPNDELPPLIQSGFNPAFIATVSHEKDKGDTSEFEIAYGRNLDITYATFFPRTGIFAERRHNALMNRNLVTKYEVNWKT
HEIKVKGHNAAKKAQPEATSIDRASHETAATTHTILHTNAIAGRMVEEKDRVLGYDAMTAGNAEFAFGYDQLKKLEG
MLNFPIVSSNVYKHEDPSFAEEGDNNAEAKKNAFSEVVKLPNLSEEQRNGFIQSLKAAPSTSQDVLNEAKKLNDSQEGS
QPAPDYSDEKKNAFYEIQSLKAAPSVSANILVEAKNMNVNQTPTQPAPSFDEAKKNAFYEIVNQAKPDYNEAKKNAFY
EILHLPN

Purple= Canine T cell epitope
Red = Coagulase
Blue= Attenuated LukS
Green= Attenuated Nucleotidase
Black=Attenuated Protein A

FIG. 32

*STAPHYLOCOCCUS PSEUDINTERMEDIUS* VIRULENCE FACTOR COMPOSITIONS

This application is the national stage of international patent application no. PCT/US2018/046281 filed on Aug. 10, 2018 which in turn claims the benefit of priority in U.S. provisional patent application Ser. No. 62/543,676 filed on Aug. 10, 2017, the entire disclosures of which are incorporated herein by reference in their entirety.

REFERENCE TO SEQUENCE LISTING SUBMITTED ELECTRONICALLY

A sequence listing electronically submitted with the present application as an ASCII text file named 1101-016PCTSequenceListing_ST25.txt, created on Aug. 10, 2018 and having a size of 40,000 bytes, is incorporated herein by reference in its entirety.

TECHNICAL FIELD

The present disclosure relates to therapeutic compositions, vaccines and immunogenic compositions comprising one or more immunogenic, attenuated, and/or non-cytotoxic proteins derived from *Staphylococcus pseudintermedius*. The compositions comprise recombinant attenuated proteins expressed from synthetic genes altered to produce the attenuated proteins. In particular, the disclosure relates to vaccines and immunogenic compositions comprising one or more natural or recombinant immunogenic, attenuated, non-cytotoxic *Staphylococcus pseudintermedius* proteins capable of inducing the production of antibodies reactive with *S. pseudintermedius* proteins naturally secreted and/or displayed on the bacterial surface and involved in host immune dysfunction and/or evasion. The disclosure further relates to therapeutic compositions comprising one or more natural or recombinant immunogenic, attenuated, non-cytotoxic *Staphylococcus pseudintermedius* proteins capable of improving the host immune response independent of production of antibody.

BACKGROUND

*Staphylococcus pseudintermedius* is the primary cause of canine pyoderma (skin infection). Pyoderma is the most common canine dermatologic disease and the organism is also associated with urinary tract infections, wound and surgical site infections, external ear otitis, abscess formation, mastitis and endocarditis. As many as 30-40% of the *S. pseudintermedius* isolates tested in clinical laboratories in some geographical regions are methicillin-resistant (MRSP). These bacteria are resistant to all β-lactam antibiotics. The vast majority of MRSP are also resistant to other clinically useful antibiotics and an increasing number of MRSP are resistant to all antimicrobials available to veterinarians. Accordingly, there is a need for immunogenic compositions capable of inducing antibodies to, and/or a protective immune response to *S. pseudintermedius*.

Development of vaccines to control staphylococcal infections is a high priority, however there are no licensed *S. pseudintermedius* vaccines. This is likely due to a lack of information about *S. pseudintermedius* protein functions, surface accessibility and epitope conservation. Information about other species of bacteria, especially staphylococci, is useful in the development of a *S. pseudintermedius* vaccine, however, this species is unique with regard to its disease presentation, genetic structure and composition, host range, and the virulence proteins it produces. Whole bacterial staphylococcal vaccines have not been efficacious. With an estimated greater than 2,000 different proteins produced by each bacterium, it is essential to identify and direct the immune response against the most important antigen targets. However, many of these proteins are potentially harmful to animals and must be attenuated to make them safe without eliminating epitopes that induce a protective immune response. Effective staphylococcal defenses are rooted in the ability of the bacteria to neutralize and/or destroy important components of their host's defenses.

There accordingly remains a need in the art for novel immunogenic compositions suitable for preparing *S. pseudintermedius* vaccines and therapeutic compositions. To meet this identified need in the art, conserved *S. pseudintermedius* cell surface-bound and secreted immunogenic proteins have been identified and attenuated and/or non-cytotoxic immunogenic recombinant proteins produced. The attenuated and/or non-cytotoxic immunogenic recombinant *S. pseudintermedius* cell surface-bound and cell-expressed proteins are suitable for vaccine development, including multivalent vaccines, and for manufacture of therapeutic compositions.

SUMMARY

In one aspect of the present disclosure, a multivalent immunogenic therapeutic composition is provided, comprising one or more recombinant proteins selected from the group consisting of an attenuated immunoevasive *Staphylococcus pseudintermedius* Protein A (SEQ ID NO:2) and an attenuated immunoevasive *Staphylococcus pseudintermedius* Leukotoxin S (SEQ ID NO:4) and optionally, one or more suitable pharmaceutical or veterinary excipients and carriers. The composition may further comprise one or more of an attenuated immunoevasive *Staphylococcus pseudintermedius* Nucleotidase adenosine synthase protein (AdsA) (SEQ ID NO:6), an attenuated immunoevasive *Staphylococcus pseudintermedius* coagulase (SEQ ID NO:8), an attenuated immunoevasive *Staphylococcus pseudintermedius* Leukotoxin F (SEQ ID NO:10), and an attenuated immunoevasive *Staphylococcus pseudintermedius* exotoxin 15 (SEQ ID NO:12).

In an embodiment, the multivalent immunogenic therapeutic composition consists essentially of a recombinant attenuated immunoevasive *Staphylococcus pseudintermedius* Protein A (SEQ ID NO:2), a recombinant attenuated immunoevasive *Staphylococcus pseudintermedius* Leukotoxin S (SEQ ID NO:4), a recombinant attenuated immunoevasive *Staphylococcus pseudintermedius* Nucleotidase adenosine synthase protein (AdsA) (SEQ ID NO:6), a recombinant attenuated immunoevasive *Staphylococcus pseudintermedius* coagulase (SEQ ID NO:8), a recombinant attenuated immunoevasive *Staphylococcus pseudintermedius* Leukotoxin F (SEQ ID NO:10), and a recombinant attenuated immunoevasive *Staphylococcus pseudintermedius* exotoxin 15 (SEQ ID NO:12), and optionally, one or more suitable pharmaceutical or veterinary excipients and carriers. In another embodiment, the multivalent immunogenic therapeutic composition consists essentially of a recombinant attenuated immunoevasive *Staphylococcus pseudintermedius* Protein A (SEQ ID NO:2), a recombinant attenuated immunoevasive *Staphylococcus pseudintermedius* Leukotoxin S (SEQ ID NO:4), a recombinant attenuated immunoevasive *Staphylococcus pseudintermedius* Nucleotidase adenosine synthase protein (AdsA) (SEQ ID NO:6), a recombinant attenuated immunoevasive *Staphylococcus pseudintermedius* coagulase (SEQ ID NO:8), a recombinant attenuated immunoevasive *Staphylococcus pseudintermedius* Leukotoxin F (SEQ ID NO:10), and a recombinant attenuated immunoevasive *Staphylococcus pseudintermedius* exotoxin 15 (SEQ ID NO:12); and optionally, one or more suitable pharmaceutical or veterinary excipients and carriers.

In another aspect of the disclosure, a vaccine composition is provided comprising one or more recombinant proteins selected from the group consisting of a recombinant attenuated *Staphylococcus pseudintermedius* Protein A (SEQ ID NO:2) and a recombinant attenuated *Staphylococcus pseudintermedius* Leukotoxin S (SEQ ID NO:4); and one or more of a suitable pharmaceutical or veterinary adjuvant, a suitable pharmaceutical or veterinary excipient, and a suitable pharmaceutical or veterinary carrier. The vaccine composition may further comprise one or more of an attenuated immunoevasive *Staphylococcus pseudintermedius* Nucleotidase adenosine synthase protein (AdsA) (SEQ ID NO:6), an attenuated immunoevasive *Staphylococcus pseudintermedius* coagulase (SEQ ID NO:8), an attenuated immunoevasive *Staphylococcus pseudintermedius* Leukotoxin F (SEQ ID NO:10), and an attenuated immunoevasive *Staphylococcus pseudintermedius* exotoxin 15 (SEQ ID NO:12).

In an embodiment, the vaccine composition consists essentially of a recombinant attenuated immunoevasive *Staphylococcus pseudintermedius* Protein A (SEQ ID NO:2), a recombinant attenuated immunoevasive *Staphylococcus pseudintermedius* Leukotoxin S (SEQ ID NO:4), a recombinant attenuated immunoevasive *Staphylococcus pseudintermedius* Nucleotidase adenosine synthase protein (AdsA) (SEQ ID NO:6), a recombinant attenuated immunoevasive *Staphylococcus pseudintermedius* coagulase (SEQ ID NO:8), a recombinant attenuated immunoevasive *Staphylococcus pseudintermedius* Leukotoxin F (SEQ ID NO:10), and a recombinant attenuated immunoevasive *Staphylococcus pseudintermedius* exotoxin 15 (SEQ ID NO:12), and optionally, one or more suitable pharmaceutical or veterinary excipients and carriers. In another embodiment, the vaccine composition consists essentially of a recombinant attenuated immunoevasive *Staphylococcus pseudintermedius* Protein A (SEQ ID NO:2), a recombinant attenuated immunoevasive *Staphylococcus pseudintermedius* Leukotoxin S (SEQ ID NO:4), a recombinant attenuated immunoevasive *Staphylococcus pseudintermedius* Nucleotidase adenosine synthase protein (AdsA) (SEQ ID NO:6), a recombinant attenuated immunoevasive *Staphylococcus pseudintermedius* coagulase (SEQ ID NO:8), a recombinant attenuated immunoevasive *Staphylococcus pseudintermedius* Leukotoxin F (SEQ ID NO:10), and a recombinant attenuated immunoevasive *Staphylococcus pseudintermedius* exotoxin 15 (SEQ ID NO:12); and optionally, one or more suitable pharmaceutical or veterinary excipients and carriers.

In another aspect of the disclosure, a multivalent chimeric protein is provided comprising one or more recombinant attenuated immunoevasive proteins from *Staphylococcus pseudintermedius* cell surface-bound and/or secreted proteins, and comprising the sequence set forth as SEQ ID NO: 14.

In another aspect of the disclosure, a *Staphylococcus pseudintermedius* Protein A synthetic gene (SEQ ID NO:1) codon optimized for expressing a recombinant attenuated immunoevasive Protein A in *Escherichia coli* is provided.

In another aspect of the disclosure, a *Staphylococcus pseudintermedius* Leukotoxin S synthetic gene (SEQ ID NO:3) codon optimized for expressing a recombinant attenuated immunoevasive leukotoxin in *Escherichia coli* is provided.

In another aspect of the disclosure, a *Staphylococcus pseudintermedius* Nucleotidase adenosine synthase protein (AdsA) synthetic gene (SEQ ID NO:5) codon optimized for expressing a recombinant attenuated immunoevasive Nucleotidase ADsA in *Escherichia coli* is provided.

In another aspect of the disclosure, a *Staphylococcus pseudintermedius* coagulase synthetic gene (SEQ ID NO: 7) codon optimized for expressing a recombinant attenuated immunoevasive coagulase in *Escherichia coli* is provided.

In another aspect of the disclosure, a *Staphylococcus pseudintermedius* Leukotoxin F synthetic gene (SEQ ID NO: 9) codon optimized for expressing a recombinant attenuated immunoevasive gamma-hemolysin in *Escherichia coli* is provided.

In another aspect of the disclosure, a *Staphylococcus pseudintermedius* exotoxin 15 synthetic gene (SEQ ID NO: 11) codon optimized for expressing a recombinant attenuated immunoevasive exotoxin 15 in *Escherichia coli* is provided.

In the following description, there are shown and described embodiments of the disclosed recombinant attenuated *S. pseudintermedius* cell-surface and secreted proteins, and multivalent immunogenic compositions and vaccines including same. As it should be realized, the disclosed proteins, multivalent immunogenic compositions, and vaccines are capable of other, different embodiments and their several details are capable of modification in various, obvious aspects all without departing from the devices and methods set forth and described in the following claims. Accordingly, the drawings and descriptions should be regarded as illustrative in nature and not as restrictive.

BRIEF DESCRIPTION OF THE DRAWINGS

The accompanying drawing figures incorporated herein and forming a part of the specification, illustrate several aspects of the disclosed recombinant attenuated *S. pseudintermedius* cell-surface and secreted proteins, and multivalent immunogenic compositions and vaccines, and together with the description serve to explain certain principles thereof. In the drawings:

FIG. 5: Staphylococcus pseudintermedius coa recombinant protein displays clotting activity. A. Purified active Coa was incubated in a 1:1 molar ratio with human and bovine prothrombin. Enzymatic activity of these complexes was assessed by monitoring the rate of chromogenic substrate hydrolysis. Time 0 showed no significant differences between treatments (p=0.163) and all other time points show significant differences between treatments (p<0.001). The absorbance at time 1, 4, 8 h for coagulase interaction with the Human prothrombin, and elution buffer with bovine prothrombin are all significantly lower (#p<0.001) than Coagulase interaction with bovine prothrombin with no other significant differences. The absorbance at all times for coagulase interaction with the bovine prothrombin significantly differed from time 0 with *p=0.037, p=0.028, and *p=0.008 for time 1, 4, 8 hr respectively. There is no significant difference between coagulase and elution buffer interaction with Human prothrombin (p=0.098, p=0.741, and p=0.125) at time 1, 4, 8 h respectively. All times significantly differed from one another which indicates that absorbance significantly increased over time (8 hr>4 hr>1 hr). The absorbance at time 8 hr is significantly higher than time 4 hr and time 1 hr (p=0.013, p=0.008 respectively) and the absorbance at time 4 hr is significantly higher than time 1 hr (p=0.026). B. The percentage of Coa prothrombin complex activity was interpreted to the change in the rate of S-2238 hydrolysis (Δabsorbance) over time (Δtime). The interaction of treatment by time was not significant (p=0.056). There was a significant main effect of treatment (p<0.001) and a marginally significant main effect for time (p=0.021). Overall, coagulase bovine prothrombin complex percentage activity was significantly higher than coagulase Human prothrombin complex and elution buffer with bovine prothrombin (*p<0.001). There was no significant difference between coagulase and elution buffer interaction with Human prothrombin (p=0.522). All times did not significantly differ from one another which indicates that percentage activity is not significantly decreased over time (8 hr<4 hr<1 hr). Time 8 hr is not significantly lower than time 4 hr and time 1 hr (p=0.193, p=0.082 respectively) and at time 4 hr is not significantly lower than time 1 hr (p=0.103).

FIG. 12: Dogs injected with SpsQ-M developed specific IgG reactive with recombinant wildtype and mutant protein A. A) specific antibodies against SpsQ-M. B) specific antibodies against SpsQ.

FIG. 19: Multiple sequence alignment of LukF-PV, LukR and LukQ.

FIG. 24: *S. pseudintermedius* exotoxin 15 (SpEX) characteristics. a) SpEX of *S. pseudintermedius* harbors an N-terminal signal peptide (green arrow) from position 1-35, oligonucleotide/oligosaccharide binding (OB-fold) domain (orange arrow) in residues 43-126 and C-terminal β grasp domain in residues 150-217 (orange arrow); b) a pairwise sequence alignment of *S. pseudintermedius* SpEx and *S. aureus* SSL11 showing that both share the same domain structure; c) SpEX 3D model.

FIG. 25: SpEX interferes with complement function. A. The HRP-conjugated anti-6×his tag monoclonal antibody was used at a dilution of 1/1000 to detect bound recombinant SpEX to human C5. SpEX was significantly bound to human C5 compared to SpEX-M at the same dilution (500 ng/ml with P<0.0013 **). The values represent averages from three independent experiments. (*P<0.05 was considered significant. B. SpEX caused inhibition of hemolysis at a concentration dependent manner. Starting at concentration of 500 ng, we found that SpEX significantly reduced the hemolysis of sensitized bovine erythrocytes compared to positive control with P<0.0001****. SpEX at concentration of 4 μg showed no significant difference in hemolysis with the negative control. The values represent averages from three independent experiments. (*P<0.05 was considered significant).

FIG. 32: Sequence of a recombinant attenuated *S. pseudintermedius* chimeric protein (SEQ ID NO:14).

Figure 1:
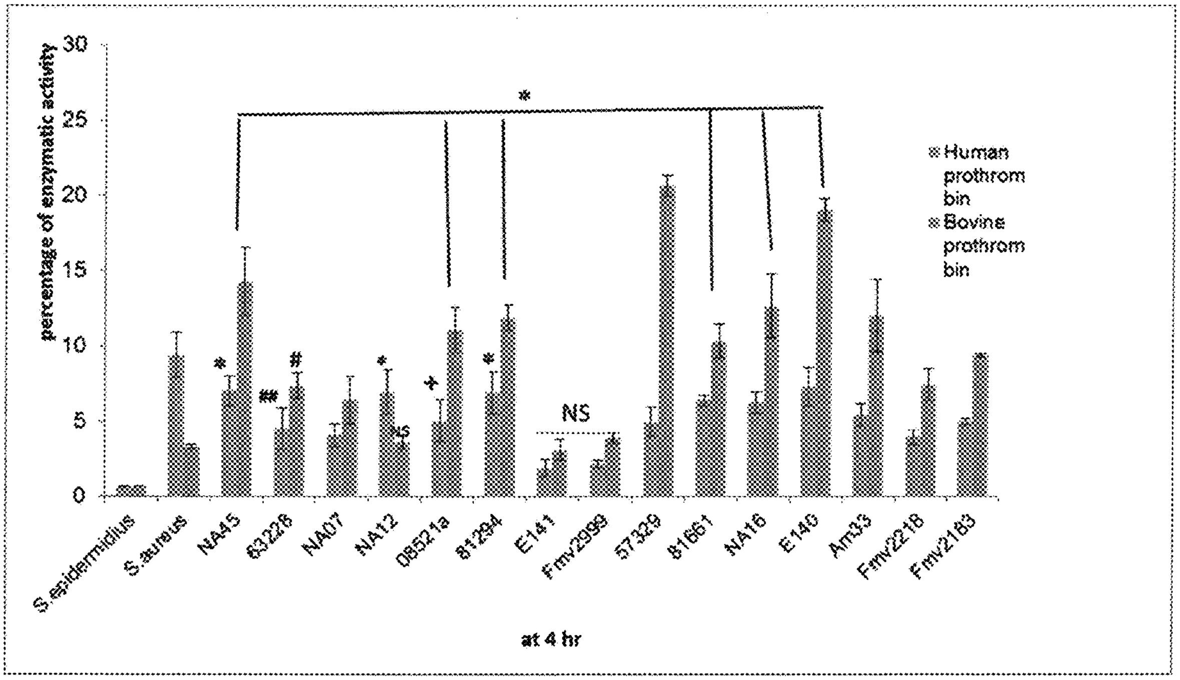
FIG. 1: *S. pseudintermedius* concentrated bacterial supernatants display clotting activity. The percentage of Coa prothrombin complex activity was interpreted by the change in the rate of S-2238 hydrolysis(Δabsorbance) over time (Δtime). At time zero there were no significant interactions between bacteria strains compared with the negative control (*S. epidermedius*) and prothrombin source ($p=0.959$) or positive control (*S. aureus*) and prothrombin source ($p=0.969$). There were significant interactions between bacteria strains comparing with the negative control and prothrombin type or positive control and prothrombin type ($p<0.001$) over time. *E141 and Fmv2999 were not significantly different from the negative control at all time points for human and bovine prothrombin. NA12 was not significantly different from the negative control at all time points for bovine prothrombin and significantly differed from the negative control at all time points (*$p<0.001$ for 1.4 hr), (++$p=0.039$ for 8 hr) for human prothrombin. *Comparing between NA45 and 063228, 08521a, 081294, 081661, E140, NA16, and *S. aureus* for their reactivity with human and bovine prothrombin. For bovine prothrombin reactivity, the E140 overall percentage change was significantly higher than all other strains ($p<0.001$), 0851a, 081294, NA16, NA45>S. aureus p=0.027, 0.004, 0.001, 0.000, 081294, NA16, NA45>063228 p=0.045, 0.014, 0.001 and NA45>081661 p=0.023. For Human prothrombin reactivity, S. aureus overall percentage change was significantly higher than all others except E140 (p=1.000) and 81294 (p=1.000) S. aureus>0851a, 63228, 81661, NA16, NA45 p=0.000, 0.000, 0.001, 0.001 and 0.016, 81294 was higher than all others except S. aureus, E140 and NA45 (p=0.4'72) 081294>08521a, 063228, 081661, NA16 p=0.000, 0.000, 0.037, 0.039 and NA45>0851a, 63228 0.013 and 0.000. At time point 4 hr; there were significant strain differences with the negative and positive control (p<0.001) for bovine and human prothrombin. 081294, E140, NA16, NA45, 81661 and 08521a all significantly differed from the negative control for bovine prothrombin (*p<0.001). 063228 significantly differed from the negative control (#p=0.012) and was not significantly different from the positive control for bovine prothrombin (p=0.467). It significantly differed from the positive control for human prothrombin (##p=0.025). 08521a, NA45, and 081294 significantly differed from the negative control (+p=0.036 08521a) (*p<0.001 NA45, 081294) and was not significantly different from the positive control (p=0.063 08521a) (p=1.000 NA45, 081294) for human prothrombin.
Figure 2:
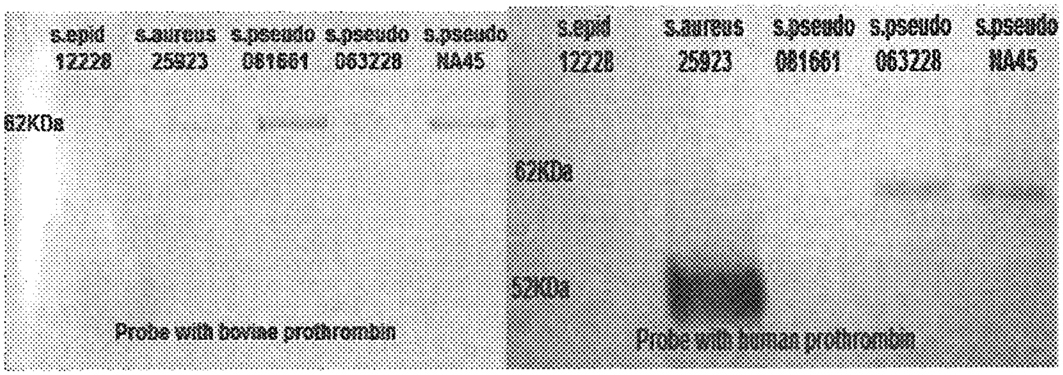
FIG. 2: Bovine and human prothrombin binding to overnight concentrated culture supernatant of NA45, 081661, and 063228 along with S. aureus and S. epidermedius as a control. Overnight supernatants were concentrated, separated by SDS-PAGE and the immunoreactive band (62 kDa, 52 KDa) was detected by Western blot analysis using (HRP)-strepavidin conjugate for the biotinylated bovine prothrombin in FIG. 3A and goat antihuman prothrombin antiserum HRP rabbit antigoat IgG (H+L) for human prothrombin in FIG. 3B.

Reference will now be made in detail to embodiments of the disclosed recombinant attenuated *S. pseudintermedius* cell-surface and secreted proteins, and multivalent immunogenic compositions and vaccines, examples of which are illustrated in the accompanying drawing figures.

DETAILED DESCRIPTION

Any citations, gene sequences, accession numbers, and reference sequences included or referred to in this application form a part of the disclosure and are incorporated herein in their entirety by reference. It will be appreciated that the embodiments shown and described in this patent application are an illustration of one of the modes best suited to carry out the invention. The invention is capable of other different embodiments, and its several details are capable of modification in various, obvious aspects all without departing from the invention. Accordingly, the drawings and descriptions provided herein will be regarded as illustrative in nature and not as restrictive. Various embodiments of the methods and compositions of the present disclosure will now be described by way of the following Examples.

*S. pseudintermedius* produce cell surface-bound and secreted proteins that variously inhibit phagocytosis, neutralize complement, bind immunoglobulins via their Fc and VH3 regions, cause apoptosis of B cells and kill leukocytes. Thus, these proteins contribute to the evasion of both the innate and adaptive branches of the immune system. In accordance with the foregoing need identified in the art, the present investigators have identified a number of such proteins as likely candidates for vaccines (see Table 1). Secreted *S. pseudintermedius* protein A acts as a superantigen, destroys B cells and prevents antibody production. *S. pseudintermedius* protein A bound to the surface of bacteria neutralizes antibody and prevents it from agglutinating, opsonizing or fixing complement. *S. pseudintermedius* adenosine synthase protein (AdsA) present on the bacterial surface produces adenosine from host-derived ATP, ADP and AMP found in damaged host tissue. The adenosine inhibits phagocytosis of bacteria by neutrophils. *S. pseudintermedius* coagulase facilitates the formation of a fibrin coating on the bacterial surface and is a hallmark of virulence in staphylococci although it has characteristics that differ significantly from coagulase produced by other coagulase-positive staphylococci. *S. pseudintermedius* leukotoxins, including leukotoxin S, leukotoxin F, and exotoxin 15 destroy leukocytes disabling their host's immune defenses.

TABLE 1

*S. pseudintermedius* Vaccine Antigens

| Antigen | Location | Rationale (contribution to virulence) |
|---|---|---|
| Adenosine synthase protein | Bacterial surface | Converts host ATP, ADP and AMP to adenosine which inhibits phagocytosis and bacterial destruction and clearance by neutrophils |
| Coagulase | Bacterial Surface and Secreted | Converts host prothrombin to thrombin resulting in fibrinogen conversion to fibrin. This facilitates formation of a protective coating of host protein on bacterial surface. Binds IgG and C3. |
| Exotoxin 15 | Secreted | Kills host leukocytes preventing innate and adaptive immune response. Neutralizes complement. |
| Leukotoxin S/F | Secreted | Kills host leukocytes preventing innate and adaptive immune response |
| Protein A | Bacterial Surface and Secreted | Binds antibody on bacterial surface preventing destruction of bacteria and serves as superantigen that destroys B cells and blocks host antibody response |

TABLE 1-continued

| *S. pseudintermedius* Vaccine Antigens | | |
|---|---|---|
| Antigen | Location | Rationale (contribution to virulence) |
| Multiple (Chimeria) Canine T cell epitope, Coagulase, LukS, Nucleotidase, Protein A | Bacterial Surface and Secreted | Converts host ATP, ADP and AMP to adenosine which inhibits phagocytosis and bacterial destruction and clearance by neutrophils. Converts host prothrombin to thrombin resulting in fibrinogen conversion to fibrin. This facilitates formation of a protective coating of host protein on bacterial surface. Kills host leukocytes preventing innate and adaptive immune response. Neutralizes complement. |

The functions of the above proteins in vitro were identified and confirmed using recombinant *S. pseudintermedius* proteins and canine leukocyte targets. Their secretion and/or surface accessibility was determined using culture supernatant, surface labeling, pull down experiments and GC mass spectroscopy. For GC mass spectroscopy log phase bacterial cultures of *S. pseudintermedius* strains (shown with their sequence types) 06-3228 (ST68), 08-1661 (ST71) and NA45 (ST84) were analyzed. These strains are representative of the major *S. pseudintermedius* genotypes (clonal complexes) most commonly isolated from canine infections in the United States and Europe.

Example 1—Mass Spectrometric Analysis of Whole Secretome and Surface-Associated Proteins from *Staphylococcus pseudintermedius*

*S. pseudintermedius* is known to produce a wide variety of virulence factors. Some of these are surface-associated while others are secreted. The purpose of the studies described herein was to analyze the whole secretome (secreted proteins) and surface-associated proteins in *S. pseudintermedius* by Mass Spectrometry (MS) in an effort to identify potential vaccine candidates. The specific objectives of this study were: (a) to analyze the entire bacterial secretome (b) to identify secreted immunoglobulin-binding (Ig-binding) proteins and (c) to identify proteins accessible on the surface of the bacteria.

The secretome, Ig-binding proteins and trypsin-treated proteins were compared among three *S. pseudintermedius* isolates using their respective genomes as reference databases. Orthologous proteins among the three isolates were identified and from this group, proteins common to all three isolates were further analyzed to determine if they were good vaccine candidates. Mass spectrometry was used to identify the surface proteins and secreted proteins from three strains of *S. pseudintermedius;* 06-3228 (ST 68), 08-1661 (ST71) and NA45 (ST 84) which are representative of the major clonal populations in the United States and Europe.

Materials and Methods

Bacterial Strains and Growth Conditions

*S. pseudintermedius* clinical isolates 06-3228 and 08-1661 were obtained from the Clinical Bacteriology Lab at the University of Tennessee, Knoxville. Strain NA45 was a gift of Faye Hartmann of the University of Wisconsin School Of Veterinary Medicine. Bacterial colonies from blood agar plates were inoculated into 5 ml of sterile Trypticase Soy Broth (TSB) (BD Biosciences, San Jose, Calif.) and incubated overnight at 37° C. with shaking at 225 rpm (Excella E24 Incubator Shaker, New Brunswick Scientific). Fifty microliters of overnight culture were inoculated into 5 ml of fresh, sterile TSB to initiate log-phase bacterial cultures. The bacteria were grown at 37° C. with shaking at 225 rpm until an optical density of $OD_{600}$=0.4-0.6 was reached.

Preparation of Whole Secretome

Log phase bacterial cultures were centrifuged at 10,000 g for 30 minutes at 4° C. (Sorvall RC-5C Plus Superspeed Centrifuge). Without disturbing the bacterial pellet, the supernatant was collected and passed through a 0.45 μm filter (Whatman, GE Healthcare Lifesciences, Pittsburgh, Pa.). The filtrate was concentrated using an Amicon® Ultra-4 centrifugal filter (EMD Millipore Corp., Billerica, Mass.) and stored at −20° C. until further analysis.

Purification of Immunoglobulin-Binding Proteins from Bacterial Culture Supernatants Log phase bacterial cultures were centrifuged at 10,000 g for 30 minutes at 4° C. The supernatant was passed through an IgG-sepharose column (GE Healthcare Lifesciences, Pittsburgh, Pa.). Briefly, the column was equilibrated with five bed volumes of binding buffer containing 50 mM Tris, 2.7 mM potassium chloride and 0.137 M NaCl pH 8.0. The bacterial supernatant was added to the column to allow attachment of IgG binding proteins. Unbound proteins were washed off with 15 bed volumes of binding buffer. The bound proteins were eluted in 0.1-0.2 M Glycine/HCl pH 2.5-3.0. The pH of the elution fraction was adjusted to 7.0 using 0.5M Tris and stored at −20° C. until further analysis.

Purification of Trypsin-Treated Surface Proteins

Log phase bacterial cultures were centrifuged at 4,200 g for 3 min and washed three times with PBS. The pellet was suspended in 1 ml digestion buffer (0.6M sucrose buffered with 50 mM Tris, pH 7.5). 200 μg of porcine trypsin (Sigma-Aldrich, St. Louis, Mo.) was added and the cells were digested for 1 hour at 37° C. Protease inhibitor cocktail set IV (Calbiochem, EMD Millipore Corp, Temecula, Calif.) was then added to the mixture at a final concentration of 0.1 μg/ml. The supernatant containing tryptic peptides was stored at −20° C. until further analysis.

Biotin Labeling of Surface Proteins

Log phase bacterial cells were harvested by centrifugation at 10,000 g for 1 min and washed twice with ice-cold phosphate buffered saline (PBS) pH 8.0. 100 μl of 10 mM EZ-Link Sulfo-NHS-LC-Biotin reagent (Thermo Scientific, Waltham, Mass.) per 1 ml of cell suspension was added and incubated for 30 min at room temperature. The cells were washed three times with PBS and 100 mM glycine was added to quench and remove excess biotin. The biotin-labeled bacteria were stored in aliquots at −20° C. until further use. The biotin-labeled proteins were digested with trypsin as described previously and were stored at −20° C. until further use.

Purification of Biotin-Labeled Surface Proteins Using Monomeric Avidin

Biotin-labeled surface proteins were purified using a monomeric avidin column (Pierce Monomeric Avidin Kit, Thermo Scientific, Waltham, Mass.) as per manufacturer's protocol. Briefly, the monomeric avidin column was washed with 8 ml of PBS followed by the addition of 6 ml of biotin blocking buffer to block any non-reversible biotin binding sites. The excess biotin was removed from the reversible binding sites by addition of 12 ml of regeneration buffer. The biotin-labeled, trypsin-cleaved proteins were loaded onto the column. Unbound proteins were washed off with PBS. The bound proteins were eluted using elution buffer in six, 2 ml fractions. The eluates were stored at −20° C. until further use.

LC-MS/MS Analysis of *S. pseudintermedius* Secretome and Surface-Associated Proteins Samples interrogating *S. pseudintermedius* supernatant and surface-associated proteins were prepared for shotgun LC-MS/MS analysis. Trypticase soy broth (media alone) and bacterial culture supernatant passed through control Sepahrose beads (without IgG) served as controls. Prior to protein denaturation with sodium dodecyl sulfate (SDS), samples were concentrated/solvent exchanged on molecular weight cut-off (MWCO) spin filters (Vivaspin, GE Healthcare Lifesciences, Pittsburgh, Pa.) that retain proteins/polypeptides>5 kDa in size (~50 amino acids or larger). Retained proteins were then re-suspended in 4% SDS, 100 mM Tris-HCl, 5 mM dithiothreitol (DTT), transferred to an Eppendorf tube, and incubated at 95° C. for 5 min. Iodoacetamide was then added to a final concentration of 15 mM and samples incubated for 20 min in the dark at room temperature. Denatured and reduced proteins were then digested to peptides with 2 µg of proteomics-grade porcine trypsin (Sigma-Aldrich, St. Louis, Mo.) for 4 hours. Following digestion, peptide samples were adjusted with 200 mM NaCl-0.1% formic acid and passed through a 10 kDa MWCO Vivaspin2 spin filter to collect appropriately sized tryptic peptides for LC-MS/MS analysis.

With the aid of a pressure cell, peptides were loaded onto a biphasic MudPIT back column containing both strong-cation exchange and reversed-phase (RP) resins-5u Luna or 5u Kinetex, respectively (Phenomenex, Torrance, Calif.) and separated. Briefly, loaded samples were washed offline then placed in line with an in-house pulled nanospray emitter packed with 15 cm of RP resin. Peptides were then separated and analyzed with either a 2-step MudPIT LC-MS/MS protocol (salt cuts of 50 mM and 50 mM ammonium acetate) over a 4-hr period (supernatant samples) or a 1-step protocol (500 mM ammonium acetate) over a 2-hr period (surface proteins and pulldown samples). All samples were measured with a hybrid LTQ XL-Orbitrap (Thermo Scientific, Waltham, Mass.) mass spectrometer (MS) as follows: data-dependent acquisition, 1 full scan followed by 10 MS/MS scans. Orbitrap mass analyzer was set to 15K resolution, LTQ isolation window=2.2 m/z, monoisotopic precursor selection, dynamic exclusion window, duration, and max=3 m/z, 60 s (30 s for supernatant samples), and 500 respectively. The immunogenicity of peptides was predicted using the POPI v.2.0 web server.

Results

LC MS/MS Data Analysis

MS/MS spectra were searched against sample-specific proteome databases concatenated with common protein contaminants using MyriMatch v.2.2. Peptide spectrum matches (PSM) were filtered and assembled to proteins using IDPicker v.3.0 with false-discovery rates, as assessed by evaluating MS/MS spectra that matched to reversed decoy sequences, controlled at <1% at the peptide-level. Proteins calls required two distinct peptides at a minimum. Peptide intensities were assessed by chromatographic area-under-the-curve (AUC) using IDPicker's embedded spectra/label-free quantification option and protein abundances derived via summation of constituent peptides intensities. To qualitatively compare the proteins identified across each strain of *S. pseudintermedius*, OrthoMCL (OrthoMCL Database, Version 5.0) was employed to identify orthologous protein sequences. Identified protein data for each specific *S. pseudintermedius* sequence type were then re-cast into their orthologous groups and compared across all sample types to identify proteins common to all three pathogenic strains with special emphasis on those that are surface-associated and/or secreted. To help winnow down the list of potential secreted and surface-bound antigen targets, PSORTb v.3.0 was used to assign subcellular location to each identified protein.

Identification of Surface Proteins, IgG-Binding Proteins and Extracellular (Secreted) Proteins by Mass Spectrometry Using the analysis method described above, a total of 580 proteins were identified in the isolate 06-3228, 596 in 08-1661 and 542 in NA45. In order to narrow down the spectrum of proteins for analysis across all three sequence types, ortholog protein prediction was performed using the web-based tool OrthoMCL. A total of 364 predicted orthologous proteins were identified across all three sequence types. Excluding proteins that were classified as cytoplasmic in origin, there were 72 proteins predicted to be either secreted, cell wall-associated or of unknown cellular location across all three sequence types. These proteins were evaluated for inclusion in a vaccine based on their predicted virulence characteristics.

Example 2—Identification, Cloning, and Characterization of Coagulase from *S. pseudintermedius*

Upon contact with host blood, the coagulation system prevents the dissemination of microbial invaders by fibrin deposition around microbes. Phagocytosis of bacteria by neutrophils is strongly enhanced by opsonization of bacteria with plasma factors such as antibodies and complement. Staphylococci use several mechanisms to generate a protective coat composed of polysaccharide capsule or fibrin that prevent uptake of staphylococci by neutrophils or macrophages. Coagulase (Coa) is an important virulence factor that interacts with fibrinogen (Fg) and induces the formation of fibrin clots through activation of prothrombin that enables the establishment of staphylococcal disease. Coagulase activity has been observed in *S. pseudintermedius*, however, the responsible protein has not been identified or studied.

A recombinant protein (prCoa) was produced from the *S. pseudintermedius* gene commonly annotated as von Willebrand factor binding protein but which shares only 40% similarity to the same protein in *S. aureus*. A chromogenic assay was used to measure the activity of the staphylocoagulase-prothrombin complex directly for comparing the affinity of *S. pseudintermedius* Coa to prothrombin from bovine or human origin. Weak specificity for human prothrombin compared to bovine prothrombin was observed. The ability of prCoa to facilitate the escape of *S. pseudintermedius* from phagocytosis by forming a bridge between opsonizing antibody, complement and fibrinogen was studied. Evidence from this work suggests *S. pseudintermedius* Coa is an important candidate for a novel therapeutic or a novel vaccine that may elicit antibodies that enhance phagocytic clearance. The aim of this study was to identify the coagulase protein of *S. pseudintermedius*, clone the gene and produce a recombinant protein to study its biological properties.

Material and Methods

Bacterial Strains

A total of 15 clinical isolates previously identified as *S. pseudintermedius* (Table 2) and submitted to the University of Tennessee, College of Veterinary Medicine Clinical Bacteriology Laboratory as well as from European and North American collaborators were used. They represent nine MLST lineages associated with methicillin resistance. Bacterial isolation and identification procedures were those routinely used in the laboratory substantially as described above. Isolates were grown and maintained on tryptic soy blood agar (BD). *S. aureus* strain (ATCC23529) and the *S. epidermidis* (ATCC12228) were used as controls.

TABLE 2

Origins, sequence type of *S. pseudintermedius* strains

| *S. pseudintermedius* strain | Country | Sequence type |
|---|---|---|
| NA45 | USA | ST84 |
| NA12 | USA | ST64 |
| NA07 | USA | ST124 |
| NA16 | USA | ST71 |
| 081661 | USA | ST71 |
| 063228 | USA | ST68 |
| 0821a | USA | ST68 |
| 081294 | USA | ST68 |
| FMV2999-10 | Portugal | ST199 |
| FMV2218-10 | Portugal | ST198 |
| FMV2183-10 | Portugal | ST197 |
| Am33 | Thailand | ST111 |
| 57395 | Israel | ST45 |
| E140 (DK729) | Denmark | ST71 |

DNA Extraction

All DNA manipulations were performed using standard methods (Sambrook et al., 1989). Isolates were grown on blood agar plates overnight at 37 C and bacteria derived from a single colony were suspended in 5 ml of trypticase soy broth (TSB) (Becton, Dickinson and Co., Sparks, Md.) in a rotary shaker at 225 rpm. Bacteria were harvested from 1.8 ml of microbial culture and DNA extracted using the UltraClean® Microbial DNA Isolation Kit (MO BIO, No 12224-50).

PCR Primers and Conditions

Primers were designed for amplification and sequencing of the *S. pseudintermedius* putative coagulase and vWbp genes based upon published NA45, 063228, and 081661 our genomic data (GenBank accession no. CP016072.1, CP015626.1, and CP016073.1 respectively; Table 3) using the IDT SciTools application (Integrated DNA Technologies, Coralville, Iowa). PCR amplification of the full-length coa genes was carried out with oligonucleotide primers (Table 4). The reaction mixtures consisted of 25 μl total volume solutions containing 2.5 μl of genomic DNA, 20 pmol of each primer (1 μl), 12.5 μl rTaq polymerase enzyme, and 8 μl nuclease free water. Amplification conditions consisted of an initial denaturation (94 C for 1.5 min) followed by 35 cycles of denaturation (94c for 60 s), annealing (55 C for 2 min), and extension (72 C for 60 s), with a single final extension (72 C for 5 min). PCR products were visualized on 1.4% agarose gels.

TABLE 3

Primers used with conventional PCR

| Primer sequence (5′-3′) |
|---|
| F; TTTGGCCATGGATGAAAAAGAAATTGCTT |
| R; TTTGGGGATCCTGACCGTTGTAAGCTTTAT |

Restriction enzyme sites (underlined) for Nco I and BamH1 were designed in the forward primer/reverse primer.

Sequence Analysis

PCR products of expected sizes were treated to destroy single-stranded DNA using ExoSap-IT purification reagent (USB Corp., Cleveland, Ohio) and submitted to the University of Tennessee, Molecular Biology Resource Facility for DNA sequencing using the dideoxy chain-termination method. PCR primers were used for direct DNA sequencing of PCR amplification products. BLAST sequence alignment tool (ncbi.nlm.nih.gov/blast/) and Geneious software were used to determine nucleotide sequence similarity between *S. pseudintermedius* isolates.

Cloning, Expression, and Purification of Coa Protein

Cloning of the coa gene was carried out according to the manufacturer's instructions using pETBlue™-2(Novagen) vector with an expanded multiple cloning site (MCS) and C-terminal HSV•Tag® and His•Tag® sequences, an ampicillin resistance gene and lacZ region for blue/white screening. PCR amplification of full-length coa was carried out with oligonucleotide primers which included NcoI and BamHI restriction sites to facilitate cloning. PCR products from *S. pseudintermedius* strain 081661 were digested with NcoI and BamHI and purified using Wizard® SV Gel and PCR Clean-Up System according to the manufacturer's instructions. They were ligated into the vector, transformed into DH5-alpha *E. coli* and plated on LB agar containing 50 μg/ml ampicillin, IPTG, 40 μg/ml X-gal. The recombinant plasmid was extracted using a GeneJET Plasmid Miniprep Kit according to the manufacturer's instructions. The presence of the cloned fragment was confirmed by PCR.

The coa gene construct was expressed in Tuner™ (DE3) pLacI *E. coli* competent cells (Novagen). They were plated on LB agar containing 50 μg/ml ampicillin and 34 μg/ml chlormphenicol (LB amp-cam). Exponential phase cultures were inoculated 1:100 from overnight starter cultures and grown to an optical density (600 nm) of 0.6. Isopropyl β-D-thiogalactopyranoside (SIGMA) was added to a final concentration of 1 mM and the cells were incubated at 30° C. for an additional 4 min in a shaking incubator at 225 rpm with aeration for induction of protein expression.

For the purification of recombinant protein, 100 ml of induced bacterial cultures were centrifuged at 10000×g for 15 min. Bacteria were suspended in 5 ml of Bug Buster master mix (Novagen) with 20 μl protease inhibitor (Cocktail Set III, EDTA-Free—Calbiochem) and incubated for 30 min at 37 C in a shaking incubator at 225 rpm. Samples were centrifuged at 16,000×g for 45 min at 4° C. to remove insoluble cell debris. Proteins were applied to an immobilized metal ion affinity chromatography according to the manufacturer's instructions (PrepEase Ni-TED column). Proteins were eluted using HIS-Select Elution Buffer (Sigma) containing successively higher concentrations of imidazole up to 250 mM. Protein concentrations were determined with the bicinchoninic acid (BCA) assay (Thermo Scientific).

A chromogenic staphylocoagulase assay was used to detect the presence of *S. pseudintermedius* coagulase. Single colonies of bacterial isolates were cultured overnight in 2 ml of TSB at 37° C. Bacteria were centrifuged at 12000×g for 2 min then supernatants were concentrated using Amicon Ultra-0.5 centrifugal filters. Tests were performed in flat-bottom microtiter plates. The molar concentrations of staphylocoagulase (SC) and prothrombin (P) were calculated using molecular weights of 62,000 for coagulase and 72,000 for human and bovine prothrombin. An 18 μl aliquot of concentrated supernatant or an equimolar amount of purified prCoa was mixed with 1×10-16 M of human prothrombin or bovine prothrombin and incubated for 30 min at 37 C. Chromogenic thrombin tripeptide substrate H-D-Phe-Pip-Arg-pNA (S-2238) was added to a final concentration of 1 mM in a total reaction buffer of 100 μl PBS per each well. After an initial reading the reaction was allowed to proceed by incubating in the dark for 1, 4 or 8 h at 37 C. The absorbance was continuously measured at 405 nm and positive, negative, and reagent controls (prothrombin alone without the substrate) were included with each batch, with *S. aureus* ATCC25923 as the positive control and *S. epidermidis* ATCC12228 as the negative control. The change in absorbance was plotted and the slope of the curve (dA/dt) was interpreted to be the rate of S-2238 hydrolysis was measured as the increase in the absorbance, and thus reflective of enzymatic function (% Coa prothrombin complex activity). The generated thrombin activity in the supernatant was measured using chromogenic thrombin peptide.

Phagocytosis Assays

For fluorescent labeling of *S. pseudintermedius* 081661 strain with pHrodo dye (Invitrogen, Mulgrave, Australia), bacteria were suspended in PBS, pH 7.2 and incubated with 1 mM of pHrodo™ Green DMSO solution for 45 minutes at room temperature protected from light. Bacteria were washed twice with PBS, suspended in PBS and 10% glycerol, and stored at −80° C. until further use.

For whole blood phagocytosis, 10 μL of pHrodo green-labeled *S. pseudintermedius* 081661 strain ($10^9$ cell/ml) were mixed with 10% rabbit plasma for 30 min at 37 C in the presence of prCoa (50 or 100 μg/ml) or buffer. Then 200 μl of dog blood freshly collected in EDTA, was added and incubated for 30 min at 37 C. The reaction was stopped using red blood cell lysing buffer (Sigma); samples were washed with PBS and analyzed by flow cytometry. Gating of cells was done on the basis of forward and side scatter. For each sample fluorescence intensity of 10,000 gated neutrophils was determined. Phagocytosis was expressed as the percentage of neutrophils that became fluorescent.

Flow Cytometry Assays with *S. pseudintermedius* and *S. epidermidius*

Bacteria grown to mid log phase were incubated with 50 μl dog serum for 30 min at 37 C, washed with PBS and incubated with prCoa (50 μg/ml) for 1 hour at 37 C with shaking. After another washing step, bacteria were incubated with FITC conjugated Fg from pooled human plasma (50 μg/ml, Zedira) for 1 hour at 37 C with shaking. Controls included heat inactivated serum with added prCoa, FITC-fibrinogen or dog serum only with FITC-fibrinogen. Washed bacteria were analyzed by flow cytometry. Bacteria were gated on the basis of forward and side scatter properties and 10,000 bacteria were analyzed.

Binding Assays

To detect the ability of prCoa to bind with complement factor C3, microtiter plates were coated overnight at 4° C. with affinity purified goat anti-dog C3 (Bethyl) (10 μg/ml). After washing the wells with PBST, dog serum (undiluted and two-fold serially diluted) were added and incubated for one hour at 37 C, then incubated with prCoa (5 μg/ml) for another hour at 37 C. prCoa binding was detected using a 1:3000 dilution of HRP-conjugated goat anti-HIS monoclonal antibody (Thermoscientific) and visualized using TMB (Pierce) substrate.

To detect the binding of IgG, IgG-Fc, and IgG-Fab to prCoa, canine IgG was digested with immobilized papain using a Fab preparation Kit (Thermo Scientific) according to the manufacturer's instructions using a 6 hr incubation for 1 mg/ml dog IgG whole molecule (Rockland) with papain. Digestion was ensured by diluting the sample in Laemmli sample buffer 2× without reducing agent (Biorad) and running the digested IgG molecule in 7.5% polyacrylamide gels. This was followed by purification and separation of Fab fragments from Fc fragments using prepacked, immobilized Thermo Scientific™ NAb™ Protein A Plus Spin Column. prCoa (2 μg/ml) coated plates were incubated with canine whole molecule IgG (Rockland), Fc, or Fab fragments (beginning concentration 10 μg/ml then two-fold serially diluted) for one hour at 37 C. After washing, HRP conjugated sheep anti-dog IgG heavy chain (1:4000) (Invitrogen) was added and detected through incubation with TMB substrate.

To measure the binding of prCoa to prothrombin human and bovine prothrombin (2 μg/ml) was adsorbed to a microtiter plate well at 4° C. for 16 h. After washing the wells with PBST, prCoa (beginning with 2 μg/ml then two-fold serially diluted) was added and the plates were incubated for 1 h. Following incubation with HRP-conjugated goat anti-His monoclonal antibodies (thermoscientific) (1:3,000 dilution) for 1 h, TMB substrate (Pierce) was added. Bound proteins were quantified by measuring the absorbance at 450 nm in a microplate reader. All experiments were performed twice for reproducibility.

Statistical Analysis

Repeated measures mixed effects analyses of variance were used to test within and between subject effects for binding ability of prCoa (human and bovine prothrombin, complement C3 and IgG, Fab, Fe), bacterial supernatant and the coagulase recombinant protein chromogenic assay and phagocytosis assay. A 2×4 analysis of variance was used to test between subject effects for fibrinogen FITC deposition. Post hoc analysis included simple contrasts when comparing to a control or pairwise comparisons. All post hoc tests used a Bonferonni adjustment.

Results

Amplification and Sequencing of the Coa Gene from *Staphylococcus pseudintermedius* Strains PCR analysis showed that the putative *S. pseudintermedius* coagulase gene was found in all 15 clinical isolates of *S. pseudintermedius* tested at the expected size of 1500 bp (data not shown).

Time Course of the Hydrolysis of Chromogenic Substrate with Concentrated Culture Supernatant The use of a chromogenic assay shows that supernatant of all *S. pseudintermedius* strains contains sufficient staphylocoagulase for detection within 1 h except E141. Fmv2999 was negative for coagulase reactivity with human or bovine prothrombin and NA12 only reacted with human prothrombin and not bovine prothrombin as shown in FIG. 1. There was a marked increase in hydrolyzation of the chromogenic substrate by *S. pseudintermedius* strains with bovine prothrombin compared to human prothrombin. The overall percent change of almost all *S. pseudintermedius* strains was significantly higher than *S. aureus* in their reactivity with bovine prothrombin. The overall percentage change of strain E140 was significantly higher than all other strains followed by NA45 and 081661 with strain 063228 exhibiting the lowest activity. The reverse occurred with the *S. aureus* as its overall percentage change was significantly larger than all *S. pseudintermedius* strains in their reactivity with human prothrombin followed in order by 081294, NA45, 08521a, and 063228 as shown in FIG. 1.

The presence of coa and the production of staphylocoagulase by the *S. pseudintermedius* strains (n=15), were assayed by PCR, the plasma tube clotting method, and chromogenic assay as shown in Table 3 and FIG. 1. All strains tested positive for coa. The percentage of staphylocoagulase-positive reactions was 13/15 (86.6%) with the chromogenic assay.

Binding of 081661, 063228, NA45 Concentrated Bacterial Supernatant with Human and Bovine Prothrombin Binding of Prothrombin, Canine IgG, and Complement C3 to Coagulase Recombinant Protein of *S. pseudintermedius* Strain 081661

Figure 3:
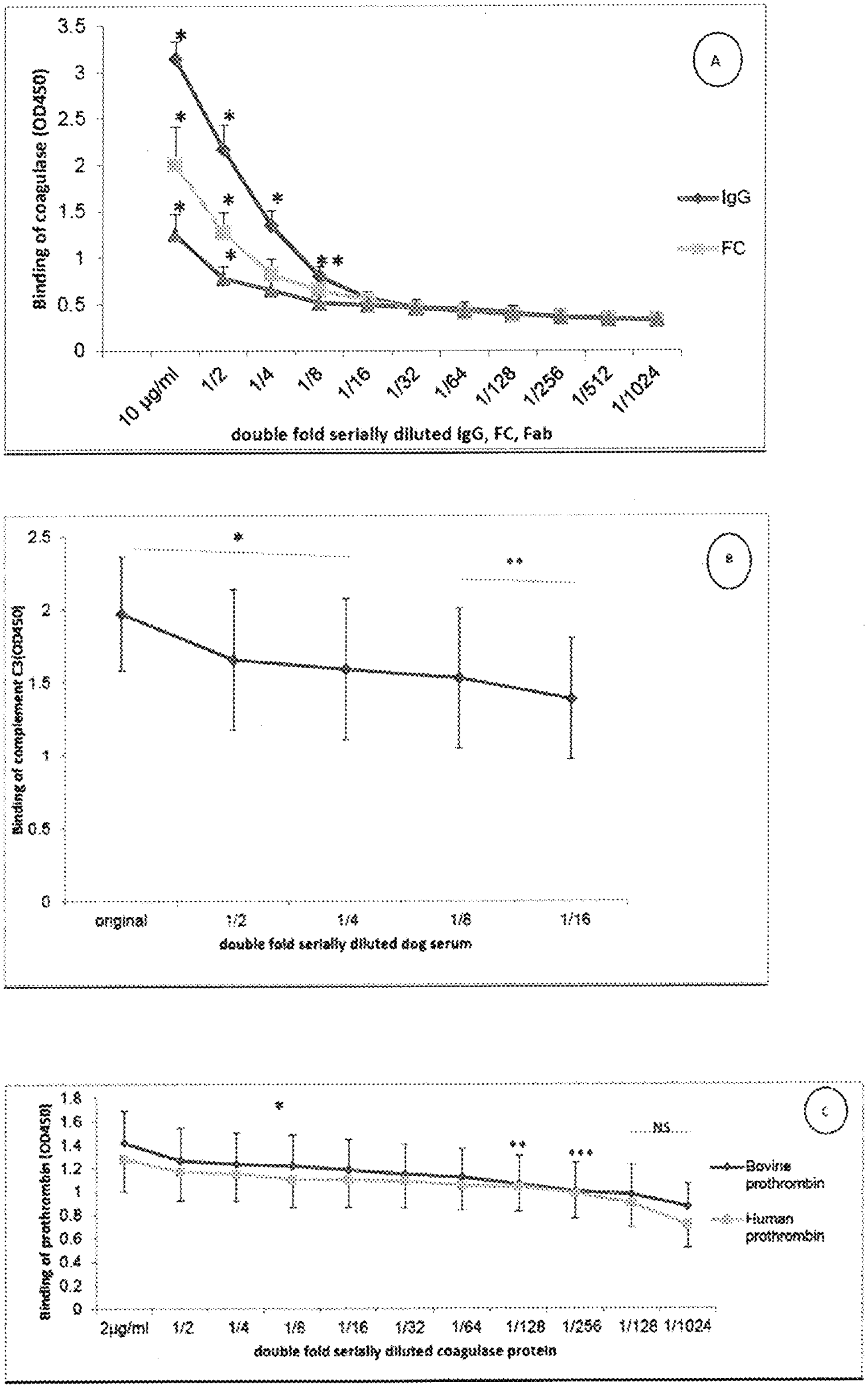
FIG. 3: Full-length coagulase protein binding to prothrombin, canine IgG, and complement C3: Graphs are a representative of 3 independent experiments. A) ELISA showing that coa can bind canine IgG, Fc and Fab domains. There was a significant interaction of treatment (IgG, Fc, Fab) on the binding ability of coagulase protein p=0.010. All three treatments had significant differences between concentrations: Fab p<0.001, Fc p<0.001, and IgG p<0.001. when comparing each concentration to the negative control. For IgG, only 10 µg/ml (*p<0.001), ½ (*p<0.001), ¼ (*p<0.001), and ⅛ (**p=0.003) were significantly different from the negative control. For Fc, only 10 µg/ml (*p<0.001), and ½ (*p<0.001) were significantly different from the negative control. For Fab, only 10 µg/ml (*p<0.001), ½ (*p<0.001), were significantly different from the negative control. The coagulase protein bound IgG and Fc more than Fab. For 10 µg/ml, IgG bound significantly higher than Fab (p=0.008). IgG and Fc were marginally different (p=0.071) and For ½, IgG was significantly higher than Fab (p=0.008). IgG and FC were marginally different (p=0.054). B) Binding of captured complement C3 to coa protein. All concentrations were significantly different from the negative control. The first three concentrations differed *p<0.01(0.000-0.001-0.003) and the last two concentrations differed at **p<0.05 (0.011-0.045). C) Binding of coa protein to the immobilized human and bovine prothrombin. There was no significant interaction of prothrombin type (human or bovine) on the binding ability of coagulase protein (p=0.785). All concentrations significantly differed from the negative control (p<0.05) *0.000, 0.002, and *0.012 except for concentration 1/512 (p=0.053) and 1/1024 (p=0.739) were not significant (Ns).
Figure 4:
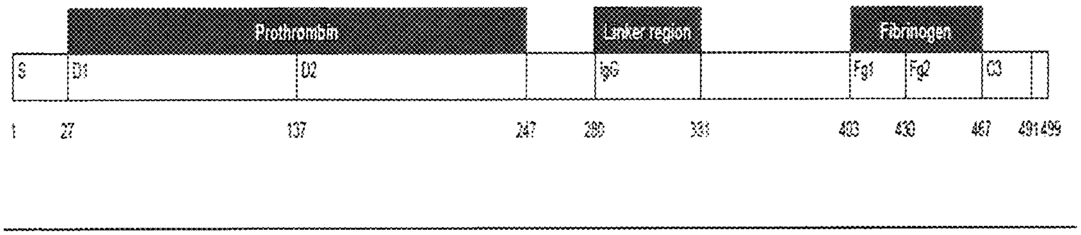
FIG. 4: Drawing to illustrate the predicted structure of coagulase protein cloned from S. pseudintermedius 081661 strain; including signal peptide (S), the D1 and D2 domain for prothrombin binding, the linker (L) domain containing IgG binding domain, the fibrinogen binding domain of Coa, and complement binding domain. Numbers indicate amino acid residues.

The ability of coagulase to bind to immobilized complement C3 is shown in FIG. 3B. Coa protein bound to both human and bovine prothrombin (FIG. 3C). By additional cloning, DNA sequence analyses and functional binding assays, the complete coa gene was found to consist of an open reading frame of 1500 bp nucleotides encoding Coa with a predicted molecular mass of 62 kDa. It corresponds to bases 2488877 to 2490385 in GenBank CP015626 from the genome of *S. pseudintermedius* 063228. Sequence comparisons of the deduced amino acid sequence of the respective domain by initial BLAST search with Efb protein of *S. aureus* revealed that this protein is related to the first fibrinogen binding domain called Efb-A, as it contains two subsegments corresponding to Coa residues 403-430 and 431-466 that show 38% and 50% amino acid identity to Efb-A. This suggests that the Fg binding activities in Efb and Coa are both located in disordered regions and both proteins may induce a protective Fg-containing barrier around staphylococci (FIG. 4). In addition, it was found that the *S. pseudintermedius* coa protein is related to *S. aureus* coa in the N-terminal prothrombin binding domain as represented in Coa residues 74-247 (FIG. 4). In addition, coa residues 280-331 in the linker region between the prothrombin binding domain and fibrinogen binding domain show a shared IgG binding domain beginning with the second two glutamic acids and ending with another two glutamic acids (FIG. 4). Coa residues 467-491 showed 38% and 44% identity to complement binding domains of sbi NA45 protein of *S. pseudintermedius* and *S. aureus* respectively with R470, N 478 and 7 linker amino acids in between (FIG. 4).

Detection of the Clotting Activity of Coagulase Recombinant Protein

Strong coagulation of rabbit plasma was detected with a single colony of *S. pseudintermedius* 081661. Both concentrations of prCoa tested yielded positive results within 5 hr after inoculation and remained at 24 hr.

The use of a chromogenic assay (FIGS. 5A-5B) showed that *S. pseudintermedius* prCoa produces sufficient hydrolysis for detection in 1 h and this hydrolysis was more pronounced when using bovine prothrombin than human prothrombin.

Coagulase Mediated Fibrinogen Covering of *S. pseudintermedius* and *S. epidermedius*

Figure 6:
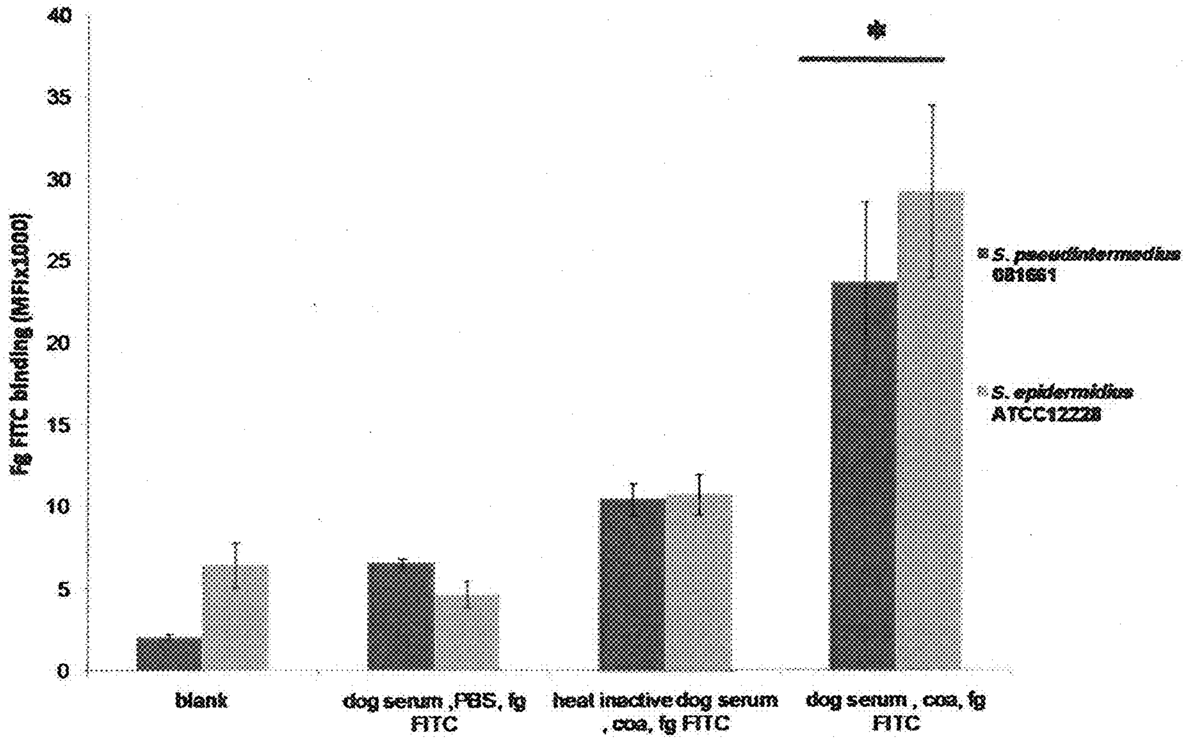
FIG. 6: fibrinogen deposition by coa is independent on S. pseudintermedius and extended to coagulase negative S. epidermedius. Binding of FITC-labeled Fg (50 µg/ml) to serum opsonized S. pseudintermedius and S. epidermedius in the presence of coa. Graph represents mean and S.E. of three independent experiments. The differences of fibrinogen FITC deposition between bacterial strains (S. pseudintermedius 081661 and S. epidermedius ATCC12228) were not significant (p=0.28'7). When comparing each serum type to the negative control (blank) only dog serum, coa, fg-FITC significantly differed from the negative control (*p<0.001) that had a significantly higher mean fluorescence than the negative control while dog serum, fg FITC (p=1.000) and heat inactivated dog serum, coa, fg FITC (p=0.091) did not significantly (NS) differ from the negative control.
Figure 7:
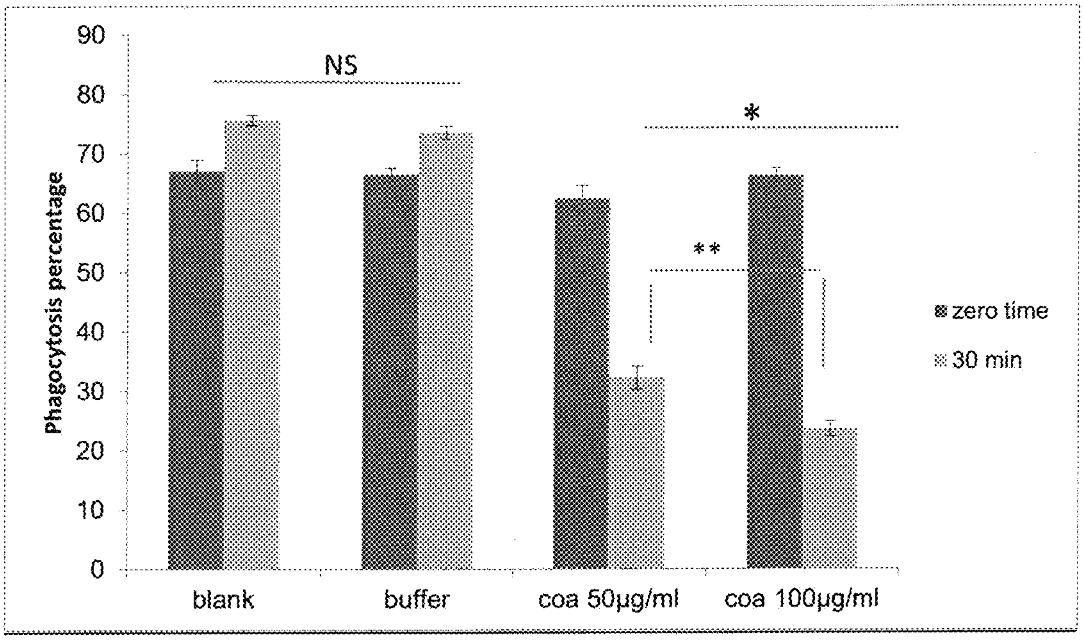
FIG. 7. Full-length coa inhibits phagocytosis of S. pseudintermedius Phagocytosis of fluorescently labeled bacteria when incubated in the presence of rabbit plasma and whole dog blood and coa (50, 100 µg/ml). Graph represents mean and S.E. of three independent experiments. All four treatments show significant changes over time (zero, 30 min). Blank (p=0.015), coa 50 μg/ml (p=0.003), coa 100 μg/ml (p=0.001) and elution buffer (p=0.002). When comparing each time over the treatments. At time 0 there were not significant treatment differences (p=0.257). At time 30, there were significant treatment difference (p<0.001). By comparing the phagocytic engulfment at each time point for each treatment, the blank and buffer both show significant increases in phagocytic engulfment of the bacteria over time (p=0.015), (p=0.002) respectively. The two coa treatments show significant decreases in phagocytic engulfment of the bacteria over time p=0.003 for coa 50 μg/ml, and p=0.001 for coa 100 μg/ml. Treatments differed at time 30. Blank and buffer significantly differed from both COA treatments (*p<0.001) but the blank did not differ from elution (p=1.000). There was a small significant difference between coa 50 μg/ml and coa 100 μg/ml (**p=0.012).
Figure 8:
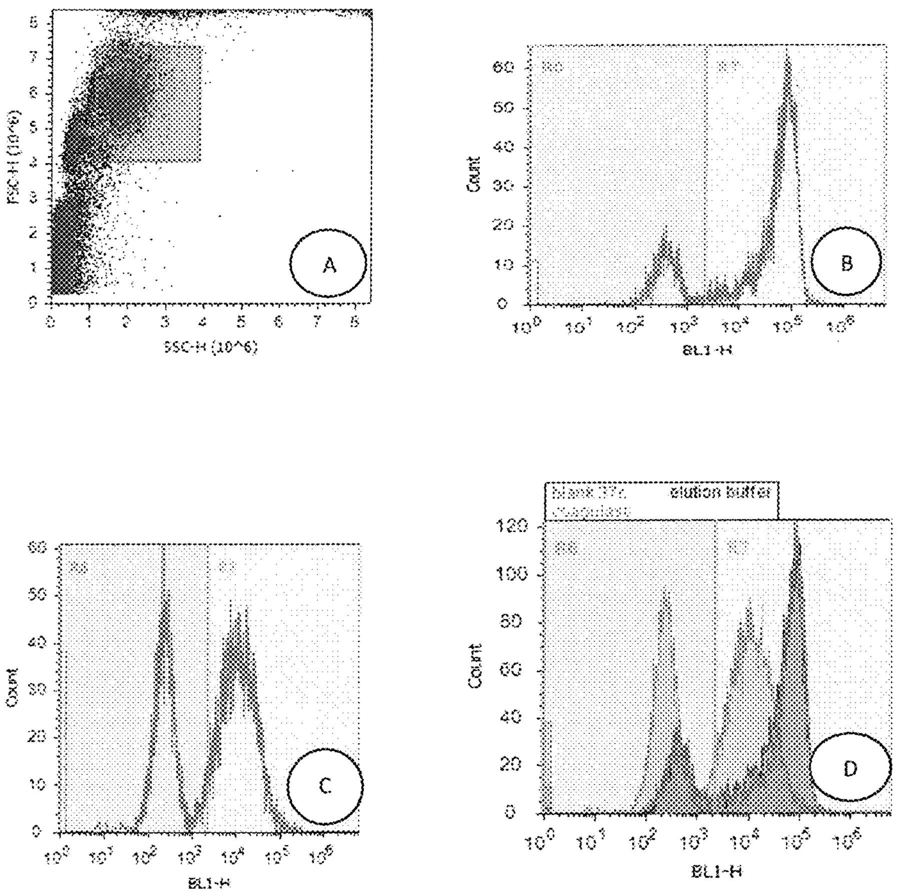
FIG. 8. Purified coagulase blocks phagocytosis. A) Dot plot of neutrophils gated based on forward and side scatter properties. B) Representative histogram of ex vivo phagocytosis of PHrodo labeled *S. pseudintermedius* incubated with normal dog whole blood (normalized phagocytosis). C) Representative histogram of ex vivo phagocytosis of PHrodo labeled *S. pseudintermedius* incubated with dog whole blood, rabbit plasma, and coagulase. D) Overlay histogram of normalized phagocytosis and the effect of coagulase versus the elution buffer to block neutrophil engulfment.

Using flow cytometry we observed that coa mediates Fg binding to opsonized bacteria (FIG. 6). These experiments show that coa binds to C3 and IgG on the bacterial surface and subsequently attracts Fg. To study whether coa interacts with *S. pseudintermedius* specifically, we analyzed whether purified prCoa can cause fibrinogen deposition on other bacteria including coagulase negative and non-biofilm producer *S. epidermidis* ATCC12228. Fibrinogen deposition by coa was evaluated by flow cytometry in the same manner as for *S. pseudintermedius*. prCoa facilitated deposition of fibrinogen on these bacteria as well, suggesting that *S. pseudintermedius* coa may protect some non-Coa producing bacteria (FIG. 6).

Coa Inhibits Phagocytosis in the Presence of Rabbit Plasma prCoa blocked phagocytosis in a reaction that depends on the interaction of coa with both prothrombin and fibrinogen to form a protective fibrin shield around the bacteria (FIG. 7 and FIGS. 8A-8D).

Discussion

Coagulase activity is considered a key virulence factor for *S. pseudintermedius*. The coagulase gene identified in *S. aureus* does not have significant similarity to any genes found in *S. pseudintermedius*. The *S. pseudintermedius* gene annotated previously as producing von Willebrand factor binding protein, however, is only 40% similar to the corresponding *S. aureus* gene. The predicted *S. pseudintermedius* protein has domains similar those of proteins with coagulase activity and for that reason was investigated for its coagulase function.

Although some non-staphylocoagulase-producing *S. pseudintermedius* strains test positive in the tube coagulase test, it was found by PCR analysis that the occurrence of the putative coa gene (often annotated previously as von Willibrand binding protein) examined in this study is common among clinical isolates of *S. pseudintermedius*.

The chromogenic assay showed that 063228 coagulase activity is not significantly different from *S. aureus* at all time points with bovine prothrombin indicating that this strain is able to form a complex with bovine prothrombin. It was significantly different from *S. aureus* with human prothrombin indicating that this strain is able to form a complex with human prothrombin but with less reactivity than *S. aureus*.

The coagulase recombinant protein was able to bind with canine IgG, Fc and Fab domains. Based on BLAST sequence alignment of IgG binding domain and the linker domain (L), the most likely region that binds with IgG is the linker domain.

Coa residues 467-491 showed 38% and 44% identity to the complement binding domain of sbi protein of *S. pseudintermedius* and *S. aureus* respectively with R470, N 478 and 7 linker amino acids in between consistent with the results of functional binding assays (ELISA and western blot) performed in this study. However, secreted Coa protein is not known to interact directly with the bacterial surface but can induce the formation of an Fg shield at some distance from the bacterial surface.

In this study, using flow cytometry, we showed another novel mechanism that allows secreted *S. pseudintermedius* Coa to localize at the cell surface of *S. pseudintermedius* by binding to surface-bound IgG and C3 and the attachment of soluble Fg to the bacterial surface creating a protective fibrinogen shield. It is likely that at least some of the Fg molecules are converted to fibrin through the action of Coa activated prothrombin. This effect is not only specific for *S. pseudintermedius* but also extends to protect other microorganisms, as demonstrated with *S. epidermidius*.

In this study we demonstrated that *S. pseudintermedius* coagulase effectively blocks phagocytosis of bacteria with addition of rabbit plasma and dog whole blood and the decrease of the percentage of phagocytosis is dose dependent on the concentration of the added coagulase. The gene targeted in this study encodes a novel *S. pseudintermedius* protein that displays coagulase activity, binds immunoglobulin and complement C3, and provides protection from phagocytosis. It is proposed as a good candidate for a vaccine to protect against disease caused by this organism.

Example 3—Nontoxigenic Protein A from *Staphylococcus pseudintermedius*

*S. pseudintermedius* expresses protein A on its surface and secretes it during the exponential growth phase. Phagocytosis experiments with *S. pseudintermedius* showed that blocking of protein A enhanced phagocytosis in whole blood, neutrophils and in a DH82 canine macrophage-like cell line. Taken together, the results demonstrate that *S. pseudintermedius* produces protein A that binds the Fc region of immunoglobulins and may serve as a potential virulence factor by evading the host immune system.

The purpose of this study was to characterize the cytotoxic effect of recombinant *S. pseudintermedius* Protein A (SpsQ) on dog B cells, develop attenuated SpsQ (SpsQ-M), and evaluate antibody raised against SpsQ-M in clinically healthy dogs. *Staphylococcus pseudintermedius* SpsQ-M was tested for its antigenicity and B cell killing. The results from this study suggest that *S. pseudintermedius* SpsQ may serve as a key component in a vaccine or as part of an immunotherapeutic treatment.

Materials and Methods

Bioinformatics Analysis

MSA of spsQ from diverse isolates of *S. pseudintermedius* (n=100), was performed using Geneious, version 9.1.3. The bacterial localization prediction tool, PSORTb version 3.0.2 (psort.org/psortb), was used to determine the topology and domain structure of SpsQ and SpsP. SpsQ modeling and binding site prediction were performed using Protein Homology/analogY Recognition Engine V 2.0 (Phyre$^2$) (sbg.bio.ic.ac.uk/phyre2), and the 3DLigandSite (sbg.bio.ic.ac.uk/3dligandsite), using SpA as a basis to predict the IgBDs in each domain. A pairwise sequence alignment of SpsQ and SpsP was used to identify conserved amino acids critical for IgG Fc and B cell receptor binding.

Identification of IgBDs was guided by *S. aureus* SpA secondary structure and based on *S. aureus* SpA residues responsible for dual reactivity of each domain in SpA with Fcγ and Fab and shared by *S. pseudintermedius* SpsQ.

Geneious, version 9.1.3 was used to select the locations for amino acids to be substituted in each IgBD and to design a full-length, four domain (SpsQ-M) attenuated *S. pseudintermedius* protein A construct (SpsQ-M). Glutamine (Q) 5 and 6, as well as aspartate (D) 32 and 33 in each domain of SpsQ were selected as critical amino acids for the association of SpsQ with immunoglobulin. To test this, substitutions of Q5K (lysine), Q6K, D32A (alanine), and D33A were introduced into each IgBDs of SpsQ.

Bacterial Strains and Growth Conditions

The *S. pseudintermedius* strain used in this study, strain 06-3228, was isolated at the University of Tennessee, College of Veterinary Medicine Bacteriology Laboratory. It represents the most common multilocus sequence type (ST) previously reported in the United States (ST68). Bacterial colonies grown on blood agar plates were inoculated into 5 ml of sterile trypticase soy broth (TSB) (BD Biosciences, San Jose, Calif., USA Cat No. RS1-011-21) and incubated overnight at 37° C. with shaking at 225 rpm (Excella E24 Incubator Shaker, New Brunswick Scientific). Fifty microliters of overnight culture were inoculated into 5 ml of fresh, sterile TSB to initiate log-phase bacterial cultures. Bacteria were grown at 37° C. with shaking at 225 rpm until an optical density of $OD_{600}$=0.4-0.6 was reached.

Cloning, Expression, and Purification of Recombinant Wild-Type and Non-Toxigenic *S. pseudintermedius* SpsQ Bacteria from a single colony of *S. pseudintermedius* strain 06-3228 obtained from blood agar plates were grown in TSB at 37° C. with 225 rpm shaking. DNA was extracted using a MO BIO UltraClean® Microbial DNA Isolation Kit (QIAGEN Inc., USA Cat No. 12224-50) according to the manufacturer's instructions. Oligonucleotide primers (Integrated DNA Technology, Coralville, USA) (Table 5) were designed using a PrimerQuest Tool (idtdna.com/PrimerQuest/Home/Index) based on the whole genomic sequence of *S. pseudintermedius* strain 06-3228 that we determined.

TABLE 5

Primers used to amplify recombinant wild and attenuated protein A (SpsQ) from Staphylococcus pseudintermedius (NotI and BamHI restriction sites are underlined).

| |
|---|
| Native full length spsQ forward<br>GCATGAGGATCCAAGTTTCGCAGAAGAAGGAGATA |
| Native full length spsQ reverse<br>GCATGAGCGGCCGCACCGAATAATGCCATATCGTTT |
| Attenuated full length spsQ forward<br>GCATGAGGATCCAAGTTTCGCAGAAGAAGGAGATA |
| Attenuated full length spsQ reverse<br>GCATGAGCGGCCGCACCGAATAATGCCATATCGTTT |

The spsQ open reading frame (ORF) without the regions encoding the predicted N-terminal signal peptide was amplified from *S. pseudintermedius* 06-3228 genomic DNA. The ORF of spsQ-M was amplified from a PMA-SpsQ-M plasmid (Table 6) (Life Technologies Corp., Carlsbad, Calif., USA), containing a synthetic spsQ-M gene. PCR was performed using taq polymerase (rTaq, Takara, USA Cat No. R004) and the following cycling conditions were performed: initial denaturation at 95° C. for 90 seconds, 30 cycles of denaturation at 94° C. for 30 seconds, annealing at 55° C. for 30 seconds, and extension at 72° C. for 1 minute followed by a final extension at 72° C. for 5 minutes. All ORFs were amplified without a 6× histidine tag because pETBlue-2 (Table 6) allowed T7lac promoter-based expression of target genes with C-terminal histidine •Tag® sequences. PCR products were Sanger sequenced at The University of Tennessee Genomics Core facility.

TABLE 6

Plasmids and competent cells used to clone and express recombinant wild and attenuated protein A (SpsQ) from *Staphylococcus pseudintermedius.*

| Plasmid/Bacteria | Expressed Gene |
|---|---|
| PMA-spsQ-M | Contain attenuated full length *S. pseudintermedius* protein A (SpsQ-M) |
| pETBlue-2 | SpsQ and SpsQ-M expression with blue/white screening and C-terminal HSV•Tag ® and His•Tag ® sequences |
| Dh5-alpha Tuner ™ (DE3) pLacI | Cloning and recombinant SpsQ and SpsQ-M protein expression |

To clone full length *S. pseudintermedius* spsQ and spsQ-M, the PCR products were digested with Nod and BamHI, then ligated into pETBlue-2, an expression vector with C-terminal HSV•Tag® and His•Tag® sequences (Novagen, USA Cat No 0.70674). The pETBlue-2 construct transformed into DH5-alpha *E. coli* chemically-competent cells (Table 6) (New England BioLabs Inc., USA Cat No. C2987I) by heat shock and DH5-alpha bacteria were plated on LB agar plates with 100 μg/mL ampicillin. The plasmid constructs were transformed into Tuner™ (DE3) pLacI *E. coli* chemically-competent cells (Table 6) (Novagen, USA Cat No 0.70623) by heat shock and the bacteria were plated on LB agar containing 50 μg/ml ampicillin and 20 μg/ml chloramphenicol.

To express recombinant protein, a single colony of Tuner™ (DE3) pLacI *E. coli* was inoculated into LB broth containing 50 μg/ml ampicillin and 20 μg/ml chloramphenicol and bacteria were grown overnight at 37° C. with 225 rpm shaking. LB broth containing 50 μg/ml ampicillin and 20 μg/ml chloramphenicol was inoculated with a 1:100 dilution of overnight culture and grown at 37° C. with 225 rpm shaking until a 600 nm optical density between 0.4 and 0.6 was reached. Protein expression was induced by addition of 1 mM Isopropyl β-D-1-thiogalactopyranoside (IPTG) (Teknova, USA Cat. No. I3431) and bacteria were grown for 4 h at 30° C. with shaking at 225 rpm. Bacterial cultures were centrifuged at 12,000×g for 5 min in 5 ml of protein extraction reagent (BugBuster, Novagen, USA Cat No. 70584) and 20 μl of 100× protease inhibitor (Cocktail Set III, EDTA-Free Calbiochem, USA Cat No. 539134), and subsequently incubated for 30 min at 37° C. in a shaking incubator at 225 rpm. Bacteria were pelleted by centrifugation at 12,000×g for 45 min at 4° C. Recombinant protein was purified from the supernatant using affinity purification (HisPur™ Ni-NTA Spin Purification Kit, Thermo Scientific, USA Cat No. 88228). Protein concentrations were determined using a bicinchoninic acid (BCA) assay (Thermo Scientific, USA Cat No. 23227).

Production of Antibodies Against Recombinant Proteins

Recombinant SpsQ-M (SEQ ID NO:2) at 100 μg/0.5 cc in phosphate buffered saline (PBS) (pH 7.2) was injected in the lateral thorax by the subcutaneous route, into three clinically normal dogs. Injections were given once every 7 days for a total of three injections with a control dog receiving PBS (pH 7.2) only. Blood (6 cc) was collected from a jugular vein using a 20 g needle and 12 cc syringe 4 times, on days −7, 8, 15 and 29. The collected blood was left undisturbed at room temperature for 30 min followed by centrifugation at 2,000×g for 10 min in a refrigerated centrifuge.

SDS-PAGE and Western Blots

Protein samples were resolved by SDS-PAGE in 4-12% polyacrylamide gels (Invitrogen, USA Cat No. NP0322BOX) and electrophoretically transferred onto nitrocellulose membranes (Thermo Scientific, USA Cat No. 77010). The blots were blocked overnight in 5% (w/v) nonfat dried milk powder dissolved in phosphate buffered saline containing 0.05% polyethylene glycol sorbitan monolaurate (Tween 20) (PBS-T) at 4° C. The blocked membranes were incubated with a 1:2,000 dilution of horseradish peroxidase (HRP)-conjugated anti-6×his tag monoclonal antibody (Thermo Scientific, USA Cat No. MA1-21315-HRP) in 0.05% PBS-T for 1 h with 225 rpm shaking at room temperature. After five washes with 0.05% PBS-T, bound antibodies were detected using 1-Step™ chloronaphthol substrate solution (Thermo Scientific, USA Cat No. 34012).

Enzyme-Linked Immunosorbent Assay

For measurement of the antigenicity of recombinant proteins, affinity-purified SpsQ and SpsQ-M were coated on ELISA plates (Corning, USA Cat No. 3590) at 2 μg/ml in PBS (pH 7.2). The plates were washed with PBS-T and incubated with HRP-chicken anti-protein A antibody (Gallus Immunotech, USA Cat No. APA) for 1 h at 37° C., then washed. For this and all subsequent ELISA assays, plates were washed three times with PBS-T between all incubations, bound antibodies were detected using TMB substrate (Thermo Scientific, USA Cat No. N301), reactions were stopped with 0.18 M sulphuric acid and optical density read at 450 nm on a plate reader (Bio TEK, USA Cat No. EL800). The experiment was repeated at least three times and a p-value of $<0.05$ was considered significant, which was the same for all the experiments unless mentioned otherwise.

To test the reactivity of serum from a dog with chronic pyoderma, *S. aureus* SpA and *S. pseudintermedius* SpsQ and SpsQ-M were coated on ELISA plates (Corning, USA Cat No. 3590) at 2 μg/ml in PBS. They were incubated with serum at a dilution of 1:2000. Bound IgG, IgM, and IgA were detected by HRP-goat anti-dog IgG-heavy and light chain (Bethyl Laboratories, Inc., USA Cat No. A40-123-1), HRP-goat anti-dog IgM μ chain (Bethyl Laboratories, Inc., USA Cat No. A40-116-2), HRP-goat anti-dog IgA (Bethyl Laboratories, Inc., USA Cat No. A40-104P) at a dilution of 1:8000 in PBS-T. Dog whole IgG molecule (Rockland, USA Cat No. 004-0102-1000) was used for comparison to measure non-specific IgG binding.

To detect a specific antibody response against SpsQ-M in injected dogs, recombinant *S. pseudintermedius* proteins and commercial SpA were coated on ELISA plates as previously described and incubated with two-fold serially diluted serum from injected dogs (1/1000-1/32000). Bound IgG was detected using HRP-goat anti-dog IgG-heavy and light chain (Bethyl Laboratories, Inc., USA Cat No. A40-123-1) with serum from uninjected dogs used as negative controls. The experiment was run in duplicate and a p-value of $<0.05$ was considered significant.

The Ability of *S. pseudintermedius* SpsQ to Kill B Cells and Induce B Cell Apoptosis A total of 100 μg of purified recombinant SpsQ or SpsQ-M was mixed with isolated peripheral blood mononuclear cells (PBMC) in 1 ml of RPMI medium supplemented with 10% fetal bovine serum and incubated for 1.5 h at 37° C. in a 5% $CO_2$ incubator. To detect early phases of B cell apoptosis, phosphatidylserine was measured on the surface of cells using pacific blue-conjugated annexin (Thermo Scientific, USA Cat No. A35136). B cells were identified using phycoerythrin (PE) conjugated mouse anti-canine CD21 (clone: CA2.1D6) (BIO-RAD, USA Cat No. MCA1781PE) that recognizes canine CD21 (complement receptor type 2) on mature B lymphocytes. Stained B cells were analyzed using a flow cytometer (Attune acoustic focusing cytometer). B cells were also incubated with the same recombinant proteins as described above but for 3.5 h in order to detect B cell death. Cells were stained with Sytox green (Life Technologies, Inc., USA Cat No. 1776406) and PE-conjugated mouse anti-canine CD21. Gates were placed on cells positive for PE and these B cells were analyzed by flow cytometry.

To determine the protective effect of canine anti-SpsQ-M on B cells, recombinant *S. pseudintermedius* SpsQ was incubated for 30 minutes at 37° C. with serum from SpsQ-M injected dogs. The experiment was run in duplicate and a p-value of $<0.05$ was considered significant.

For flow cytometry analysis the cut-off for apoptosis or cell death was established using leukocytes incubated without SpsQ. Mean fluorescent intensity was determined from all B cells.

Statistical Analysis

A one-way ANOVA and Tukey-Kramer method were used to measure the significant differences between SpsQ, SpsQ-M, and SpA on inducing apoptosis and causing B cell death. However, two-way ANOVA and Tukey-Kramer methods were performed to test if there were significant differences in SpA, SpsQ or SpsQ-M binding with canine antibodies. All analyses were conducted using the GraphPad Prism software (Version 7, GraphPad Software Inc.).

Results

Bioinformatics Analysis and *S. pseudintermedius* Protein A Characteristics

Figure 9:
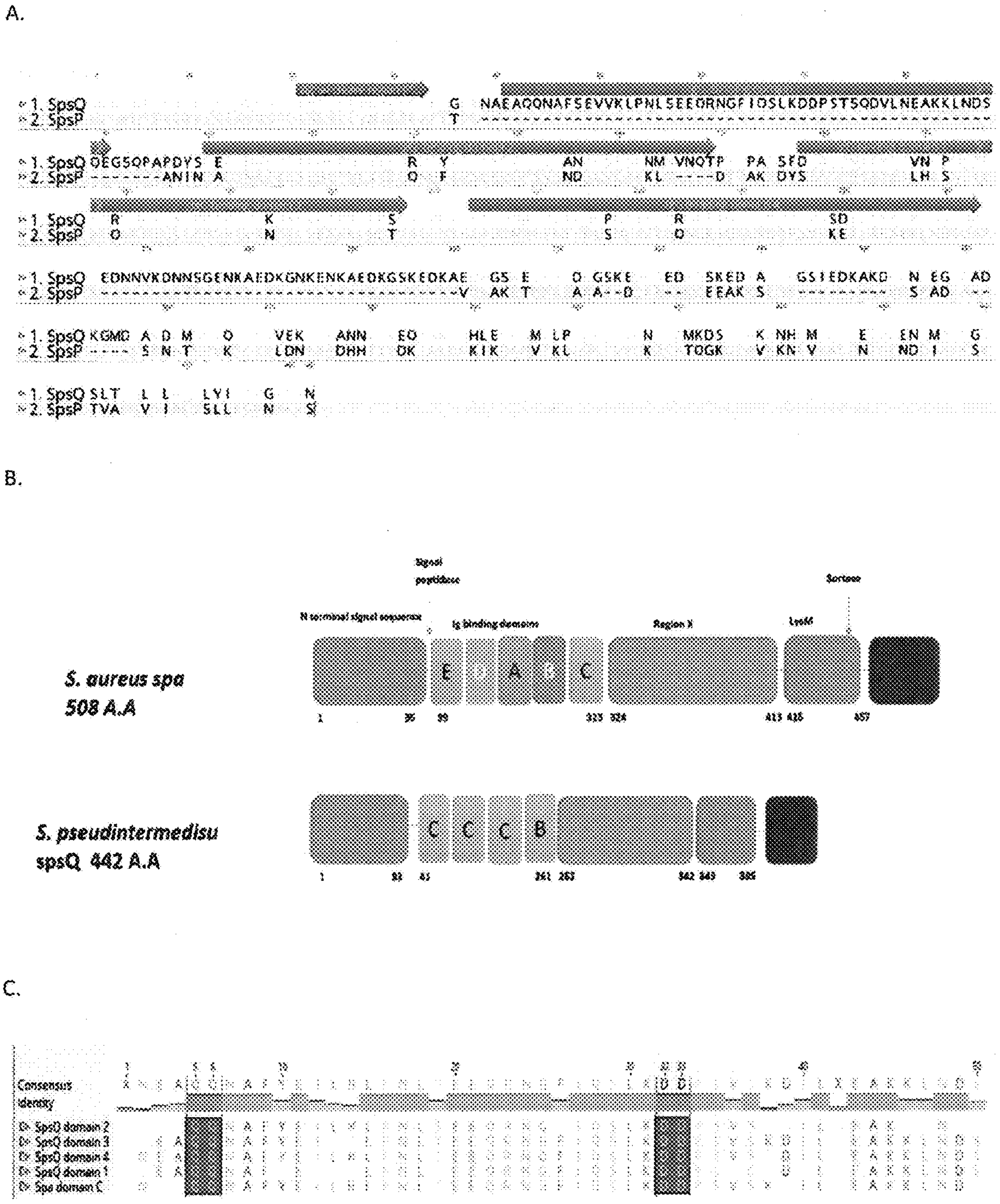
FIG. 9: *S. pseudintermedius* SpsQ characteristics and basis for generation of recombinant nontoxigenic protein A (SpsQ-M). A. pairwise alignment between *S. pseudintermedius* ED99 SpsQ and SpsP. B. SpA of *S. aureus* subsp. *Aureus* strain Newman and SpsQ of *S. pseudintermedius* harbors an N-terminal signal peptide (orange boxes), Ig binding domains, 13 variable region X (grey boxes), LysM sequence (green boxes) and C-terminal sorting signal 14 (black boxes). C. Amino acid sequences of the four Ig binding domains of SpsQ, as well as Ig binding domain C of SpA, with the positions glutamine (Q, highlighted in blue) 5 and 6 and 16 aspartate (D, blue highlight) 32 and 33 as indicated. D. SpsQ secondary structure composition. 17 SpsQ is composed of alpha helices with the positions of triple α-helical bundles shown for each 18 domain.
Figure 9:
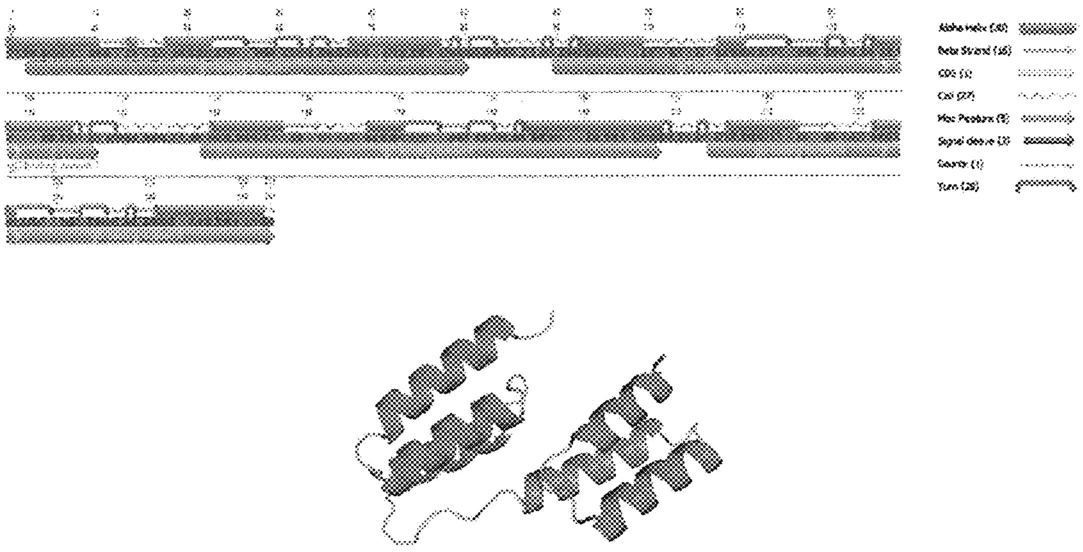

*S. pseudintermedius* ED99, represents isolates that have genes encoding both SpsQ and SpsP. SpsQ contained four and SpsP had genes encoding a maximum of three Ig-binding domains (FIG. 9A). This compares to five domains with AA identities of 74% in *S. aureus* subsp. *aureus* strain Newman SpA (FIG. 9B). Three out of four SpsQ domains share 84-88% identity with the C domain of *S. aureus* SpA with threonine at position 19, while only one domain is more similar to the B domain of *S. aureus* SpA (FIG. 9C).

Multiple sequence alignment (MSA) between each domain of SpsQ and domain C of SpA, the most similar domain to SpsQ IgBDs, showed that each domain in SpsQ has binding sites for the IgG Fcγ (Glutamine $(Q)_5$ and $Q_6$), and Fab region (aspartate $(D)_{32}$ and $D_{33}$) of surface membrane-associated variable heavy 1 (VH1)-encoded B cell antigen receptors (FIG. 9C). Furthermore, as with SpA of *S. aureus*, the secondary structure of SpsQ consists only of alpha helices and each Ig binding domain consists of three helices (FIG. 9D).

Cloning, Expression, and Purification of Recombinant SpsQ and SpsQ-M

Recombinant polyhistidine tagged SpsQ and SpsQ-M were produced in *E. coli* and purified using HisPur Ni-NTA resin under native conditions and eluted using an imidazole gradient. The molecular weights of SpsQ and SpsQ-M determined in western blots were of the expected sizes (47.2 and 47.6 kDa, respectively) (data not shown).

Figure 10:
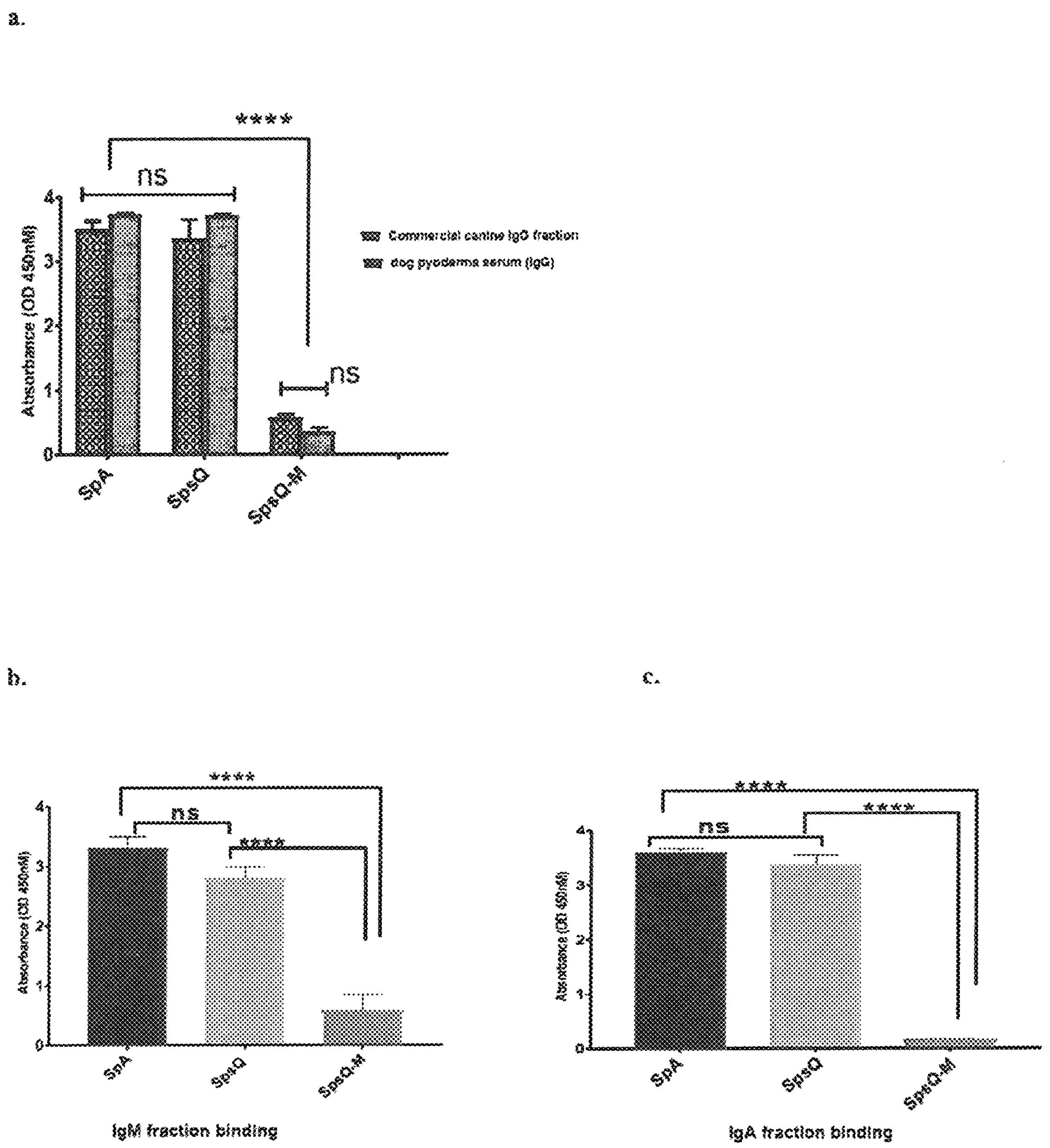
FIG. 10. Natural infection with *S. pseudintermedius* did not elicit antibody specifically reactive with staphylococcal protein A. Serum from a dog with a history of chronic pyoderma showed significantly lower reactivity with SpsQ-M compared to wild type SpsQ and SpA for (A) IgG; (B) IgM; and (C) IgA (p-value of 0.0001 for each; P<0.05 considered significant; ns=not significant).

Antigenicity of SpsQ and SpsQ-M and their Reactivity with Serum from a Dog with Pyoderma Chicken anti-protein A, chosen because protein A does not bind chicken immunoglobulin, had strong reactivity with affinity-purified SpsQ-M similar to that with *S. aureus* SpA and *S. pseudintermedius* SpsQ, indicating the attenuated protein retained its antigenicity (data not shown). Sera from a dog with a history of chronic pyoderma showed significantly lower reactivity against SpsQ-M (FIG. 10A) compared to recombinant wild-type SpsQ and SpA. SpsQ-M had significantly lower binding (p-value of 0.0001) to commercial dog IgG (FIG. 10A), IgM (p-value of 0.0001) (FIG. 10B) or IgA (p-value of 0.0001) compared to SpsQ and SpA. (FIG. 10C).

*S. pseudintermedius* Protein a Induced Apoptosis of Canine B Cells

Figure 11:
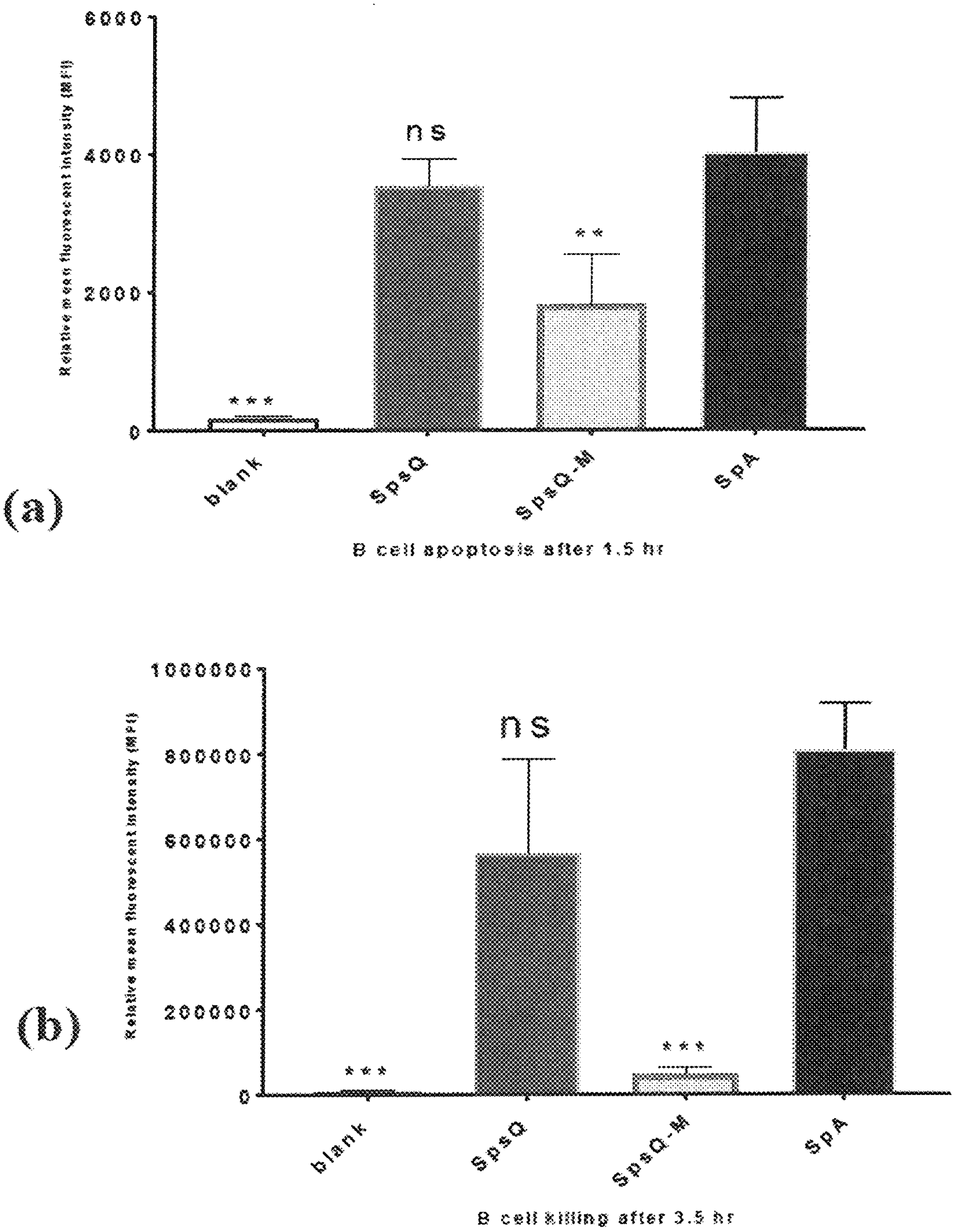
FIG. 11: *S. pseudintermedius* recombinant SpsQ has a superantigenic effect on canine B cells. A) gating on canine peripheral blood mononuclear cells (PBMC). B) gating on canine B cells using PE-anti-CD21 antibody. Results shown as mean fluorescent intensity (MFI) of the blank, SpsQ, and SpsQ-M relative to SpA calculated based on average values from three independent experiments (P<0.05 considered significant; ns=not significant). MFI of SpsQ-M was significantly lower (P=0.0003) than that of SpsQ and SpA.

Affinity-purified SpsQ-M had a low apoptotic effect on B cells at 1.5 h in contrast to recombinant SpsQ at the same time point, with a mean+/−SEM fluorescent intensity (MFI) difference of 2052±285.2 between SpsQ and SpsQ-M (p-value of 0.0063) (FIG. 11A). Incubation of the cells for 3.5 h with SpsQ-M resulted in a Sytox MFI reduction of 519065±128292 SEM compared to that of SpsQ (p-value of 0.0003) (FIG. 11B).

SpsQ-M Induces Specific Antibody Responses in Dogs that Reduce the Effect of SpsQ on B Cells In Vitro ELISA analysis of sera obtained from dogs on days −7, 8, 15 and 29 (relative to injections) showed that antibodies against *S. pseudintermedius* SpsQ-M and SpsQ were detected on day 15 and reached the highest level on day 29 ($P<0.0001$) compared to pre-injection control sera (FIGS. 12A-12B).

Figure 13:
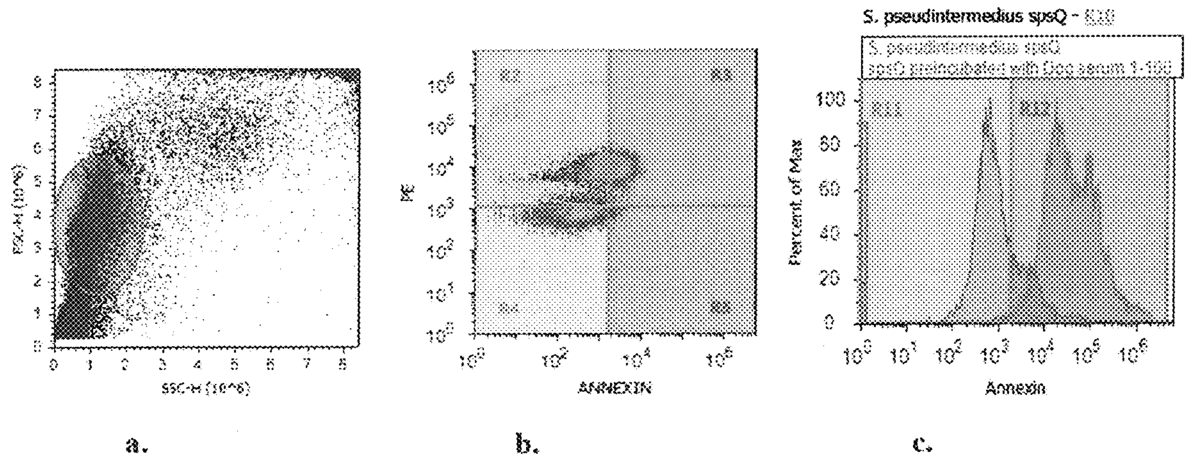
FIG. 13: Dog anti-SpsQ-M antibody protects canine B cells from the superantigenic effects of SpsQ. Preincubation of SpsQ with dog anti-SpsQ-M resulted in mean 105,665±900.3, n=1 reduction in MFI from SpsQ on canine B cells compared to SpsQ treatment alone. A) gating on canine PBMC based on side and forward scatter. B) gating on B cells using PE-anti-CD21 antibody. C) SpsQ induced B cell apoptosis after 1.5 hr (red peak) compared to SpsQ preincubated with dog serum at dilution 1:100 (blue peak).

Pre-incubation of SpsQ, at a concentration of 100 μg/ml in PBS with dog anti-SpsQ-M resulted in 105665±900.3 SEM, n=1 reduction in annexin mean fluorescent intensity (MFI) as compared with that of SpsQ treatment alone (FIGS. 13A-13C).

DISCUSSION

Protective host immune responses against extracellular pathogens are typically antibody-mediated. Unfortunately, staphylococcal infection does not usually establish protective immunity and efficacious staphylococcal vaccines have proven difficult to develop. Most vaccine research has focused on *S. aureus*, which most commonly affects humans and is distinguished from *S. pseudintermedius*, which is primarily of veterinary concern.

*S. pseudintermedius* SpsQ binding with the Fab region of surface membrane-associated VH1-encoded B-cell antigen receptors induces apoptosis in canine B cells. We developed a non-toxigenic SpsQ (SpsQ-M; SEQ ID NO:2) by substitution of residues responsible for dual reactivity of each SpsQ domain with IgG Fcγ and Fab regions of surface membrane-associated VH1-encoded B-cell antigen receptors. Compared to staphylococcal protein A, SpsQ-M had much lower reactivity with IgG. Moreover, IgG, IgM, and IgA in sera from a dog with a history of chronic pyoderma had little immune-mediated binding to SpsQ-M indicating a lack of natural production of antibody elicited by infection with *S. pseudintermedius*. Comparing purified recombinant wild-type and mutant SpsQ, we found SpsQ-M had a significantly lower toxic effect on canine B lymphocytes.

It should be noted that specific antibody directed against native protein A cannot be measured due to the non-immune binding of protein A to immunoglobulin. After injecting a clinically healthy dog with SpsQ-M, we observed a high titer of SpsQ-specific antibodies. These results indicate that SpsQ, similar to SpA, suppresses adaptive immune responses during staphylococcal infection which may explain why previous *S. pseudintermedius* infections are not associated with protective immunity against recurrent infection. Dog anti-SpsQ-M abolished the superantigenic effect of SpsQ that triggers apoptotic cell death in canine B cells.

Example 4—*Staphylococcus pseudintermedius* Adenosine Synthase (SpAdsA)

In this study is reported the identification of a novel cell wall-anchored 5'-nucleotidase in *S. pseudintermedius* (SpAdsA) that has no more than 52% identity with other bacterial adenosine synthase genes but which contains conserved functional domains. Furthermore we show that *S. pseudintermedius* uses adenosine synthase anchored on the cell wall to synthesize adenosine that suppresses the canine innate immune response and facilitates its survival.

Materials and Methods

Bacterial Strains and Plasmids

The *S. pseudintermedius* strains used in this study were as previously discussed, representing the most common sequence types (ST) in the United States, included 06-3228 (ST68), 08-1661 (ST71) and NA45 (ST84).

Plasmid construct pMA-RQ-Bs-M $Ado_{370-1868}$, containing a mutated synthetic *S. pseudintermedius* SpAdsA gene with BamHI/NotI cloning sites was obtained commercially (Invitrogen™ GeneArt™ Gene Synthesis—Thermo Fisher Scientific).

Bioinformatics Analysis and *S. pseudintermedius* 5'-Nucleotidase Characteristics A rooted phylogenetic tree (UPGMA, unweighted pair group method with arithmetic mean) of 5'-nucleotidases was generated with Geneious version 9.1.3 (28) using complete protein sequences of SpAdsA (*S. pseudintermedius* 08-1661, ANS88668.1), S5 nA (*S. pyogenes*, AAK33792)(29), AdsA (*S. aureus*, ESR29110)(11), Ssads (*S. suis*, YP001197640)

(14), 5'-nucleotidases (*Staphylococcus* delphini, WP_096556274.1), 5'-nucleotidases (*Enterococcus faecalis*, WP_010714156.1) and 5 '-nucleotidases (*Staphylococcus intermedius* WP_086428047.1). Multiple sequence alignment of *S. pseudintermedius* 5'-nucleotidase proteins was performed using Geneious version 9.1.3. The bacterial localization prediction tool, PSORTb version 3.0.2 (available at psort.org/psortb/) was used to predict the protein topology and domain structure of SpAdsA. Protein modeling and binding site prediction was performed using Phyre2 web portal (available at sbg.bio.ic.ac.uk/phyre2/) and 3DLigandSite (available at sbg.bio.ic.ac.uk/3dligandsite/).

Polymerase Chain Reaction (PCR) Amplification of the Wild and Mutant SpAdsA Gene from *S. pseudintermedius*

Bacteria from a single colony of *S. pseudintermedius* strain 08-1661 obtained from blood agar plates were grown in tryptic soy broth (TSB) (Becton, Dickinson and Co., Sparks, Md.) at 37° C. with 225 rpm shaking. DNA was extracted using MO BIO UltraClean® Microbial DNA Isolation Kit (QIAGEN Inc. Cat No. 12224-50) according to the manufacturer's instructions. Oligonucleotide primers with BamHI and NotI restriction sites (underlined) were designed using Geneious version 9.1.3 based on the complete genome sequence of *S. pseudintermedius* strain 08-1661.

Primers for the amplification of native SpAdsA were W-Ado-Forward: GCATGA <u>GGATCC</u>GAAACGACTGCAACGCATAC and W-Ado-Reverse: GCATGA <u>GCGGCCGCTC</u>CACCTGAAGCTGTAAAGTC. Primers for amplification of mutant SpAdsA were M-AdoForward: GCATGA <u>GGATCC</u>ATGTTAAGATTGTCGGCTAAAAAAG and M-AdoReverse: GCATGA <u>GCGGCCGC</u>TCCACCTGAAGCTGTAAAGTC.

The native SpAdsA open reading frame (ORF) (1539 bp) without the regions encoding the predicted N-terminal signal and C-terminal sortase anchoring sequence was amplified from 60 ng of genomic DNA of *S. pseudintermedius* 08-1661 by 35 cycles of PCR with rtaq polymerase (Takara, Cat No. R004) at an annealing temperature of 55° C. using primer W-Ado-Forward and W-Ado-reverse. The ORF of mutant SpAdsA (1536 bp) was excised from pMA-RQ-Bs-M Ado plasmid using BamHI-NotI restriction enzymes.

Cloning, Expression and Purification of Recombinant Wild and Mutant SpAdsA of *S. pseudintermedius* 08-1661

The PCR products of wild and mutant SpAdsA were digested with the restriction enzymes BamHI and Nod and purified using QuickClean II Plasmid Miniprep Kit (Genscript, Cat No. L00420) according to the manufacturer's instructions. Purified product was ligated into pETBlue™-2 (Novagen, Wis. USA), transformed into DH5-alpha *E. coli* and plated on LB agar plates with 100 µg/mL ampicillin, 80 µg/mL X-gal and 50 µM IPTG (Teknova, Cat No. L1925). For screening the clones containing recombinant plasmid, X-gal chromogenic substrate was added to the agar plates. The recombinant plasmid was extracted using GeneJET Plasmid Miniprep Kit according to the manufacturer's instructions (ThermoFisher, Cat No. K0502). The presence of the cloned fragment was confirmed by PCR. pETBlue™-2 constructs were transformed in Tuner™ (DE3) pLacI *E. coli* chemically-competent cells (Novagen, Cat No 0.70623) by heat shock and plated on LB agar containing 50 µg/ml ampicillin (Sigma-Aldrich, Cat No. A5354) and 20 µg/ml chloramphenicol (Sigma-Aldrich, Cat No. C0378). A single colony was used to inoculate LB broth containing 50 µg/ml ampicillin and 20 µg/ml chloramphenicol and the broth was incubated overnight at 37° C. with shaking at 225 rpm. Fresh LB medium containing 50 µg/ml ampicillin and 20 µg/ml chloramphenicol was inoculated at a 1:100 dilution and grown to an optical density of 0.6 at wavelength 600 nm then protein expression was induced by addition of 1 mM isopropyl β-D-1-thiogalatopyranoside (IPTG) for 4 hr at 30° C. with shaking at 225 rpm.

A suspension of IPTG-induced Tuner cell bacteria (100 ml) was centrifuged at 12000×g for 5 min. Bacteria were suspended in 5 ml of protein extraction reagent (BugBuster, Novagen Cat No. 70584) and 20 µl 100× Protease Inhibitor Cocktail Set III, EDTA-Free (Calbiochem, Cat No. 539134), incubated for 30 min at 37° C. in a shaking incubator at 225 rpm, and centrifuged at 12,000×g for 45 min at 4° C.

Recombinant protein was purified using a HisPur™ Ni-NTA Spin Purification Kit (Thermo Scientific, Cat No. 88228) according to the manufacturer's instructions. Protein concentrations were determined with the Pierce™ BCA Protein Assay Kit (Thermo Scientific, Cat No. 23225).

SDS-PAGE and Western Blot

Protein samples were resolved by SDS-PAGE in 4-12% polyacrylamide gels (Invitrogen, Cat No. NP0322BOX) and electrophoretically transferred onto a nitrocellulose membrane (Thermo Scientific, Cat No. 77010). The blots were blocked overnight in 5% (wt/vol) nonfat dried milk powder in 0.05% polyethylene glycol sorbitan monolaurate (Tween 20) containing phosphate buffered saline (PBS-T) at 4° C. The blocked membranes were incubated with a 1:2,000 dilution of horseradish peroxidase (HRP)-conjugated 6×his tag monoclonal antibody (Thermo Scientific, Cat No. MA1-21315-HRP) in 0.05% PBS-T for 1 h with 225 rpm shaking at room temperature. After five washes with 0.05% PBS-T bound antibodies were detected using 1-Step™ chloronaphthol substrate solution (Thermo Scientific, Cat No. 34012).

Adenosine Synthase Activity

Overnight cultures of *S. pseudintermedius* 06-3228 and 08-1661 were centrifuged and washed twice with phosphate buffer saline (PBS) and then suspended in 1 ml digestion buffer (0.6 M sucrose buffered with 50 mM Tris, pH 7.5) containing 200 µg trypsin from porcine pancreas (Sigma-Aldrich, Cat NO. T4799). Bacteria were digested with trypsin for 1.5 h at 37° C., then the supernatant containing *S. pseudintermedius* SpAdsA was obtained after centrifugation at 10,000×g for 5 minutes at 4° C. Four ml of *S. pseudintermedius* tryptic digest and recombinant SpAdsA protein at 0.15 µg/ml were suspended in 500 µL TM buffer (50 mM Tris-HCL [pH 7.5], 5 mM $MnCl_2$), then hydrolysis of ATP (Sigma-Aldrich, Cat NO. A26209) and AMP (Sigma-Aldrich, Cat NO. 01930) was carried out in the presence of 1 mM nucleotide at 37° C. for 15 minutes. Inorganic phosphate (IP) release was measured using a malachite green phosphate kit according to the manufacturer's protocol (Sigma-Aldrich, Cat NO. MAK307).

Bacterial Survival in Blood

Overnight cultures of *S. pseudintermedius* 06-3228 and 08-1661 were diluted 1:100 into fresh TSB and grown for 3 hours at 37° C. Staphylococci were centrifuged 9000×g, washed twice, and diluted in PBS to yield an O.D 600 of 0.5. Then 100 µl of $4\times10^6$ CFU per ml of bacteria were mixed with 500 µl of fresh canine blood, collected in EDTA. The samples were incubated at 37° C. with 100 rpm shaking and harvested at 60, 90 and 120 minutes. They were incubated on ice for 30 minutes in 1 ml of Red Blood Cell Lysing Buffer Hybri-Max™ (Sigma-Aldrich, Cat NO. R7757), then bacteria were pelleted at 9,000×g at 4° C. and plated on tryptic soy agar (TSA) for enumeration of viable bacteria.

Flow Cytometry Analysis

Bacteria for the phagocytosis assay were labeled using a pHrodo™ phagocytosis particle labeling kit (Life technologies, P35369) (10). Briefly, overnight cultures of *S. pseudintermedius* 06-3228 and 08-1661 were diluted 1:100 into fresh TSB and grown for 3 hours at 37° C. Bacteria were centrifuged, washed twice, and diluted to 20 mg/mL wet weight in 0.1 M sodium bicarbonate, pH 8.5, and pHrodo™ dye was dissolved in DMSO at 10 mM. The bacteria were suspended at a final dye concentration of 0.5 mM. The inhibitory effect of SpAdsA on canine neutrophils was evaluated in blood samples by exposing the EDTA-whole blood samples to pHrodo™ dye-labeled *S. pseudintermedius* 06-3228 and 08-1661 for 30 and 60 minutes at 37° C. The RBCs were lysed using Red Blood Cell Lysing Buffer Hybri-Max™ (Sigma-Aldrich, Cat NO. R7757) followed by centrifugation and washing. The final cell pellet, containing leukocytes, was suspended in wash buffer and analyzed using a flow cytometer equipped with a 488-nm argon ion laser (Attune acoustic focusing cytometry).

Statistical Analysis

Data were analyzed using general liner modes with treatment, protein and time as the independent variables while inorganic phosphate (IP) release, mean fluorescence intensity (MFI) and colony forming units per ml (CFU $ml^{-1}$) were used as response variables, respectively. Multiple comparisons were performed with Tukey's adjustment. Statistical significance was identified at the significant level of 0.05. Rank transformation on response variables were conducted when the normality assumption was violated. All analyses were conducted using PROC mixed in the SAS system for Windows version 9.4 (SAS Institute Inc., Cary, N.C.).

Results

Figure 14:
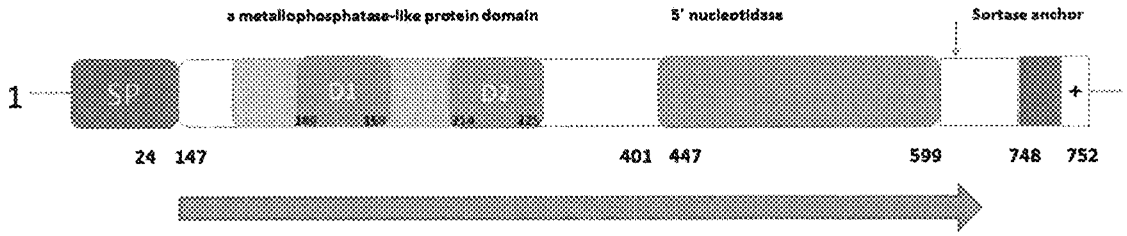
FIG. 14: *S. pseudintermedius* spAdsa structure and model. A) schematic diagram of *S. pseudintermedius* 08-1661 SpAdsa. The numbers at the bottom indicate amino acid positions. SP, signal peptide sequence. D1, first domain signature sequence, D2 second signature domain sequence. B) binding site prediction of aspartate at positions 154 and 189, histidine at 156, 318, 354, and 356 and asparagine at 221. C) 3D model of *S. pseudintermedius* spAdsa protein with amino acid substitutions with alanine to produce the mutant form.
Figure 14:
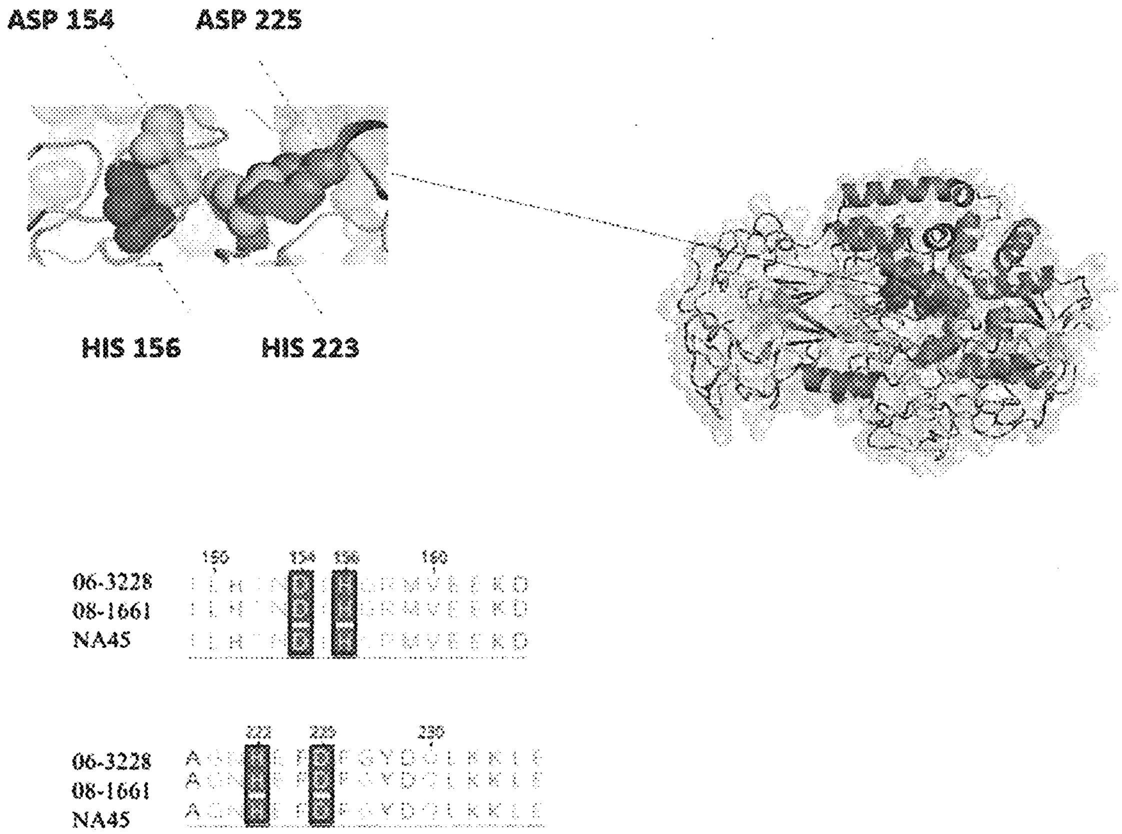

Bioinformatics Analysis and *S. pseudintermedius* 5'-Nucleotidase Characteristics Bioinformatic analysis of the predicted 780-amino acid sequence showed significant homologies to members of the 5'-nucleotidase/apyrase protein family (Interpro accession number: IPRO006179) with two characteristic domains. Dimetal-containing phosphoesterases (DMPs) (Interpro accession number: IPRO29052) are between position 147 and 401 with two domain signature sequences D1 and D2 (FIGS. 14A-14C) and a 5'-nucleotidase C-terminal domain (Interpro accession number: IPRO008334) is between positions 447 and 599 (FIGS. 14A-14C). Furthermore, the protein sequence contains a predicted N-terminal signal peptide sequence from positions 1 through 24 and a LPXTG cell wall anchor sequence between positions 748 and 752 (FIGS. 14A-14C).

A BLAST search of the GenBank database revealed related putative nucleotidases in other pathogenic bacterial species within the *Staphylococcus intermedius* group including *Staphylococcus delphini* (91% amino acid identity) and *Staphylococcus intermedius* (88% amino acid identity). Only limited sequence identity was found with *S. aureus* AdsA (52.4%), *Enterococcus fecalis* 5'-nucleotidase (36.0%), *S. pyogenes* S5 nA (20.1%) and *S. suis* Ssads (20.0%). No other species of bacteria with homologous proteins were identified in the database.

The Phre2 web tool was used to analyze SpAdsA based on the X-ray structure of *S. suis* type 2 5'-nucleotidase. Aspartic acids (positions 154 and 189), histidine (positions 156, 318, 354 and 356) and asparagine (position 221) within the SpAdsA signature sequences were predicted to be essential for divalent metal cation binding (FIGS. 14A-14C). Based on the previously reported bacterial nucleotidases produced by Gram-positive bacteria and our 3D model we predicted that aspartate (position 154 and 225) and histidine (position 156 and 223) are critical amino acids for enzyme activity. To confirm the function of these domains, aspartic acid and histidine were substituted at these positions in *S. pseudintermedius* 08-1661 SpAdsA referenced to Genbank accession No: ANS88668.1.

Cloning, Expression and Purification of Recombinant *S. pseudintermedius* SpAdsA SpAdsA is predicted to have an N-terminal signal sequence and C-terminal sortase anchoring domain. Recombinant SpAdsA proteins (SEQ ID NO:6) lacking those sites were produced to facilitate a study of the mature protein. The sizes of recombinant native and mutant SpAdsA were 55.8 kDa and 55.4 kDa respectively, as determined by western blot using monoclonal antibody directed against the HIS tag.

*S. pseudintermedius* 5'-Nucleotidase Synthesizes Adenosine

Figure 15:
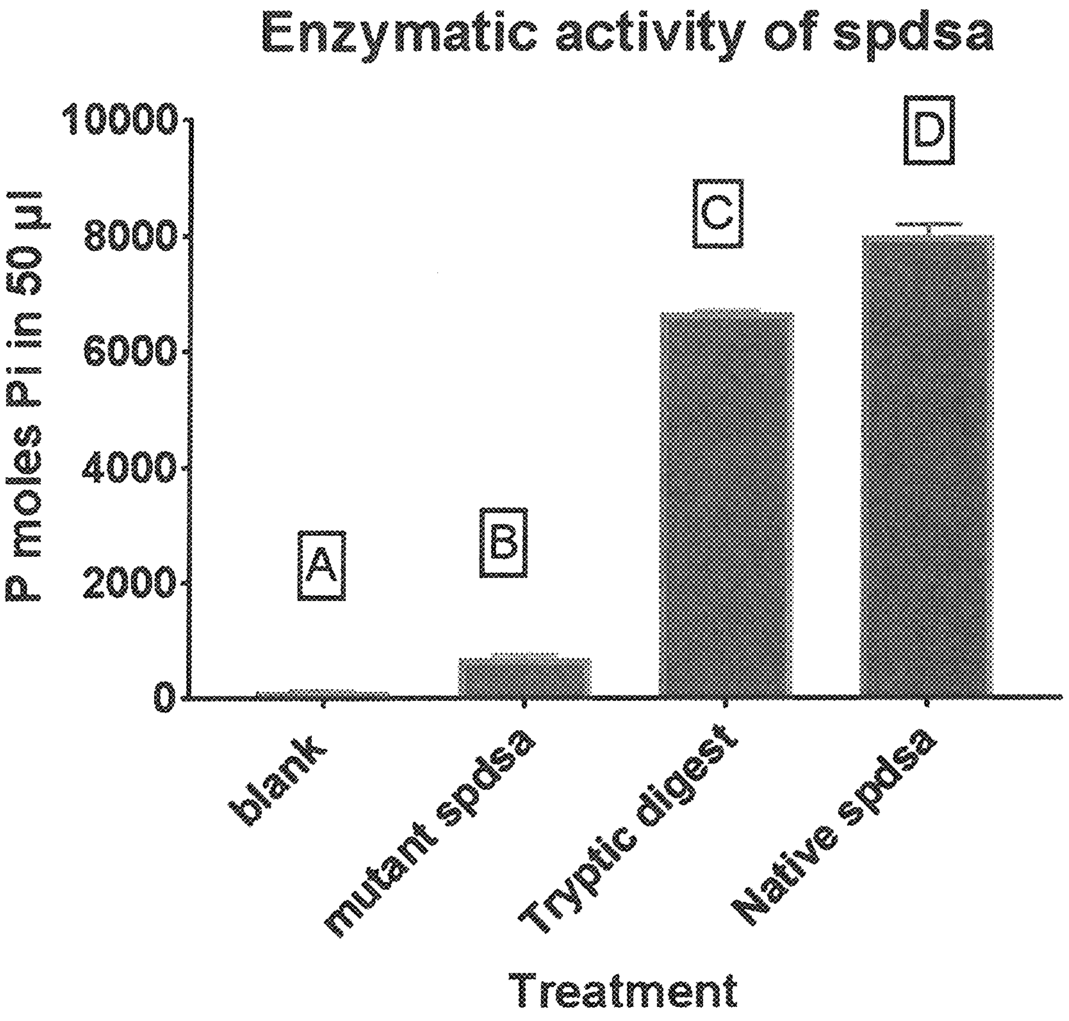
FIG. 15: Total release of inorganic phosphate (Pi) by 5' nucleotidase as well as 06-3228 tryptic digest in P moles from 50 μl of 1 mM ATP and AMP was significantly higher than that from the mutant 5' nucleotidase (P≤0.0001).

Tryptic digests of surface proteins of *S. pseudintermedius* 06-3228 showed hydrolytic activity that released adenosine from AMP and ATP (FIG. 15). Similar activity was obtained with recombinant SpAdsA which harbors a domain with the two signature sequences, ILHTNDIHGRM and YDAMTAGNHEFD. The total release of inorganic phosphate (Pi) by recombinant SpAdsA (mean Pi moles phosphate in 50 μl=7998.32) as well as 06-3228 tryptic digest (mean Pi moles phosphate in 50 μl=6688.42) from 50 μl of 1 mM ATP and AMP was significantly higher than that from the mutant protein (mean Pi moles phosphate in 50 μl=555.79) (p<=0.001) (FIG. 15). This suggests that the two signature sequences (D1 and D2) are critical for enzymatic activity in *S. pseudintermedius* similar to *S. suis* type 2. Together these results confirm that SpAdsA is capable of hydrolyzing ATP and AMP to produce adenosine.

SpAdsA Facilitates Survival of *S. pseudintermedius* in Canine Blood

Figure 16:
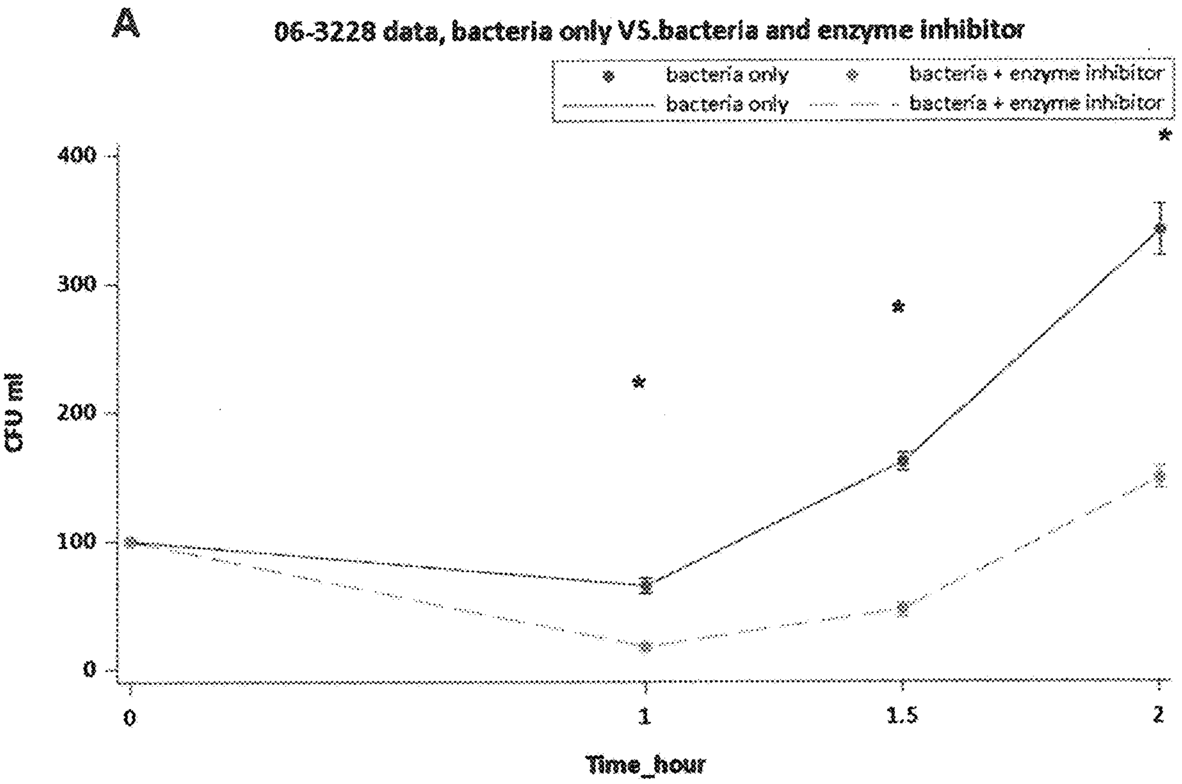
FIG. 16: Survival of *S. pseudintermedius* 06-3228 and 081661 in blood increased with addition of exogenous adenosine (C; F) while addition of 5'-(α,β-methylene) diphosphate (500 μM) (A; D), a 5' nucleotidase inhibitor as well as $A_{2A}$ receptor antagonist (B; E) diminished ability of staphylococci to escape phagocytic killing (n=3 per treatment; P≤0.0108 for 06-3228 and P≤0.0265 for 08-1661).
Figure 16:
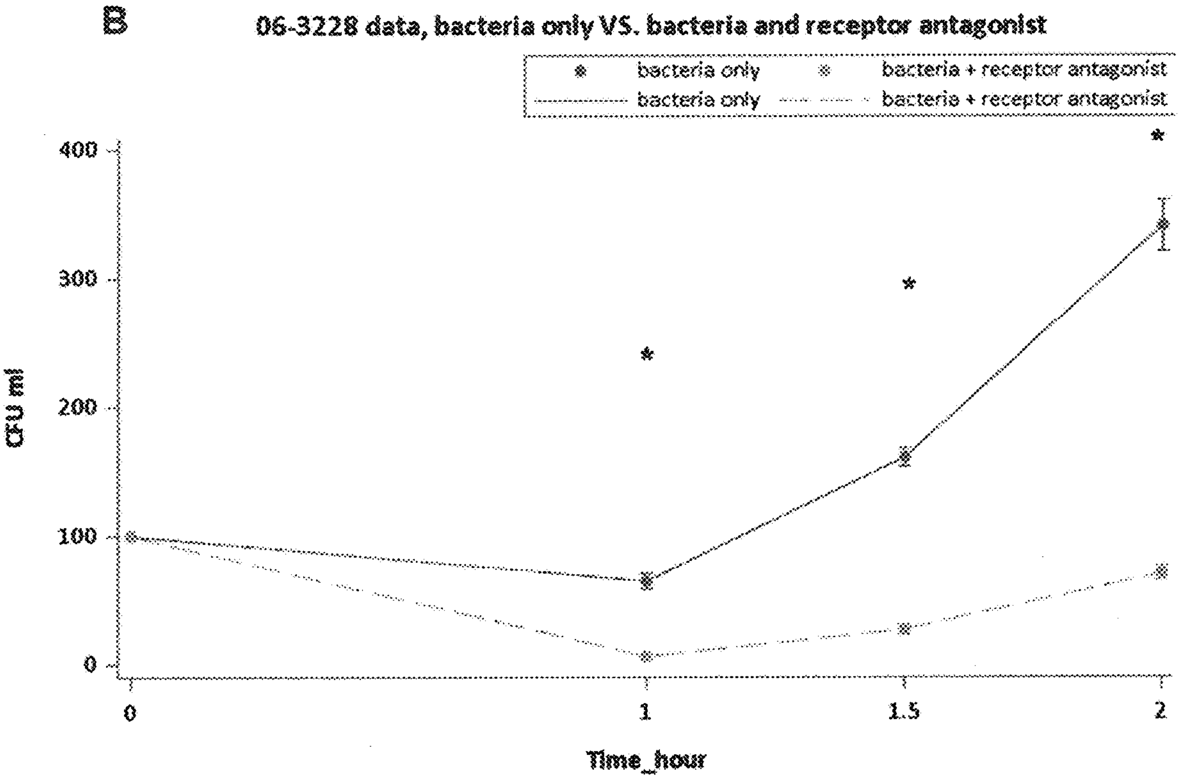
Figure 16:
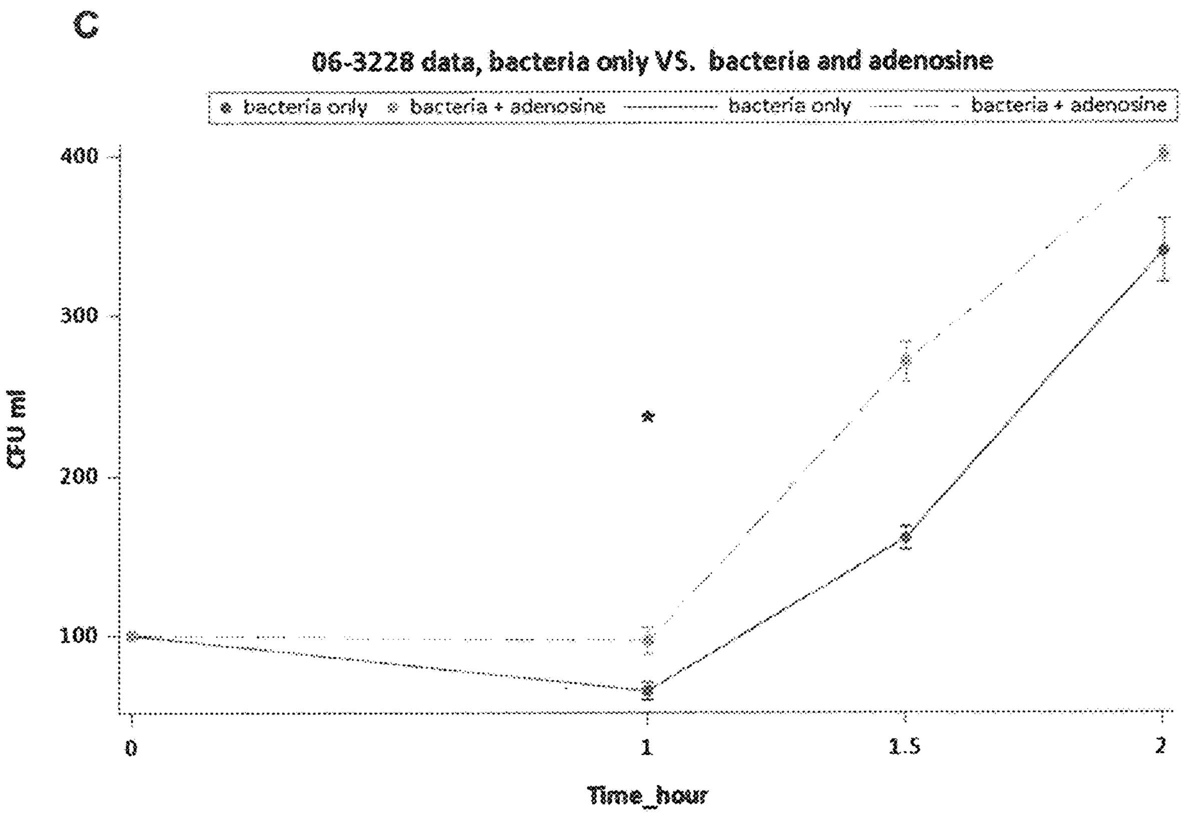
Figure 16:
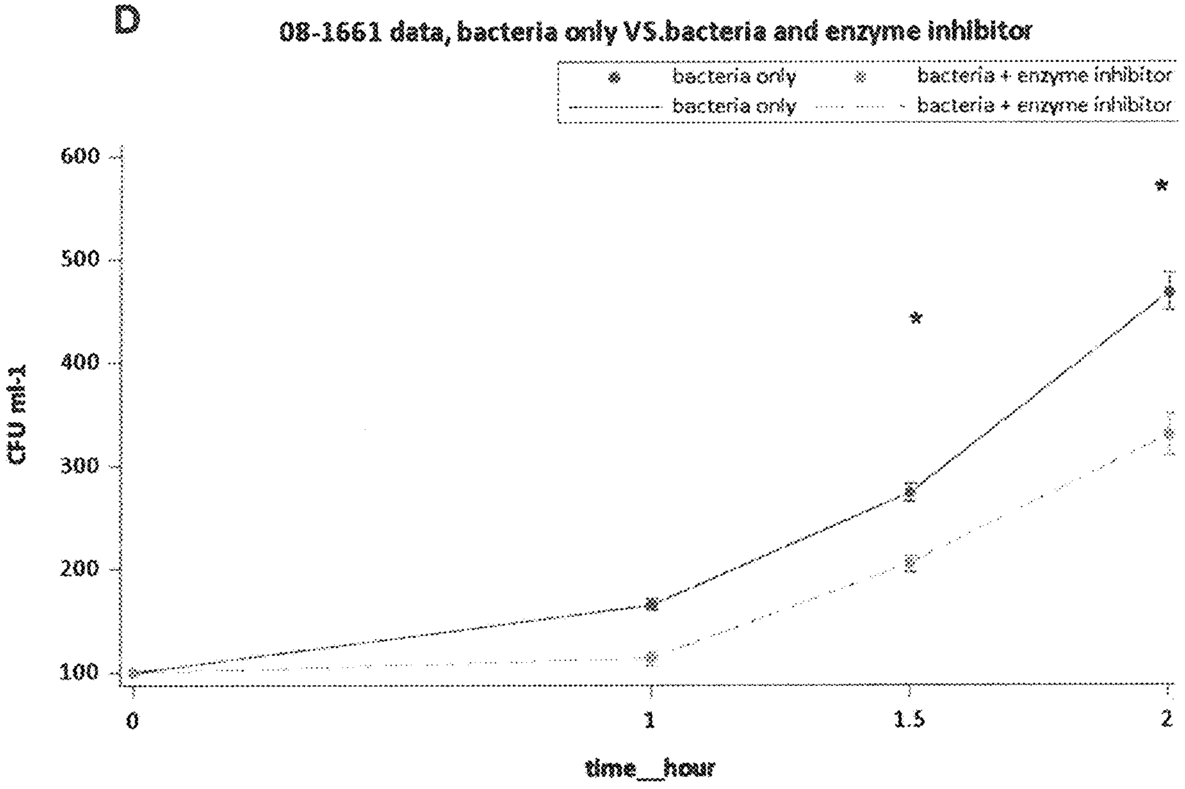
Figure 16:
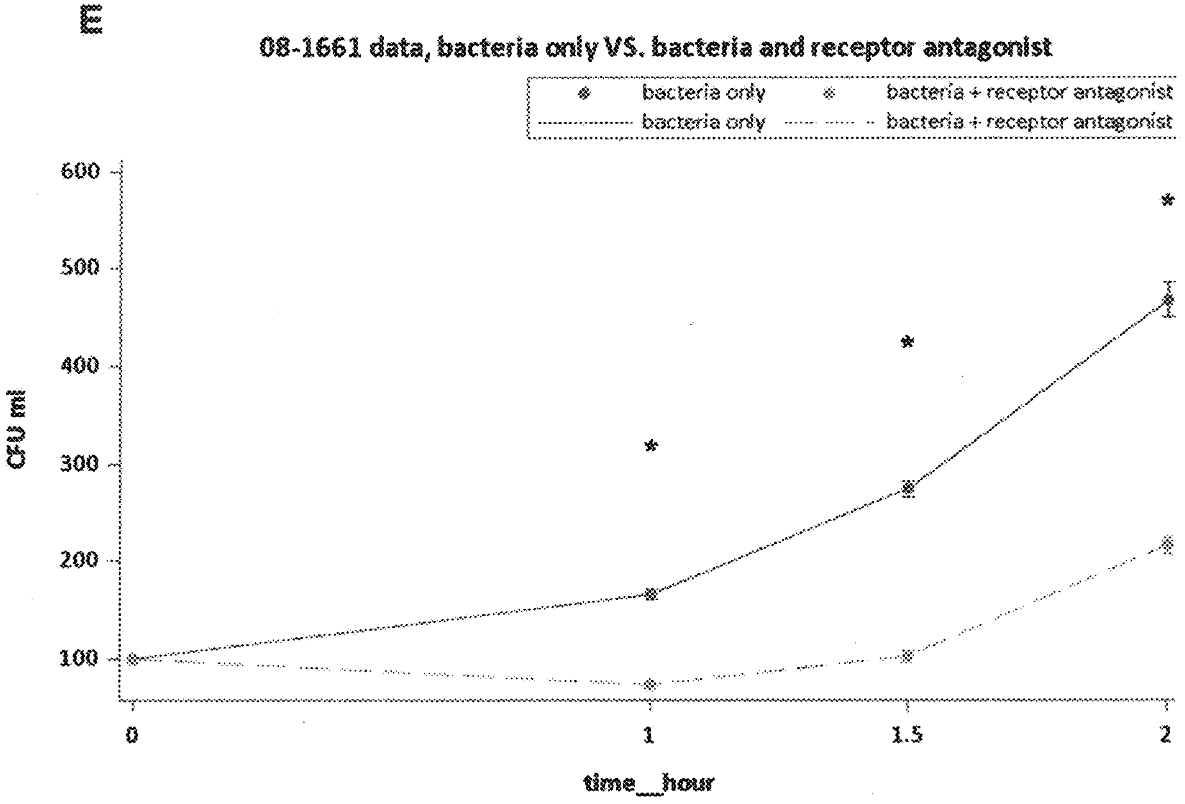
Figure 16:
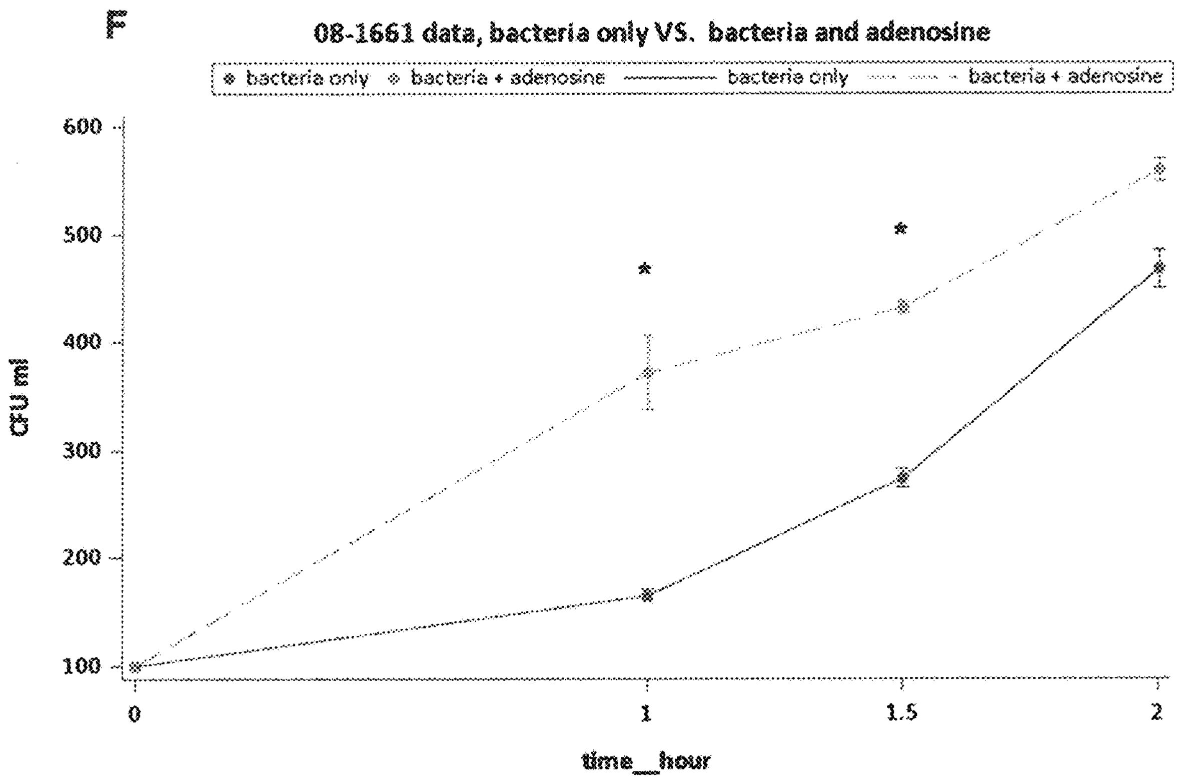

To investigate the potential immune evasive attributes of the 5'-nucleotidase activity of SpAdsA, the effect of adenosine on the survival of *S. pseudintermedius* strains 06-3228 and 08-1661 in canine blood was examined. As shown (FIGS. 16C, 16F) adenosine at a concentration of 15 μM significantly promoted 06-3228 and 08-1661 bacterial survival greater than 06-3228 alone at 1 hour (p<=0.0108) and 08-1661 alone at 1 and 1.5 hours (p<=0.0265). Conversely, 5'-(α,β-methylene) diphosphate (500 μM), a 5'-nucleotidase inhibitor, significantly diminished the ability of staphylococci to escape from phagocytic killing compared to 06-3228 without inhibitor at 1, 1.5 and 2 hours (p<=0.0108) and 08-1661 without inhibitor at 1.5 and 2 hours (p<=0.0265) (FIGS. 16A, 16D). These results suggest that extracellular adenosine produced by SpAdsA inhibits phagocytic cell activity and promotes bacterial survival.

Adenosine Mediates Inhibitory Signals Through $A_{2A}$ Receptors on Canine PMNs

To determine the role of $A_{2A}$ receptors on canine PMNs in the signaling pathway of adenosine we performed pharmacological inactivation of $A_{2A}$R using the $A_{2A}$ receptor antagonist ZM241385. With ZM241385, survival of *S. pseudintermedius* 06-3228 and 08-1661 was significantly decreased at all of time points (06-3228; p≤0.0108); 08-1661; p≤0.0265) compared to the same bacterial strains without the antagonist (FIGS. 16B, 16E).

Adenosine Inhibits Phagocytic Activity of Canine Blood PMNs for *S. pseudintermedius*

The effect of SpAdsA on PMN-mediated phagocytosis was determined with pHrodo™ labeled bacteria used for flow cytometry. PMN were gated using forward and side scatter characteristics. As shown (FIGS. 17, 18) adenosine (15 μM) significantly inhibited phagocytosis (represented as mean fluorescence intensity) of *S. pseudintermedius* 06-3228 in dog blood after incubation periods of 30 and 60 minutes (FIG. 17) at 37° C. (mean MFI=89,583; 711,453 respectively) compared to bacteria alone (mean MFI=179, 169; 1,306,632, respectively) (p<=0.0004). The inhibitory effect of adenosine was also seen with 08-1661 when incubated in canine blood at the same incubation time and temperature (FIG. 18) (Mean MFI=375,737; 764,921, respectively) compared to bacteria alone (mean MFI=833, 449; 1,128,847, respectively) (p<=0.0021).

Figure 17:
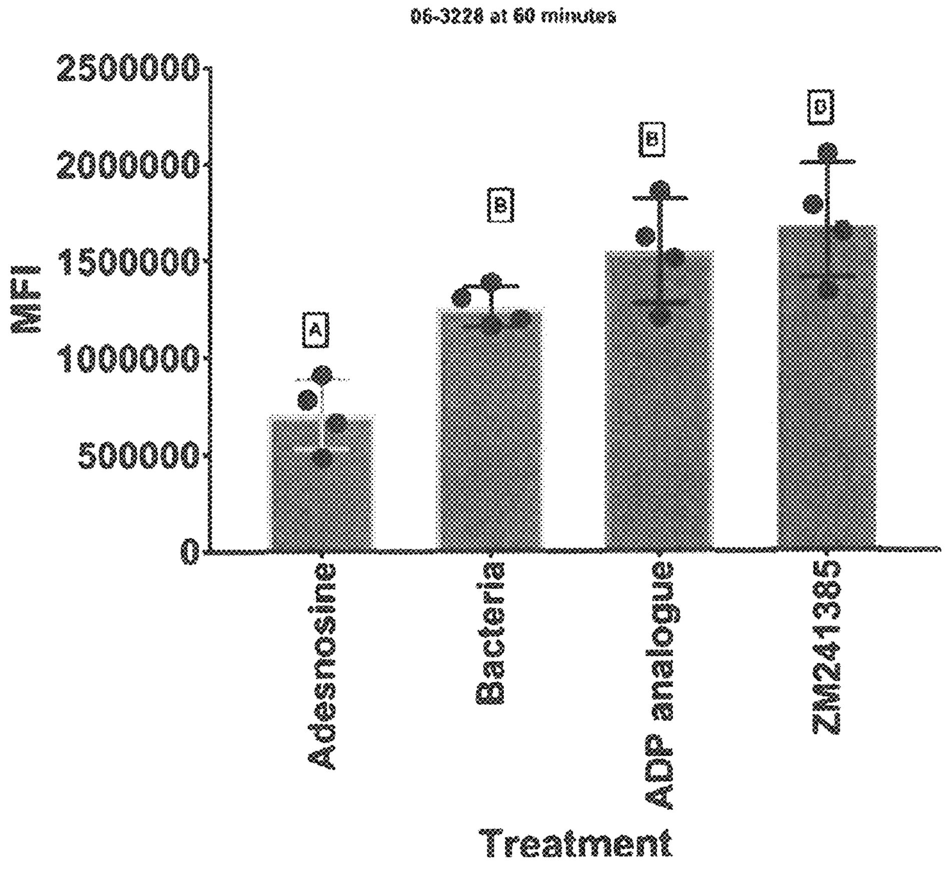
FIG. 17: Impact of adenosine, 5'-(α,β-methylene) diphosphate, and ZM241385 on *S. pseudintermedius* 06-3228 phagocytosis assay in dog blood following 1 hr of treatment, presented as MFI (n=4 per treatment; P≤0.0004).
Figure 18:
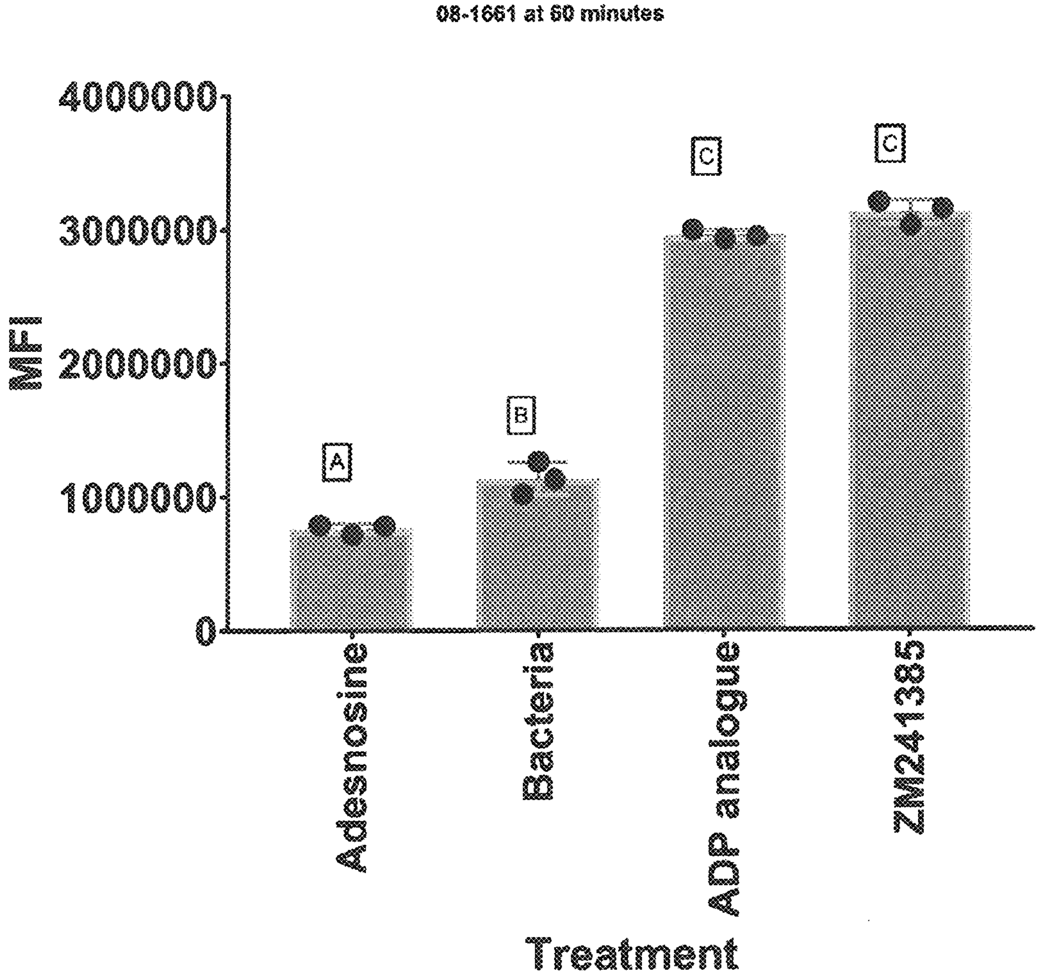
FIG. 18: Impact of adenosine, 5'-(α,β-methylene) diphosphate, and ZM241385 on *S. pseudintermedius* 08-1661 phagocytosis assay in dog blood following 1 hr of treatment, presented as MFI (n=4 per treatment; P≤0.0021).

The addition of 5'-(α,β-methylene) diphosphate (500 μM) significantly increased phagocytosis of *S. pseudintermedius* 06-3228 in dog blood after incubation periods of 30 minutes at 37° C. (FIG. 17) (mean MFI=241,513) compared to bacteria alone (mean MFI=179,169) (p<=0.0004). There was no significant difference in MFI between bacteria incubated in canine blood with ADP analogue (500 μM) and bacteria without treatment after 60 minutes of incubation at the same temperature (FIG. 17). Furthermore, the ADP analogue showed the same effect with 08-1661 when incubated in canine blood at the same incubation time and temperature (FIG. 18) (mean MFI=1,306,729; 2,924,203, respectively) compared to bacteria alone (mean MFI=833, 449; 1,128,847, respectively) (p<=0.0021).

Addition of ZM241385 (1 μM), however, antagonized the ability of *S. pseudintermedius* strain 06-3228 incubated in dog blood at 37° C. for 30 minutes (FIG. 17) to escape phagocytosis (mean MFI=241513) compared to bacteria alone (mean MFI=179169) (p<=0.0004). There was no significant difference in MFI between bacteria treated with ZM241385 (1 μM) and bacteria without treatment at 60 minutes (FIG. 17).

For *S. pseudintermedius* strain 08-1661, we found that $A_{2A}$ receptor antagonist diminished the *S. pseudintermedius* strain 06-3228 phagocytosis evasion when incubated in dog blood for 30 and 60 minutes at 37° C. (FIG. 18) (mean MFI=1,306,729; 2,924,203, respectively) compared to bacteria alone (Mean MFI=833,449; 1,128,847, respectively) (p<=0.0021). Collectively, these results showed that adenosine has an inhibitory effect on phagocytosis and it mediates its inhibitory signals through $A_{2A}$ receptors on the surface of canine neutrophils.

Discussion

This study showed how *S. pseudintermedius* modulates neutrophil function by perturbing adenosine levels using SpAdsA residing on its cell wall. It demonstrates that recombinant SpAdsA and *S. pseudintermedius* cell wall proteins containing SpAdsA hydrolyze ATP and AMP generating inorganic phosphate and adenosine. Neutrophils play a crucial role as professional phagocytes in the host defense against pathogens. They release adenosine and can respond to it via G-protein coupled receptors expressed on their surface in a dose dependent manner. Although extracellular adenosine is essential for the suppression of inflammation, accumulation of high concentrations of adenosine is also harmful. Disturbance of the immune homeostasis maintained by adenosine through perturbing its level likely affects host immune responses during infection.

A search of the GenBank database for SpAdsA protein in other members of the *Staphylococcus intermedius* group (SIG) found that 5'-nucleotidase predicted to be produced by members of this group share over 81% amino acid identity. Conversely, SpAdsA shares no more than 52% amino acid identity with proteins produced by *S. aureus, Enterococcus* and streptococcal species.

SpAdsA was considered a good candidate for producing adenosine synthase due to the presence of conserved domains associated with this enzymatic activity in other species of bacteria. Native and mutant 5' nucleotidase proteins excluding signal peptides and anchoring sequences were used for this study because the full length expressed proteins were not readily soluble in aqueous solution and would not represent mature proteins. Enzymatic inhibition using an ADP analogue or $A_2$ receptor antagonist significantly reduced bacterial survival in dog blood suggesting that *S. pseudintermedius* SpAdsA plays an important role in canine pathogen immune evasion and may serve as an important candidate target for novel anti-infective drugs and vaccines against canine pyoderma. We used an $A_2$ receptor inhibitor to determine if adenosine signaling occurs through the $A_2$ receptor in canine cells and found that the addition of ZM241385 stimulated phagocytic cell activities against *S. pseudintermedius.*

The present study revealed the diminished ability of canine blood to kill *S. pseudintermedius* in the presence of exogenous adenosine. Conversely, addition of ADP analogue or ZM241385 prevented *S. pseudintermedius* escape from phagocytic killing. In summary, these results indicate that SpAdsA plays an important role in promoting *S. pseudintermedius* survival and inhibiting PMN phagocytosis and killing activity by synthesis of adenosine and is therefore a good vaccine candidate against *S. pseudintermedius* infection.

Example 5—*Staphylococcus Pseudintermedius* Leukocidin

Through genome sequencing and analysis of the *S. pseudintermedius* secretome using liquid chromatography mass spectrometry (described above) we identified two proteins, "LukS" and "LukF", encoded on a degenerate prophage contained in the genome of *S. pseudintermedius* isolates. No other leukocidins were found in any of the available *S. pseudintermedius* genome sequences. Phylogenetic analysis of LukFS components in comparison to the rest of the leukocidin family showed that LukS was most closely related to *S. aureus* LukE, LukP and gamma hemolysin subunit A, whereas LukR was most similar to *S. aureus* gamma hemolysin subunit B. The killing effect of recombinant *S. pseudintermedius* LukF and LukS on canine polymorphonuclear leukocytes was determined using a flow cytometry cell permeability assay. The cytotoxic effect occurred only when the two recombinant proteins were combined. Engineered mutant versions of the two-component pore-forming leukocidins, produced through amino acids substitutions at selected points, were not cytotoxic. Anti-LukFS produced in dogs against attenuated proteins reduced the cytotoxic effect of native canine leukotoxin which highlights the importance of LukFS as a promising component in a vaccine against canine *S. pseudintermedius* infections. It is noted that occasionally herein the nomenclature LukS is used interchangeably with LukN and LukF is used interchangeably with LukR.

Materials and Methods

Bacterial Strains, Plasmids and Growth Conditions

The *S. pseudintermedius* strains used in this study, representing the most common multilocus sequence types (ST) previously reported in the United States, included 06-3228 (ST68), 08-1661 (ST71) and NA45 (ST84). Strains 06-3228 and 08-1661 were isolated at the University of Tennessee, College of Veterinary Medicine Bacteriology Laboratory. Strain NA45 was a gift of Faye Hartmann of the University of Wisconsin, School of Veterinary Medicine.

Plasmid construct pMA-LukS-M and pMA-LukF-M, each containing a mutated, synthetic *S. pseudintermedius* gene (designed as described below) with BamHI/NotI cloning sites, was obtained commercially (Life Technologies Corp., Carlsbad, Calif.).

Bacterial colonies grown on blood agar plates were inoculated into 5 ml of sterile trypticase soy broth (TSB) (BD Biosciences, San Jose, Calif. Cat No. RS1-011-21) and incubated overnight at 37° C. with shaking at 225 rpm (Excella E24 Incubator Shaker, New Brunswick Scientific). Fifty microliters of overnight culture were inoculated into 5 ml of fresh, sterile TSB to initiate log-phase bacterial cultures. Bacteria were grown at 37° C. with shaking at 225 rpm until an optical density of $OD_{600}$=0.4-0.6 was reached.

LC-MS/MS Analysis of *S. pseudintermedius* Supernatant

LC-MS/MS analysis was as previously described.

Bioinformatics Analysis

A rooted phylogenetic tree (UPGMA (unweighted pair group method with arithmetic mean) of LukFS was generated with Geneious version 11.0.3 using the complete protein sequences of each leukotoxin subunit with *S. pseudintermedius* protein A serving as an outgroup (Table 7). Multiple sequence alignment (MSA) of LukS and LukF proteins from diverse isolates of *S. pseudintermedius* was performed using Geneious, version 11.0.3. The bacterial localization prediction tool, PSORTb version 3.0.2 (psort.org/psortb) was used to determine the topology and domain structure of LukF and LukS.

TABLE 7

Leukotoxin subunits used in the rooted phylogenetic tree

| Protein name | Species | Accession Number | Amino acid Length |
|---|---|---|---|
| bi-component leucocidins LukPQ subunit Q | *Staphylococcus aureus* | WP_086037611.1 | 326 |
| bi-component leucocidins LukPQ subunit P | *Staphylococcus aureus* | WP_086037612.1 | 311 |
| bi-component leucocidins LukED subunit E | *Staphylococcus aureus* | WP_000473596.1 | 311 |
| bi-component leucocidins LukED subunit D | *Staphylococcus aureus* | WP_099821693.1 | 327 |
| bi-component leucocidins LukMF subunit M | *Staphylococcus aureus* | WP_000476437.1 | 308 |
| bi-component leucocidins LukMF subunit F | *Staphylococcus aureus* | WP_000694885.1 | 322 |
| bi-component leucocidins LukSF-PV subunit LukS-PV | *Staphylococcus aureus* | WP_000239544.1 | 312 |
| bi-component leucocidins LukSF-PV subunit LukF-PV | *Staphylococcus aureus* | WP_024937002.1 | 327 |
| bi-component leucocidins Hlg-AB subunit Hlg-A | *Staphylococcus aureus* | WP_000594519.1 | 309 |
| bi-component leucocidins Hlg-AB subunit Hlg-B | *Staphylococcus aureus* | WP_000783426.1 | 325 |
| LukS | *Staphylococcus pseudintermedius* | WP_014613568.1 | 310 |
| LukF | *Staphylococcus pseudintermedius* | WP_014613567.1 | 326 |

*S. pseudintermedius* LukF and LukS modeling and binding site prediction was performed using Protein Homology/analogY Recognition Engine V 2.0 (Phyre$^2$) (sbg.bio.ic.ac.uk/phyre2) and the 3DLigandSite (sbg.bio.ic.ac.uk/3dligandsite) using *S. aureus* LukS-PV, LukF-PV, LukP and LukQ as a basis to predict the critical amino acids for protein function. PHAST (phast.wishartlab.com/index) and PHASTER (phaster.ca) were used for prophage detection in a total of 22 *S. pseudintermedius* isolates. LukS-M was designed with the following substitutions: T57F, K128A and S239A and the LukF-M substitutions were S59D and N65A.

Polymerase Chain Reaction (PCR) Amplification of LukN and LukR

Bacteria from a single colony of *S. pseudintermedius* strain 06-3228 obtained from blood agar plates were grown in TSB at 37° C. with 225 rpm shaking. DNA was extracted using a MO BIO UltraClean® Microbial DNA Isolation Kit (QIAGEN Inc. Cat No. 12224-50) according to the manufacturer's instructions. Oligonucleotide primers (Integrated DNA Technology, Coralville, USA) (Table 8) were designed using a PrimerQuest Tool (www.idtdna.com/Primerquest/Home/Index) based on the genomic sequence of *S. pseudintermedius* strain 06-3228. The native LukF and LukS open reading frames (ORF) (933 and 981 bp, respectively) without the regions encoding the predicted N-terminal signal peptide were amplified from *S. pseudintermedius* 06-3228 genomic DNA and the ORF of mutant LukS and LukF were amplified from pMA-LukS-M and pMA-LukS-M plasmids (Life Technologies Corp., Carlsbad, Calif.), respectively (Table 9). PCR was performed using taq polymerase (rTaq, Takara, Cat No. R004) and the following cycling conditions were performed: initial denaturation at 95° C. for 90 seconds, 30 cycles of denaturation at 94° C. for 30 seconds, annealing at 55° C. for 30 seconds and extension at 72° C. for 1 minute followed by a final extension at 72° C. for 5 minutes. All ORFs were amplified without a histidine tag because pETBlue-2 allowed T7lac promoter-based expression of target genes with C-terminal histidine •Tag® sequences. PCR products were Sanger sequenced at The University of Tennessee Genomics Core facility.

TABLE 8

Primers used in this study to amplify recombinant wild type and attenuated LukF and LukS from S. pseudintermedius

| | |
|---|---|
| LukS-forward | GCATGA**GGATCC**GGTAAAAAATAAATTATTAGCCGCAACA |
| LukS-reverse | GCATGA**GCGGCCGC**ATTATGCCCCTTTACTTTAATTTCGTG |
| LukS-M forward | GCATGA**GGATCC**AAGGCCACGTGTCTTGTC |
| LukS-M reverse | GCATGA**GCGGCCGC**CCCATGAGGCCAGTCTTG |
| LukF-forward | GCATGA**CTCGAG**AAAAGAATGGCTAATCAAATTACACCTGTATCTG |
| LukF-reverse | GCATGA**GGATCC**TTAGTGATGGTGATGGTGATGTACTGTATGCTGATCCCAATCAA |
| LukF-M forward | GCATGA**GGATCC**GGATCCAATGAAAATAAGCAAAGTTATC |
| LukF-M reverse | GCATGA**GCGGCCGC**GCGGCCGCTGATGGGTTTTTT |

NotI, XhoI and BamHI restriction sites are underlined.

TABLE 9

Plasmids and competent cells used to clone and express recombinant wild type and attenuated *Staphylococcus pseudintermedius* LukF and LukS

| Plasmid/ Bacteria | Expressed Gene | Source |
|---|---|---|
| pMA-LukN-M | Contain attenuated *S. pseudintermedius* LukN (LukN-M) | Synthetic gene, Life Technologies Corp., Carlsbad, CA |
| pMA-LukR-M | Contain attenuated *S. pseudintermedius* LukR (LukR-M) | Synthetic gene, Life Technologies Corp., Carlsbad, CA |
| pETBlue-2 | LukN and LukN-M and LukR-M expression with blue/white screening and C-terminal HSV•Tag ® and His•Tag ® sequences | Novagen, Madison, WI |
| Dh5-alpha Tuner ™ (DE3) pLacI | Cloning and recombinant LukN and LukN-M and LukR-M protein expression | Novagen, Madison, WI |
| pKLAC2 | An integrative expression vector of *S. pseudintermedius* LukR in yeast | New England Biolabs, Ipswich, MA |
| *Kluyveromyces lactis* | An expression host of *S. pseudintermedius* LukR | New England Biolabs, Ipswich, MA |

Cloning, Expression and Purification of Recombinant Native and Attenuated LukNR

To clone *S. pseudintermedius* native and mutant LukS and mutant LukF, their PCR products were digested with Nod and BamHI, then ligated into pETBlue-2 (Novagen, Cat No 0.70674) and transformed into DH5-alpha *E. coli* chemically-competent cells (Table 9) (New England BioLabs Inc., Cat No. C2987I) by heat shock. The DH5-alpha *E. coli* were plated on LB agar plates with 100 μg/mL ampicillin. The plasmid constructs were transformed into Tuner™ (DE3) pLacI *E. coli* chemically-competent cells (Table 9) (Novagen, Cat No 0.70623) by heat shock and the Tuner™ (DE3) pLacI *E. coli* were plated on LB agar containing 50 μg/ml ampicillin and 20 μg/ml chloramphenicol.

To express recombinant *S. pseudintermedius* native and mutant LukS and mutant LukF, a single colony of Tuner™ (DE3) pLacI *E. coli* was inoculated into LB broth containing 50 μg/ml ampicillin and 20 μg/ml chloramphenicol and bacteria grown overnight at 37° C. with 225 rpm shaking. LB broth containing 50 μg/ml ampicillin and 20 μg/ml chloramphenicol was inoculated with a 1:100 dilution of overnight culture and grown at 37° C. with 225 rpm shaking until a 600 nm optical density of between 0.4 and 0.6 was reached. Protein expression was induced by addition of 1 mM Isopropyl β-D-1-thiogalatopyranoside (IPTG) (Teknova, Cat. No. I3431) and bacteria were grown for 4 hr at 30° C. with shaking at 225 rpm. Bacterial cultures were centrifuged at 12,000×g for 5 min in 5 ml of protein extraction reagent (BugBuster, Novagen Cat No. 70584) and 20 μl of 100× protease inhibitor (Cocktail Set III, EDTA-Free Calbiochem, Cat No. 539134) and incubated for 30 min at 37° C. in a shaking incubator at 225 rpm. Bacteria were pelleted by centrifugation at 12,000×g for 45 min at 4° C. Recombinant proteins were purified using affinity purification (HisPur™ Ni-NTA Spin Purification Kit, Thermo Scientific, Cat No. 88228).

Recombinant native LukF was cloned using an integrative expression vector (pKLAC2) and expressed in *Kluyveromyces lactis* (New England Biolabs, Cat No. E1000S). Recombinant protein was purified from *K. lactis* supernatant using affinity purification (HisPur™ Ni-NTA Spin Purification Kit, Thermo Scientific, Cat No. 88228). Protein concentrations were determined using a bicinchoninic acid (BCA) assay (Thermo Scientific, Cat No. 23227).

SDS-PAGE and Western Blot

Protein samples were resolved by SDS-PAGE in 4-12% polyacrylamide gels (Invitrogen, Cat No. NP0322BOX) and electrophoretically transferred onto nitrocellulose membranes (Thermo Scientific, Cat No. 77010). The blots were blocked overnight in 5% (wt/vol) nonfat dried milk powder in 0.05% polyethylene glycol sorbitan monolaurate (Tween 20) containing phosphate buffered saline (PBS-T) at 4° C. The blocked membranes were incubated with a 1:2,000 dilution of horseradish peroxidase (HRP)-conjugated anti-6×his tag monoclonal antibody (Thermo Scientific, Cat No. MA1-21315-HRP) in 0.05% PBS-T for 1 h with 225 rpm shaking at room temperature. After five washes with 0.05% PBS-T bound antibodies were detected using 1-Step™ chloronaphthol substrate solution (Thermo Scientific, Cat No. 34012).

Preparation of Canine Anti-*S. pseudintermedius* LukNR

Recombinant LukS-M and LukF-M produced in *E. coli* were purified using affinity chromatography (as above) and endotoxin concentrations were measured using a ToxinSensor™ Chromogenic LAL Endotoxin Assay Kit (Genscript, Cat. No. L00350). Recombinant LukS-M and LukF-M at 20 μg each/0.5 cc in phosphate buffered saline (PBS) (pH 7.2) were injected in the lateral thorax by the subcutaneous route, into three clinically normal dogs. Injections were given once every 7 days for a total of three injections with a control dog receiving PBS (pH 7.2) only. Blood (6 cc) was collected from a jugular vein 4 times, on days −7, 8, 15 and 29. The collected blood was left undisturbed at room temperature for 30 min followed by centrifugation at 2,000×g for 10 min in a refrigerated centrifuge.

Enzyme-Linked Immunosorbent Assay

For measurement of recombinant protein antigenicity, LukS-M and LukF-M were coated separately onto ELISA plates (Corning, Cat No. 3590) at 2 μg/ml in PBS (pH 7.2). The plates were washed with 0.05% PBS-T and incubated with two-fold serial diluted serum from dogs (injected with recombinant proteins) for 1 h at 37° C., then bound IgG was detected using HRP-conjugated goat anti-dog IgG heavy and light chain (Bethyl Laboratories, Inc. Cat No. A40-123-1). ELISA assays plates were washed three times with PBS-T between all incubations, bound antibodies were detected using TMB substrate (Thermo Scientific, Cat No. N301), reactions were stopped with 0.18 M sulphuric acid and optical density read at 450 nm on a plate reader (Bio TEK, EL800). The experiment was repeated a minimum of three times and a p-value of <0.05 was considered significant for all the experiments unless otherwise stated.

PMN Cell Permeability Assay

Canine blood was collected from healthy dogs using a sterile blood collection system with EDTA anti-coagulant (BD Vacutainer). Then, 600 μl of dog blood was added to 1 ml of red blood cell lysing buffer (Hybri-Max™, Sigma-Aldrich, Cat No. R7757-100ML) for 30 min at 37° C. in 15 ml sterile plastic tube, centrifuged and re-suspended in 1 ml RPMI medium supplemented with 10% fetal bovine serum. PMNs were incubated with recombinant proteins (LukS and LukF, LukS alone, LukF alone, LukS-M and LukF-M) in a volume of 500 μl in RPMI medium supplemented with 10% fetal bovine serum in a 5% $CO_2$ incubator for 30 min. Supernatant of *S. pseudintermedius* 06-3228 was harvested at log phase to test the toxic effect of secreted LukFS. PMNs were stained with 1 μl of Sytox Green (Life technologies, Inc. Cat No. 1776406) for 30 min, washed with PBS (pH 7.2) twice and analyzed using a flow cytometer (Attune acoustic focusing cytometer) by gating on PMNs based on their side and forward scatter properties. In order to measure the protective effect of anti-LukFS on canine PMNs, recombinant LukF and LukS were incubated with canine anti-LukS-M LukF-M at a dilution of 1:100 for 30 min at 37° C., then tested with the cell permeability assay as previously described.

Biotin Labeling of *S. pseudintermedius* Wild Type and Attenuated LukFS

Purified recombinant *S. pseudintermedius* wild type and attenuated LukS and LukF at 500 μg/ml in PBS (pH 7.2) were incubated with 50 μl of 10 mM EZ-Link Sulfo-NHS-LC-Biotin reagent (equal to 20-fold molar excess of biotin) (Thermo Scientific, Cat No. 21327) for 30 min at room temperature. Excess biotin was removed using an Amicon Ultra-0.5 Centrifugal Filter Unit with a 30 kDa molecular weight cut-off (Milipore sigma, Cat No. UFC5030). The biotin-labeled proteins were stored at −20° C. until further use.

To test the binding of wild type and attenuated LukS and LukF to canine PMNs, biotin labelled recombinant proteins were incubated with PMNs from a clinical healthy dog for 30 minutes at room temperature, the cells were washed, then PMNs were incubated with 1:500 dilution of avidin-FITC conjugate (Sigma-Aldrich, A2050) at room temperature for 30 minutes in the dark. Unbound conjugate was removed by washing and the amount of binding was determined using a flow cytometer (Attune acoustic focusing cytometer) by gating on PMNs based on their side and forward scatter properties.

Statistical Analysis

All analyses were conducted using the GraphPad Prism software (Version 7, GraphPad Software Inc.).

Results

LC MS/MS Data Analysis of *S. pseudintermedius* Culture Supernatant

We used LC-MS/MS to screen culture supernatants of three clinical strains of *S. pseudintermedius* (06-3228, 08-1661 and NA45) for putative leukocidins and identified proteins with homology to LukS and LukF subunits of previously described leukocidins. LukS and LukF proteins were detected in the supernatant fraction of 06-3228, 08-1661 and NA45, respectively (Table 10). The LukFS components were detected in the supernatants of the three isolates as two proteins secreted independently with 310 and 326-amino acid sequences for LukS and LukF, respectively.

TABLE 10

LC MS/MS analysis of *S. pseudintermedius* culture supernatant.

| Strain/Protein | Coverage |
|---|---|
| Strain 06-3228 | |
| LukS | 9 |
| LukF | 36.2 |
| Strain 08-1661 | |
| LukS | 51 |
| LukF | 42.3 |
| Strain NA45 | |
| LukS | 54.5 |
| LukF | 57.4 |

LukS and LukF were secreted by *S. pseudintermedius* 06-3228, 08-1661 and NA45. Secretome proteins were compared among the three isolates using their respective genomes as reference databases. Percent coverage was calculated by dividing the number of amino acids in all found peptides by the total number of amino acids in the entire protein sequence.

LukFS: A New Phage Encoded Leucocidin

Multiple sequence alignment (MSA) analysis showed that LukFS is conserved among *S. pseudintermedius* strains including 06-3221, 08-1661 and NA45. The LukF and LukS genes contain open reading frames in *S. pseudintermedius* that are 933 and 981 bp in length respectively, with amino acid identities over 99.4% between strains.

A 14.9 kb incomplete prophage (similar to Φ Staphy_96_NC_007057) was identified in the genome of *S. pseudintermedius* 06-3228. A BLAST search of 1 Staphy_96_NC_007057 using complete genome sequences of *S. pseudintermedius* strains available in the GenBank database and others sequenced in our lab but not yet published, revealed that approximately 7 Kb of the phage are present in all of *S. pseudintermedius* isolates examined (a total of 22 isolates). They also contain the coding DNA sequences (CDS) of ascorbate-specific PTS system EII A, B and C components, probable L-ascorbate-6-phosphate lactonase UlaG (L-ascorbate utilization protein G), phosphoglycerate mutase family 2 and hypothetical protein.

Phylogenetic analysis of LukFS in comparison to the entire leukocidin family showed that LukS is most closely related to *S. aureus* LukE, LukP and gamma hemolysin subunit A. *S. pseudintermedius* LukF is most closely related to *S. aureus* gamma hemolysin subunit B (data not shown).

Multiple sequence alignment (MSA) analysis showed that LukFS in *S. pseudintermedius* is a unique leukotoxin and that each functional component shares considerable similarity with other staphylococcal leukotoxin fractions (Table 11).

TABLE 11

MSA of LukS and LukF subunits of *S. pseudintermedius* strain 06-3228 with corresponding proteins in seven other leukotoxins.

| | LukP | hlgA | LukE | Luk M | LukS-PV |
|---|---|---|---|---|---|
| *S. pseudintermedius* | 75.64% | 73.08% | 73.72% | 68.49% | 64.76% |
| | LukF-PV | LukQ | LukF | LukD | hlgB |
| *S. pseudintermedius* | 73.60% | 74.54% | 73.46% | 76.07% | 72.62% |

A BLAST search of LukFS in the GenBank database revealed that it shares sequence similarity with other pathogenic bacterial species within the *Staphylococcus intermedius* group. LukS shares 98.7% identity with *Staphylococcus intermedius* and 90.6% identity with *Staphylococcus delphini*. LukF has 99% amino acid identity with *S. intermedius* and 85% amino acid identity with *S. delphini.*

Figure 20:
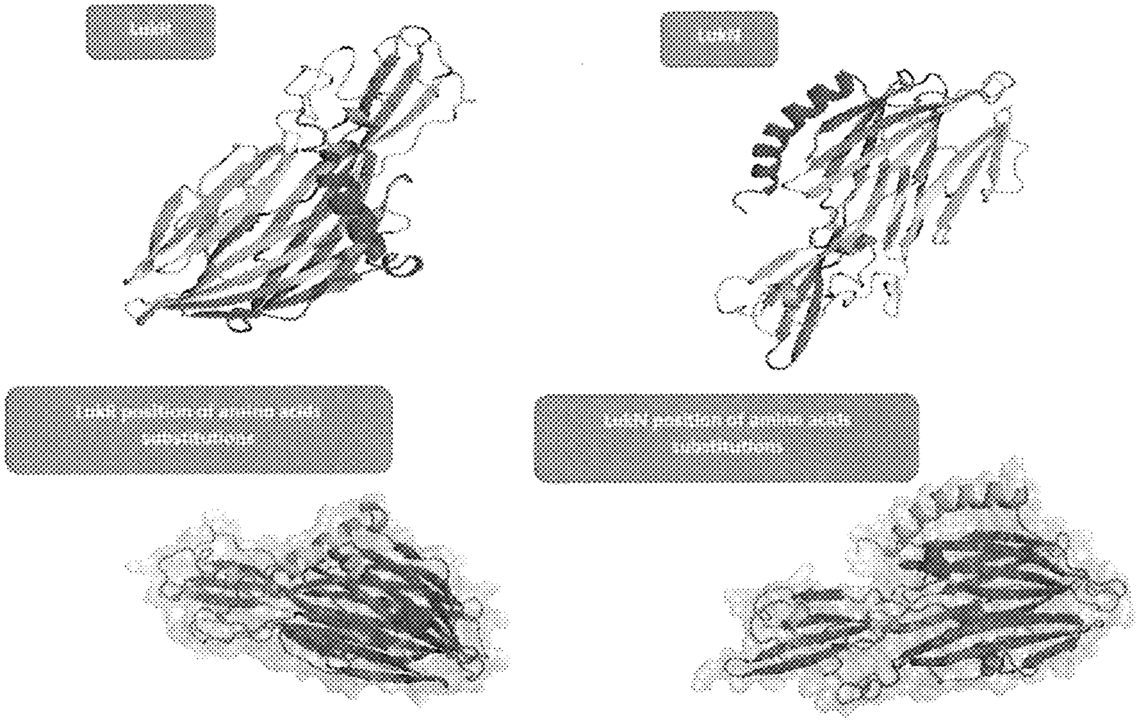
FIG. 20: Native (a) and mutant (b) LukN and LukR of *S. pseudintermedius* strain 06-3228.

The LukS and LukF model developed with the Phyre$^2$ web portal, using *S. aureus* LukPQ as a basis to predict critical residues for protein function (FIG. 20), showed that threonine, lysine and serine, at positions 57, 128 and 239, respectively in LukS, are essential for the activity of the protein. The LukF model predicted that serine and asparagine at positions 59 and 65 are critical amino acids for leucocidin activity.

Cloning, Expression and Purification of Recombinant *S. pseudintermedius* LukS and LukF Recombinant polyhistidine tagged wild type and mutant LukS and LukF were generated in *E. coli* and LukR was secreted in the culture supernatant of *K. lactis* using an integrative expression vector (pKLAC2). Recombinant proteins were purified using HisPur Ni-NTA resin under native conditions and eluted using an imidazole gradient. The molecular weights of LukS, LukS-M, LukF and LukF-M determined in western blots were of the expected sizes (39.43, 39.12, 37.27 and 37.59 kDa, respectively). The endotoxin levels of purified recombinant, attenuated LukS and LukF were below 0.5 endotoxin units/mg protein.

Attenuated LukFS Induces Specific Antibody Responses

Figure 21:
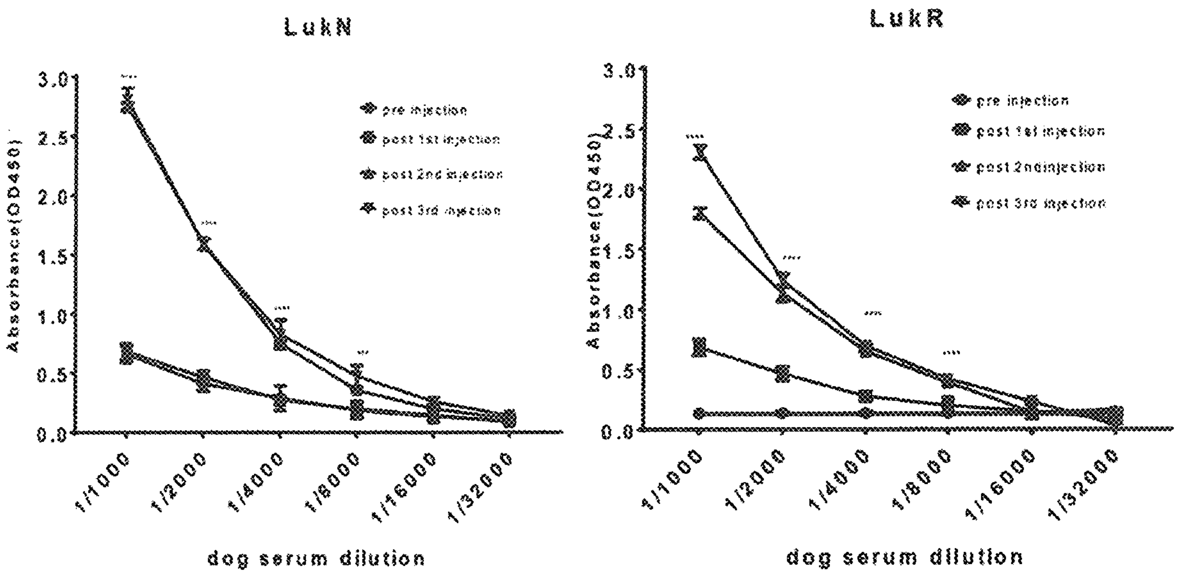
FIG. 21: Canine anti-LukN-M and LuR-M react with recombinant wild type LukN and LukR.

Specific antibodies against *S. pseudintermedius* wild type and attenuated LukF and LukS were detected using an indirect ELISA, with sera collected on days −7, 8, 15 and 29, after the second injection of LukS-M and LukF-M (on day 15) and was higher on day 29 (P<0.0001) compared to pre-injection control sera (FIG. 21).

Antibodies against *S. pseudintermedius* wild type LukS and LukF were detected using an indirect ELISA. Recombinant *S. pseudintermedius* LukS and LukF proteins were coated on ELISA plates, then incubated with two-fold serially diluted serum from dog vaccinated with the same proteins. High reactivity with LukS and LukF was seen from sera collected two weeks after the third injection of LukS-M and LukF-M (P=0.0001**) and was higher (P=0.0003*) compared to pre-injection sera. The values represent averages from two independent experiments.

LukFS Kills Canine PMNs

Figure 22:
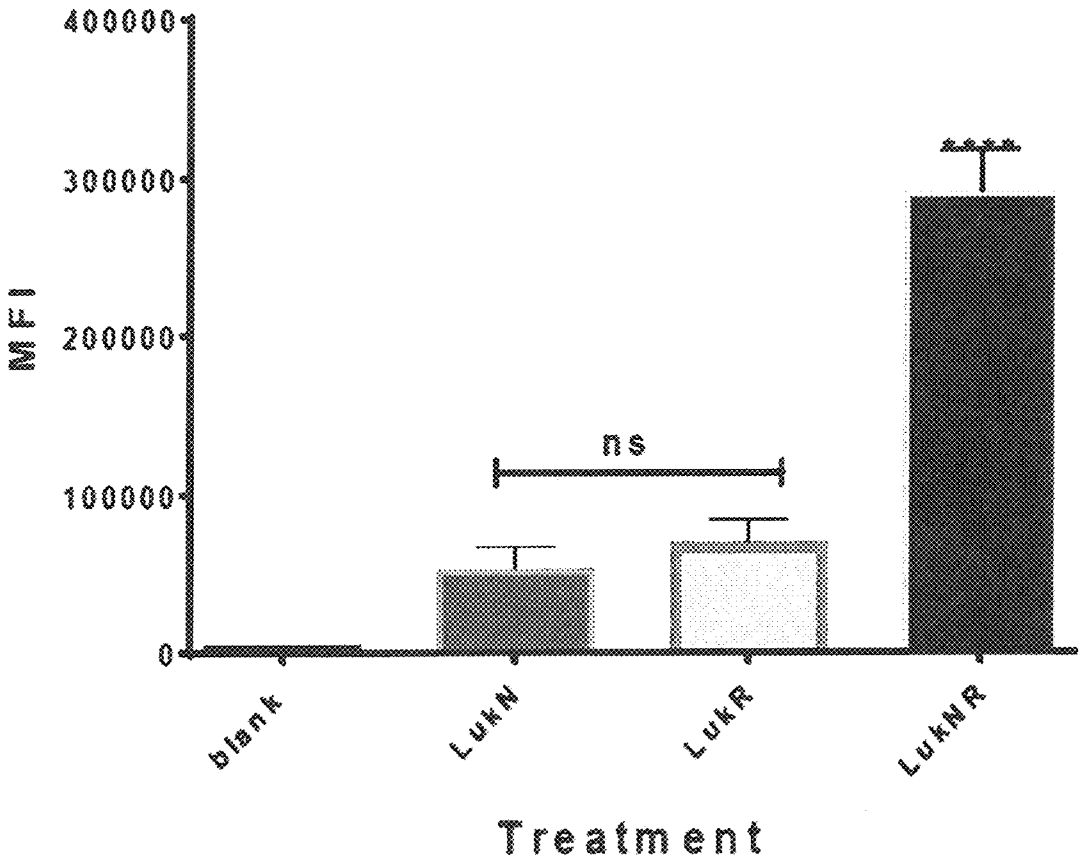
FIG. 22: Cytotoxic effect of *S. pseudintermedius* recombinant LukNR on canine PMNs. The mean fluorescent intensity (MFI) of blank, LukNR, LukNR-M, wild type and attenuated LukN and LukR relative to *S. pseudintermedius* 06-3228 supernatant were calculated based on average values from three independent experiments. (*P<0.05 was considered significant). ns—Not significant. The MFI of LukNR and *S. pseudintermedius* supernatant were significantly higher (P=0.0001****) compared to that of single component or attenuated LukNR together.

Canine PMNs were highly susceptible to LukFS with lysis induced within 30 minutes at a concentration of 200 ng of each leukotoxin component (P<0.0001) and a 1:2 *S. pseudintermedius* 06-3228 supernatant dilution (P<0.0001) (FIG. 22). LukS-M and LukF-M together or native proteins alone showed a diminished killing effect on PMNs of dogs.

Dog Anti-LukFS Reduced the Cytotoxic Effect of Canine Leukotoxin on PMNs

Figure 23:
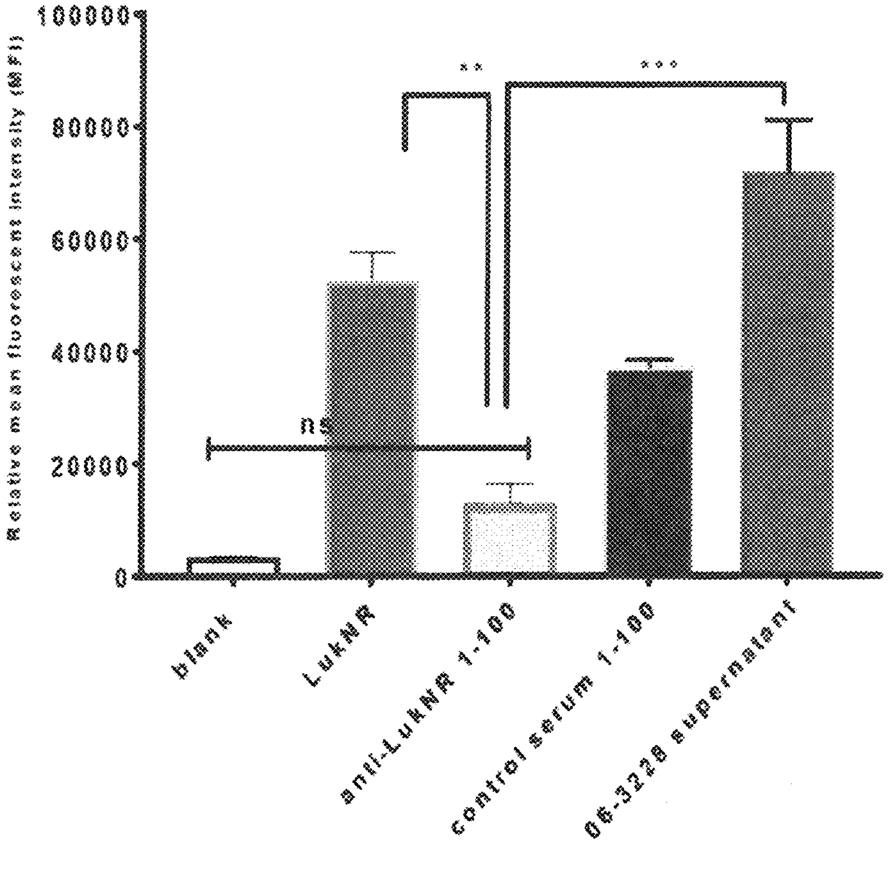
FIG. 23: Dog anti-LukN-M and LukR-M antibody protects canine PMNs from the cytotoxic effects of LukNR. LukNR preincubated with dog anti-LukNR-M resulted in a 52645±3570 SEM, n=2 reduction in mean fluorescent intensity (MFI) compared with that of LukNR treatment alone (P=0.0027) and with that of 06-3228 supernatant treatment alone (P=0.0004*).

Dog anti-LukFS at a dilution of 1:100 preincubated with LukFS showed a 52645±3570, n=2 reduction in mean fluorescent intensity (MFI) compared with LukFS treatment alone (FIG. 23).

Discussion

We identified a new member of the two-component leucocidin family. LukFS is highly conserved among *S. pseudintermedius* isolates and appears to be the only leucocidin produced by this species. It is associated with an incomplete prophage that occurs in degenerate form across all *S. pseudintermedius* isolates for which genomic sequence is available.

In accordance with its host distribution in a canine opportunistic pathogen, LukFS is cytotoxic against dog PMNs. This highlights the immune-evasive attribute of *S. pseudintermedius* LukFS in the dog, in line with the assumed function of other phage-encoded leukocidins that similarly have a host-specific function and distribution.

LukS-M and LukF-M, attenuated to reduce their toxicity, bound to canine leukocytes without causing any significant killing suggesting the mutations disrupted their ability to oligomerize, an essential function required for cytolysis. The low concentration of endotoxin in the recombinant proteins and the low toxicity exhibited by the attenuated protein produced in *E. coli* suggests that endotoxin did not play a role in neutrophil killing.

Example 6—*Staphylococcus pseudintermedius* Exotoxin 15 (SpEX)

Analysis of the *S. pseudintermedius* secretome using liquid chromatography mass spectrometry (LC-MS) guided by genome sequences, we identified an *S. pseudintermedius* exotoxin provisionally named SpEX. This exotoxin binds to and kills polymorphonuclear leukocytes (PMNs) and peripheral blood mononuclear cells (PBMCs) and inhibits chemotaxis at sublethal concentrations. A mutant version of SpEX, produced through amino acids substitutions at selected points, had diminished cytotoxicity. Anti-SpEX produced in dogs reduced the inhibitory effect of native SpEX on canine PMNs chemotaxis and was statistically significant in protecting the dog immune cells from the toxic effect of the native recombinant protein. These results suggest that attenuated SpEX produced in this study is a good candidate for inclusion in a vaccine or a therapeutic for use in the treatment and prevention of *S. pseudintermedius* infections.

Materials and Methods

Bacterial Strains, Plasmids and Growth Conditions

The *S. pseudintermedius* strains used in this study, representing the most common multilocus sequence types (ST) reported in the United States, included 06-3228 (ST68) and 08-1661 (ST71) were isolated at the University of Tennessee, College of Veterinary Medicine Bacteriology Laboratory. Strain NA45 was a gift of Faye Hartmann of the University of Wisconsin, School of Veterinary Medicine.

A plasmid construct containing a mutated, synthetic *S. pseudintermedius* spEX (designed as described below) with BamHI/NotI cloning sites, was obtained commercially (Genscript Piscataway, N.J. USA) (Table 12). Bacterial colonies grown on blood agar plates were inoculated into 5 ml of sterile trypticase soy broth (TSB) (BD Biosciences, San Jose, Calif. Cat No. RS1-011-21) and incubated overnight at 37° C. with shaking at 225 rpm (Excella E24 Incubator Shaker, New Brunswick Scientific). Fifty microliters of overnight culture were inoculated into 5 ml of fresh, sterile TSB to initiate log-phase bacterial cultures. Bacteria were grown at 37° C. with shaking at 225 rpm until an optical density ($OD_{600}$) of 0.4-0.6 was reached.

TABLE 12 plasmids and competent cells used to clone and express recombinant wild-type and attenuated SpEX from *Staphylococcus pseudintermedius.*

| Plasmid/ Bacteria | Expressed Gene | Source |
|---|---|---|
| pUC19-spEX-M plasmid | Contain attenuated full length *S. pseudintermedius* SpEX | Genscript Piscataway, NJ USA |

TABLE 12-continued plasmids and competent cells used to clone and express recombinant wild-type and attenuated SpEX from *Staphylococcus pseudintermedius.*

| Plasmid/ Bacteria | Expressed Gene | Source |
|---|---|---|
| pETBlue-2 | SpEX and SpEX-M expression with blue/white screening and C-terminal HSV•Tag ® and His•Tag ® sequences | Novagen, Madison, WI |
| Dh5-alpha Tuner ™ (DE3) pLacI | Cloning and recombinant SpEX and SpEX-M protein expression | Novagen, Madison, WI |

LC-MS/MS Analysis of *S. pseudintermedius* Supernatant

LC-MS/MS analysis was as described above.

Bioinformatics Analysis

Multiple sequence alignment (MSA) of SpEX proteins from diverse isolates of *S. pseudintermedius* was performed using Geneious, version 11.0.3. *S. pseudintermedius* SpEX modeling and binding site prediction were performed using Protein Homology/analogY Recognition Engine V 2.0 ($Phyre^2$) (sbg.bio.ic.ac.uk/$phyre^2$) and the 3DLigandSite (sbg.bio.ic.ac.uk/3dligandsite). A pairwise sequence alignment of *S. pseudintermedius* SpEX and *S. aureus* SSL11 was used to identify conserved amino acids critical for SpEX activity. We designed a full-length, attenuated *S. pseudintermedius* SpEX construct (SpEX-M), with the following amino acid substitutions using Geneious, version 11.0.3: D102A, T125P, T206P and R217A.

Polymerase Chain Reaction (PCR) Amplification of spEX

Bacteria from a single colony of *S. pseudintermedius* strain 06-3228 obtained from blood agar plates were grown in TSB at 37° C. with 225 rpm shaking. DNA was extracted using a MO BIO UltraClean® Microbial DNA Isolation Kit (QIAGEN Inc. Cat No. 12224-50) according to the manufacturer's instructions. Oligonucleotide primers (Integrated DNA Technology, Coralville, USA) (Table 13) were designed using a PrimerQuest Tool (idtdna.com/Primerquest/Home/Index) based on the genomic sequence of *S. pseudintermedius* strain 06-3228.

TABLE 13

Primers used to amplify recombinant wild- type and attenuated spEX from Staphylococcus pseudintermedius and pUC19-spEX-M plasmid, respectively. NotI and BamHI restriction sites are underlined.

| | |
|---|---|
| Native full length spEX forward | GCATGA<u>GGATCC</u>AAGCGAAGCACATGCCCA |
| Native full length spEX reverse | GCATGA<u>GCGGCCGC</u>CAGATCTATCGTAATTTGTTGGA |
| Attenuated full length spEX forward | GCATGA<u>GGATCC</u>AATGAAACAGAGCACCATTCT |
| Attenuated full length spEX reverse | GCATGA<u>GCGGCCGC</u>CAGGTCGATG |

The native SpEX open reading frames (ORF) (705 bp) without the regions encoding the predicted N-terminal signal peptide were amplified from *S. pseudintermedius* 06-3228 genomic DNA and the ORF of mutant SpEX were amplified from a pUC19-spEX-M plasmid (Genscript Piscataway, N.J. USA) (Table 12). PCR was performed using taq polymerase (rTaq, Takara, Cat No. R004) and the following cycling conditions were performed: initial denaturation at 95° C. for 90 seconds, 30 cycles of annealing at 55° C. for 30 seconds and extension at 72° C. for 1 minute followed by a final extension at 72° C. for 5 minutes. All ORFs were amplified without a histidine tag because pETBlue-2 allowed T7lac promoter-based expression of target genes with C-terminal histidine •Tag® sequences. PCR products were sequenced at The University of Tennessee Genomics Core facility.

Cloning, Expression, and Purification of Recombinant Native and Attenuated SpEX

To clone *S. pseudintermedius* native and mutant SpEX, their PCR products, amplified from synthetic genes, were digested with Nod and BamHI, then ligated into pETBlue-2 (Novagen, Cat No 0.70674) (Table 12) and transformed into DH5-alpha *E. coli* chemically-competent cells (Table 12) (New England BioLabs Inc., Cat No. C2987I) by heat shock. The DH5-alpha *E. coli* were plated on LB agar plates with 100 μg/mL ampicillin. The plasmid constructs were transformed into Tuner™ (DE3) pLacI *E. coli* chemically-competent cells (Table 12) (Novagen, Cat No 0.70623) by heat shock and the Tuner™ (DE3) pLacI *E. coli* were plated on LB agar containing 50 μg/ml ampicillin and 20 μg/ml chloramphenicol.

To express recombinant *S. pseudintermedius* native and mutant SpEX, a single colony of Tuner™ (DE3) pLacI *E. coli* was inoculated into LB broth containing 50 μg/ml ampicillin and 20 μg/ml chloramphenicol and the bacteria grown overnight at 37° C. with 225 rpm shaking. LB broth containing 50 μg/ml ampicillin and 20 μg/ml chloramphenicol was inoculated with a 1:100 dilution of overnight culture and grown at 37° C. with 225 rpm shaking until a 600 nm optical density of between 0.4 and 0.6 was reached. Protein expression was induced by addition of 1 mM Isopropyl β-D-1-thiogalatopyranoside (IPTG) (Teknova, Cat. No. I3431) and bacteria were grown for 4 hr at 30° C. with shaking at 225 rpm. Bacterial cultures were centrifuged at 12,000×g for 5 min. in 5 ml of protein extraction reagent (BugBuster, Novagen Cat No. 70584) and 20 μl of 100× protease inhibitor (Cocktail Set III, EDTA-Free Calbiochem, Cat No. 539134) and incubated for 30 min at 37° C. in a shaking incubator at 225 rpm. Bacteria were pelleted by centrifugation at 12,000×g for 45 min at 4° C. Recombinant proteins were purified using affinity purification (HisPur™ Ni-NTA Spin Purification Kit, Thermo Scientific, Cat No. 88228).

Protein concentrations were determined using a bicinchoninic acid (BCA) assay (Thermo Scientific, Cat No. 23227).

SDS-PAGE and Western Blot

Protein samples were resolved by SDS-PAGE in 4-12% polyacrylamide gels (Invitrogen, Cat No. NP0322BOX) and electrophoretically transferred onto nitrocellulose membranes (Thermo Scientific, Cat No. 77010). The blots were blocked overnight in 5% (wt/vol) nonfat dried milk powder in 0.05% polyethylene glycol sorbitan monolaurate (Tween 20) containing phosphate buffered saline (PBS-T) at 4° C. The blocked membranes were incubated with a 1:2,000 dilution of horseradish peroxidase (HRP)-conjugated anti-6×his tag monoclonal antibody (Thermo Scientific, Cat No. MA1-21315-HRP) in 0.05% PBS-T for 1 h with 225 rpm shaking at room temperature. After five washes with 0.05% PBS-T bound antibodies were detected using 1-Step™ chloronaphthol substrate solution (Thermo Scientific, Cat No. 34012).

Preparation of Canine Anti-*S. pseudintermedius* SpEX

Recombinant SpEX-M (SEQ ID NO:12) produced in *E. coli* was purified using affinity chromatography (as above) and endotoxin concentration was measured using a ToxinSensor™ Chromogenic LAL Endotoxin Assay Kit (Genscript, Cat. No. L00350). Recombinant SpEX-M at 20 μg each/0.5 cc in phosphate buffered saline (PBS) (pH 7.2) were injected in the lateral thorax by the subcutaneous route, into three clinically normal dogs. Injections were given once every 7 days for a total of three injections with a control dog receiving PBS (pH 7.2) only. Blood (6 cc) was collected from a jugular vein 4 times, on days −7, 8, 15 and 29 (relative to injections). The collected blood was left undisturbed at room temperature for 30 min followed by centrifugation at 2,000×g for 10 min in a refrigerated centrifuge.

Enzyme-Linked Immunosorbent Assay

For measurement of recombinant protein antigenicity, SpEX and SpEX-M were coated separately onto ELISA plates (Corning, Cat No. 3590) at 2 μg/ml in PBS. The plates were washed with 0.05% PBS-T and incubated with two-fold serial diluted serum from dogs (injected with recombinant proteins) for 1 h at 37° C., then bound IgG was detected using HRP-conjugated goat anti-dog IgG-heavy and light chain (Bethyl Laboratories, Inc. Cat No. A40-123-1). ELISA assays plates were washed three times with PBS-T between all incubations, bound antibodies were detected using TMB substrate (Thermo Scientific, Cat No. N301), reactions were stopped with 0.18 M sulphuric acid and optical density read at 450 nm on a plate reader (Bio TEK, EL800). The experiment has repeated a minimum of three times and a p-value of <0.05 was considered significant for all the experiments unless otherwise stated.

PMN Preparation

Canine blood was collected from healthy dogs using a sterile blood collection system with EDTA anticoagulant (BD Vacutainer). Then, 600 μl of dog blood was added to 1 ml of red blood cell lysing buffer (Hybri-Max™, Sigma-Aldrich, Cat No. R7757-100ML) for 30 min at 37° C. in 15 ml sterile plastic tube, centrifuged and re-suspended in 1 ml RPMI medium supplemented with 10% fetal bovine serum.

PMN Transmigration Assay

A neutrophil transmigration assay protocol as previously described (24) was used with modifications. The assay was conducted in modified 24-well plates with polycarbonate membrane (3.0 μM pore size and 6.5 mm well diameter) chamber (Corning Incorporated, NLD Cat No. 3415). Six hundred microliters of DMEM medium was placed in each well and 10% of fetal bovine serum was used as a PMN chemoattractant. *S. pseudintermedius* 06-3228 culture supernatant harvested at log phase was used as positive control and DMEM medium alone was used as negative control. Subsequently, isolated canine PMNs ($1\times10^6$) were added to the top (basolateral) chamber and incubated at room temperature for 6 h. PMNs that migrated across the bottom (apical) chamber were quantified using a Countess™ II FL Automated Cell Counter (Thermo Scientific, USA Cat No. AMQAF1000).

In order to measure the protective effect of anti-SpEX on neutrophil chemotaxis, recombinant SpEX was incubated with canine anti-SpEX at a dilution of 1:100 for 30 min at 37° C., then tested with PMN transmigration assay as previously described.

Complement C5 Binding Assay

Human complement component C5 was coated onto ELISA plates (Corning, Cat No. 3590) at 2 μg/ml in PBS as previously described. Recombinant SpEX and SpEX-M were added at 500 ng/ml in PBS (pH 7.2) for 1 h at 37° C., then bound recombinant proteins were detected using (HRP)-conjugated anti-6×his tag monoclonal antibody (Thermo Scientific, Cat No. MA1-21315-HRP) at dilution of 1:1000 in PBS-T (pH 7.2). Bound antibodies were detected using TMB substrate (Thermo Scientific, Cat No. N301), reactions were stopped with 0.18 M sulphuric acid and optical density read at 450 nm on a plate reader (Bio TEK, EL800). The experiment has repeated a minimum of three times and a p-value of <0.05 was considered significant for all the experiments unless otherwise stated.

Hemolysis Assay

In order to detect the ability of recombinant SpEX to bind with complement component C5 and inhibit its function, a hemolysis assay was performed. Bovine erythrocytes were sensitized to complement by incubation with rabbit IgG fraction anti-bovine red blood cells (ICN Cappel, Cat No. 55271) diluted 1:25, for 30 min at 37° C. with gentle mixing. Dog serum, diluted 1:4, was pre-incubated with 500, 1000 and 2000 ng/ml of recombinant native SpEX for 30 min at 37° C. and gentle shaking (100 rpm). One hundred microliters of sensitized bovine RBCs were added and further incubated for 30 min at 37° C. with gentle shaking. After centrifugation at 4200×g for 5 min, the absorbance of the supernatant was measured at 450 nm. Heat-inactivated serum mixed with PBS (pH 7.2) was used as a negative control and 25% normal dog serum used as a positive control.

PMNs and PBMCs Permeability Assay

PMNs and PBMCs were separated as previously described. PMNs and PBMCs were incubated with recombinant proteins (SpEX and SpEX-M) at concentration of 100 μg in a volume of 500 μl in RPMI medium supplemented with 10% fetal bovine serum in a 5% $CO_2$ incubator for 30 min. The supernatant of *S. pseudintermedius* 06-3228 was harvested at log phase to test the toxic effect of secreted SpEX. PMNs and PBMCs were stained with 1 μl Sytox green (Life Technologies, Inc. Cat No. 1776406) for 30 min, washed twice with PBS (pH 7.2) and analyzed using a flow cytometer (Attune acoustic focusing cytometer) by gating on PMNs and PBMCs based on their side and forward scatter properties.

To determine the protective effect of canine anti-SpEX-M on PMNs and PBMCs, recombinant *S. pseudintermedius* SpEX at concentration of 100 μg/ml in PBS (pH 7.2) was incubated for 30 minutes at 37° C. with serum from SpEX-M injected dogs. The experiment was run in duplicate and a p-value of <0.05 was considered significant.

For flow cytometry analysis the cut-off for cell death was established using leukocytes incubated without SpEX. Mean fluorescent intensity was determined from all gated cells.

Statistical Analysis

Each experiment was repeated at least three times and a p-value of <0.05 was considered significant. Experiments including ELISA and flow cytometry on serum from injected dogs were run in technical duplicates. All analyses were conducted using the GraphPad Prism software (Version 7, GraphPad Software Inc.).

Results

*S. pseudintermedius* SpEX Secreted in the Culture Supernatant

LC-MS/MS was used to screen culture supernatants of three clinical strains of *S. pseudintermedius* (06-3228, 08-1661 and NA45), representing the major sequence types occurring in the United States as determined by multilocus sequence typing. SpEX was detected in the supernatants of the three isolates with 234-amino acid sequences.

*S. pseudintermedius* 06-3228 secrete SpEX that shares 91.45, 88.89% amino acid identity with that of 08-1661 and NA45 strains, respectively with mean pairwise % identity of 92.9% and 208 identical amino acid. The mean molecular weight is 26.093 kDa and the mean isoelectric point is 6.30.

Bioinformatics Analysis and *S. pseudintermedius* SpEX Characteristics

A BLAST search of SpEX in the GenBank database revealed that it is highly conserved in *S. pseudintermedius* isolates and it shares sequence similarity with other pathogenic bacterial species within the *Staphylococcus intermedius* group. SpEX shares 71.8% amino acid identity with *Staphylococcus intermedius* and 73.5% amino acid identity with *Staphylococcus delphini.*

The SpEX protein sequence contains a signal peptide sequence from positions 1 through 35 detected by SignalP 4.1 server. By searching protein family and domain databases Interpro, Pfam and PROSITE, we found that SpEX has an N-terminal oligonucleotide/oligosaccharide binding (OB-fold) domain in residues 43-126 that folds into a five-stranded beta-barrel and a C-terminal β grasp domain in residues 150-217 (FIG. 24). Pairwise alignment with SSL11 and SpEX in addition to the SpEX model developed with the Phyre$^2$ web portal showed that both *S. pseudintermedius* SpEX and SSL11 share the same domain structure (FIG. 24).

SpEX has approximately 47% amino acid sequence identity with staphylococcal superantigen-like protein 11 (SSL11) and less than 30% amino acid identity with other SSL members.

Cloning, Expression, and Purification of Recombinant *S. pseudintermedius* SpEX

Recombinant polyhistidine tagged native and mutant SpEX were generated in *E. coli* and purified using HisPur Ni-NTA resin under native conditions and eluted using an imidazole gradient. The molecular weights of SpEX and SpEX-M determined in western blots were of the expected sizes (27.63 and 27.49 kDa, respectively).

SpEX Interferes with Complement Function

The HRP-conjugated anti-6×his tag monoclonal antibody detected recombinant SpEX bound to human C5. SpEX was significantly bound to human C5 compared to SpEX-M at the same dilution (500 ng/ml with $P<0.0013$) (FIG. 25**A).

Moreover, SpEX in hemolytic assays with bovine erythrocytes caused inhibition of hemolysis at a concentration dependent manner. Starting at concentration of 500 ng, we found that SpEX significantly reduced the hemolysis of sensitized bovine erythrocytes compared to positive control with $P<0.0001$**. SpEX at concentration of 4 μg showed no significant difference in hemolysis with the negative control (FIG. 25**B).

SpEX Inhibits PMN Chemotaxis

Figure 26:
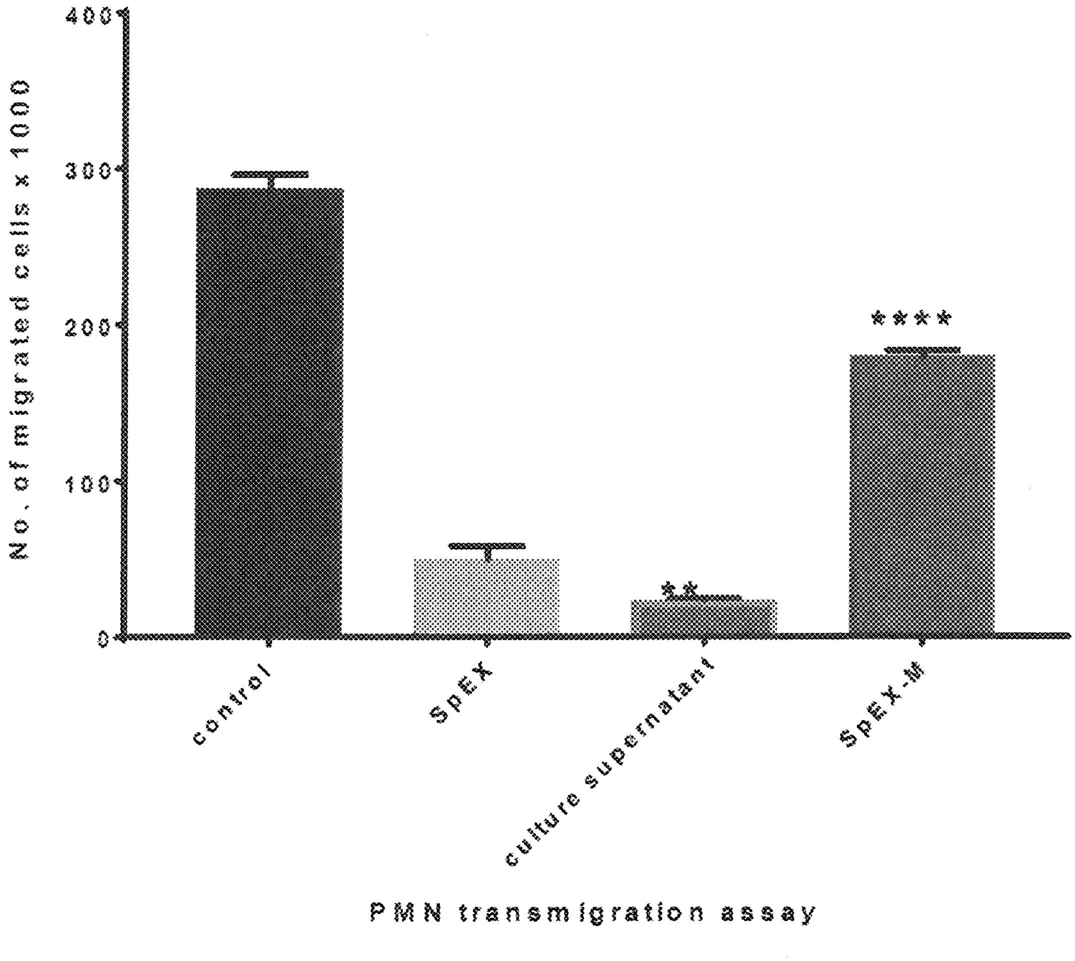
FIG. 26: PMN transmigration assay. Recombinant SpEX at concentration of 200 ng/ml significantly inhibit the migration of PMNs induced by fetal bovine serum compared to SpEX-M at the same dilution with P<0.0001****). The chemotaxis inhibition by culture supernatant of *S. pseudintermedius* 06-3228 was significantly higher than SpEX P<0.0060**. The values represent averages from three independent experiments. (*P<0.05 was considered significant).

The PMN transmigration assay was used to detect the inhibitory effect of recombinant SpEX on PMNs chemotaxis in vitro. Recombinant SpEX at concentration of 200 ng/ml significantly inhibited the migration of PMNs induced by fetal bovine serum compared to SpEX-M at the same dilution with $P<0.0001$****. The chemotaxis inhibition by culture supernatant of *S. pseudintermedius* 06-3228 was significantly higher than SpEX $P<0.0060$ (FIG. 26**).

Attenuated SpEX Induces Specific Antibody Responses

Figure 27:
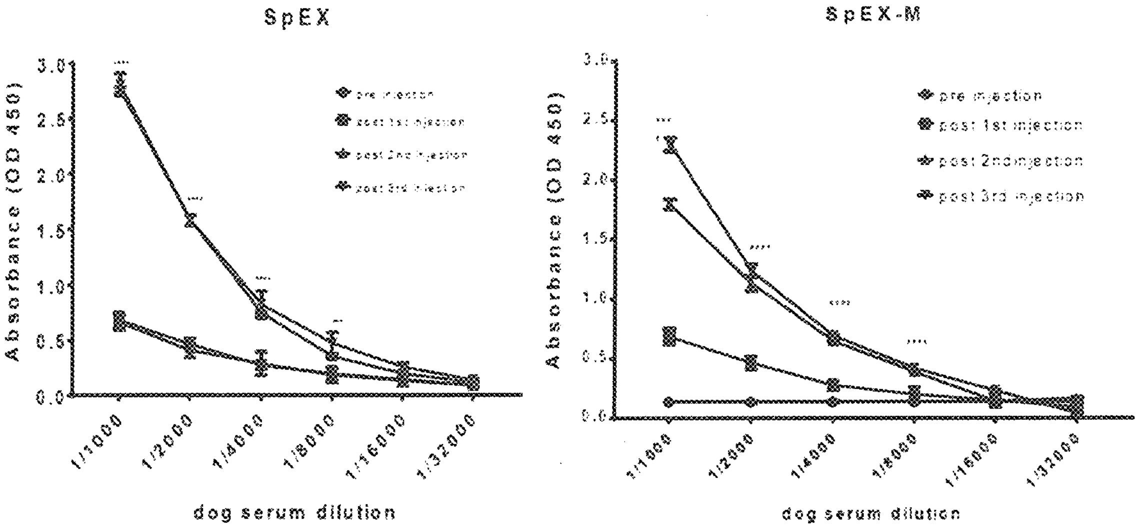
FIG. 27: Canine anti-SpEX-M react with recombinant native SpEX and SpEX-M. Antibodies against *S. pseudintermedius* native SpEX and SpEX-M were detected using an indirect ELISA. Recombinant *S. pseudintermedius* SpEX and SpEX-M proteins were coated on ELISA plates, then incubated with two-fold serially diluted serum from dog vaccinated with the same proteins. High reactivity with SpEX and SpEX-M was seen from sera collected two weeks after 3$^{rd}$ injections of SpEX-M (P=0.0001****) compared to pre-injection sera. The values represent averages from three independent experiments.

ELISA analysis of sera obtained from dogs on days −7, 8, 15 and 29 (relative to injections) showed that IgG against *S. pseudintermedius* SpEX-M (SEQ ID NO:12) and SpEX was detected on day 15 ($P<0.0001$**) and reached the highest level on day 29 ($P<0.0001$) compared to pre-injection control sera (FIG. 27**).

SpEX Kills Canine PMNs and PBMCs

Figure 28:
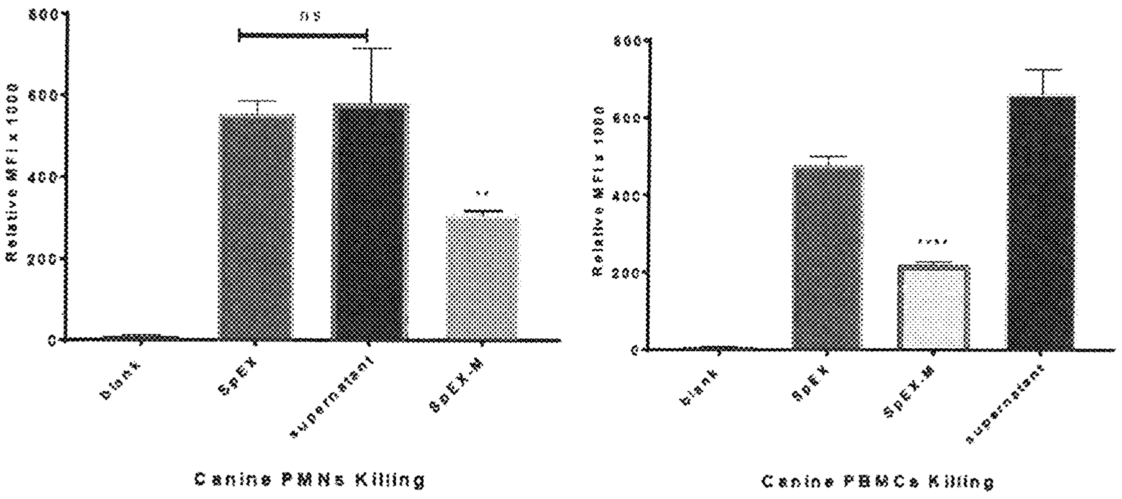
FIG. 28: *S. pseudintermedius* recombinant SpEX has a cytotoxic effect on canine PBMCs and PMNs. The MFI of the SpEX-M relative to SpEX was significantly lower in PMNs (P=0.0052) and PBMCs (P=0.0001**) permeability assays. The values calculated based on average values from three independent experiments (*P<0.05 was considered significant).

Canine PMNs and PBMCs were highly susceptible to SpEX with lysis induced within 30 minutes at a concentration of 100 μg/ml of PBS (pH 7.2) of recombinant SpEX and a 1:2 *S. pseudintermedius* 06-3228 supernatant dilution (FIG. 28). SpEX-M showed a diminished killing effect on PMNs ($P=0.0052$) and PBMCs of dogs ($P<0.0001$) (FIG. 28**).

Canine Anti SpEX-M Reduce the Effect of SpEX on PMNS and PBMCs In Vitro

Figure 29:
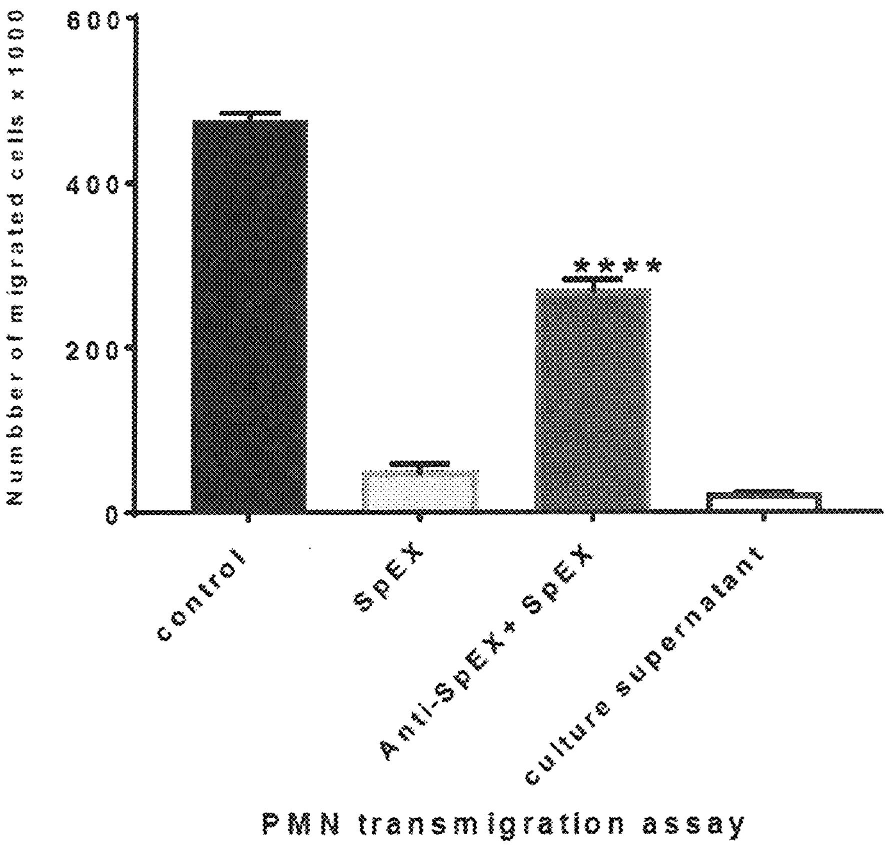
FIG. 29: Pre-incubation of Canine anti-SpEX with SpEX at a concentration of 100 μg/ml in PBS resulted in reduction in mean fluorescent intensity (MFI) as compared with that of SpEX treatment alone.

Canine anti-SpEX at dilution of 1:100 in PBS (pH 7.2) preincubated with recombinant SpEX at concentration of 200 ng/ml significantly diminished the chemotaxis inhibition of SpEX with $P<0.0001$** (FIG. 29**).

Pre-incubation of Canine anti-SpEX with SpEX at a concentration of 100 μg/ml in PBS resulted in reduction in mean fluorescent intensity (MFI) as compared with that of SpEX treatment alone (FIG. 29).

Discussion

Using mass spectrometry and genomic information, it was possible to identify an exotoxin secreted by all of the *S. pseudintermedius* isolates including 06-3221, 08-1661 and NA45, representing the three distinct sequence types that predominate in the United States. In this study, we identified *S. pseudintermedius* SpEX, an exotoxin secreted by *S. pseudintermedius*. Despite the sequence difference, SpEX has a typical SSLs tertiary structure consisting of an N-terminal oligonucleotide/oligosaccharide binding (OB-fold) domain that folds into a five-stranded beta-barrel and a C-terminal β grasp domain. *S. aureus* SSLs are a family of structurally related molecules that exert an entirely different function through a variety of structural mechanisms this explains why we found SpEX in addition to sharing the chemotaxis inhibitor property of SSL11, it has a cytotoxic effect against PBMCs and PMNs and complement activity inhibition through C5 binding. SpEX target components of innate immunity by binding complement factor C5, inhibits complement activation. SpEX is a chemotaxis inhibitor and cytotoxic against dog PMNs and PBMCs that has come into infection sites. The combination of these mechanisms effectively help the bacteria to survive and multiply in their hosts and increase the likelihood of transmission.

Canine antibodies to SpEX efficiently neutralize and diminish its chemotaxis inhibitory and cytotoxic effect on PMNs and PBMCs highlighting the likely immune-evasive attribute of *S. pseudintermedius* SpEX in the dog. Furthermore, SpEX-M (SEQ ID NO:12) with amino acid substitutions in its predicted functional domains showed diminished immune evasive properties compared to SpEX.

Example 7—Vaccine Using Recombinant Attenuated *S. pseudintermedius* Immunosuppressive Proteins in Healthy Dogs A vaccine composition was made comprising recombinant attenuated *S. pseudintermedius* immunosuppressive proteins as described above. The composition comprised recombinant attenuated *S. pseudintermedius* protein A (SEQ ID NO:2), recombinant attenuated *S. pseudintermedius* leukotoxin S (SEQ ID NO:4), recombinant attenuated *S. pseudintermedius* leukotoxin F (SEQ ID NO:10), recombinant attenuated S. *pseudintermedius* exotoxin 15 (SEQ ID NO:12), and recombinant attenuated *S. pseudintermedius* spdsa (SEQ ID NO:6).

Figure 30:
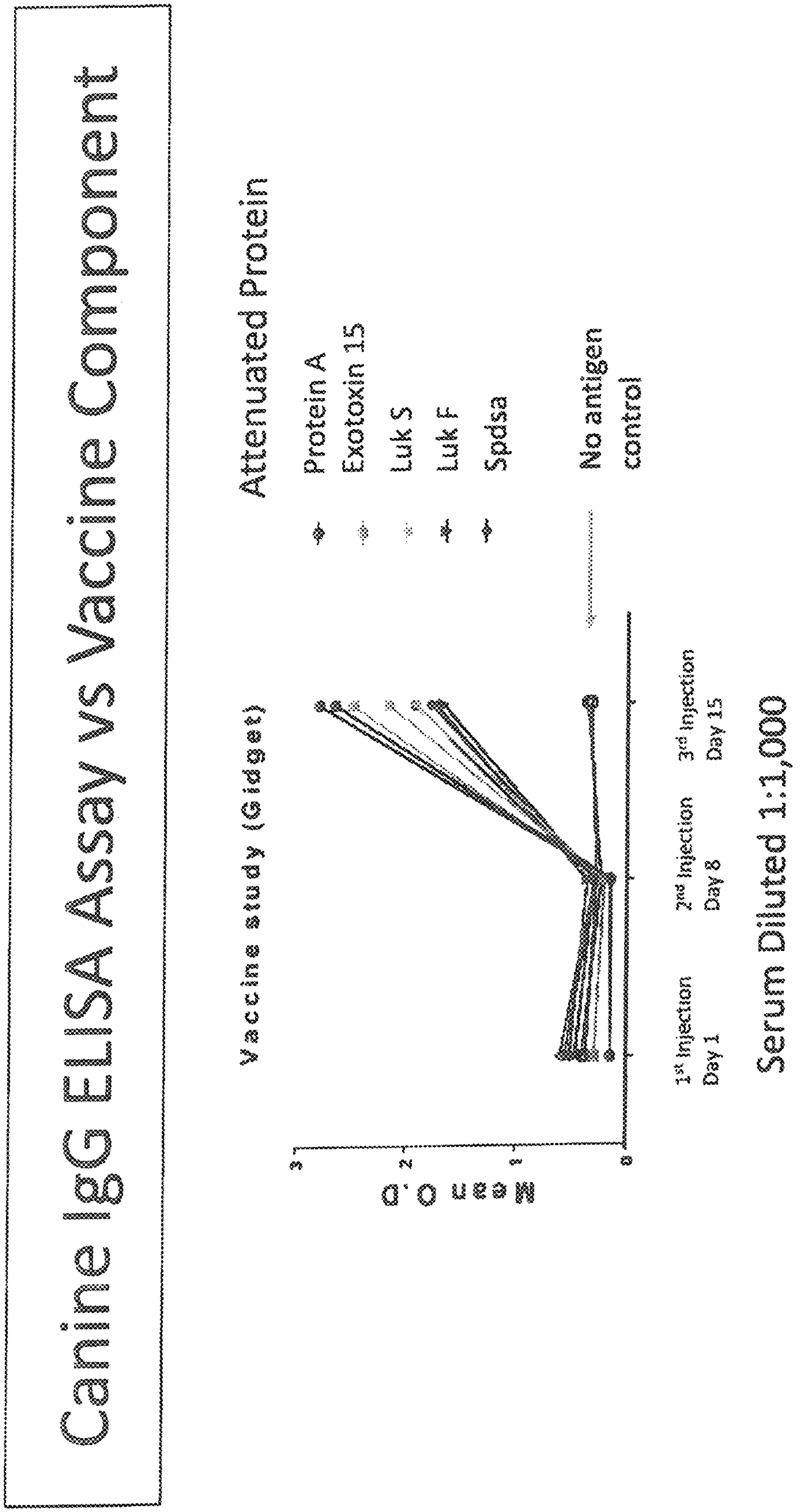
FIG. 30: Result of vaccinating a healthy dog with a vaccine including recombinant attenuated *S. pseudintermedius* protein A (SEQ ID NO:2), recombinant attenuated *S. pseudintermedius* leukotoxin S (SEQ ID NO:4), recombinant attenuated *S. pseudintermedius* leukotoxin F (SEQ ID NO:10), recombinant attenuated *S. pseudintermedius* exotoxin 15 (SEQ ID NO:12), and recombinant attenuated *S. pseudintermedius* spdsa (SEQ ID NO:6).

The compositions were administered individually and as a mixture to healthy research dogs in a series of 3 vaccinations at one-week intervals. Serum was collected pre-vaccination and at weeks 1, 2, 3, and 5 post-vaccination. Canine IgG response to the vaccine was determined by an ELISA assay substantially as described above. The vaccine elicited significant increases in IgG to each of the vaccine components compared to a control comprising no antigen (FIG. 30).

Figure 31:
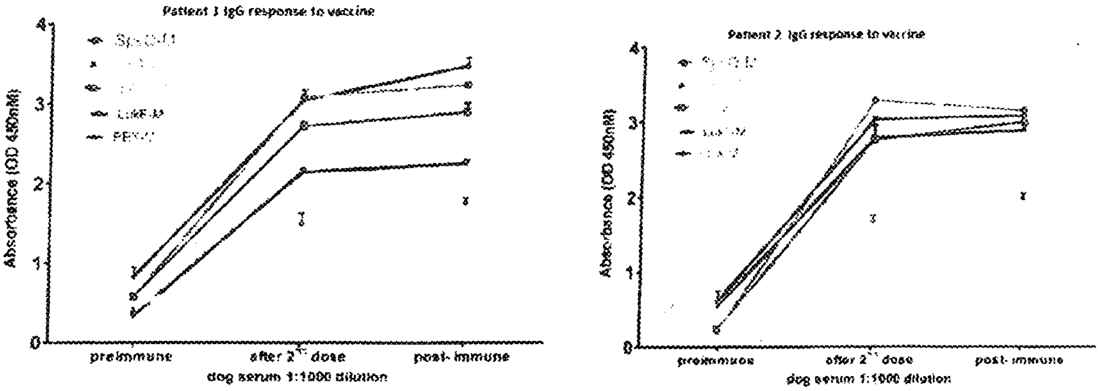
FIG. 31: Result of vaccinating dogs exhibiting pyoderma with a vaccine including recombinant attenuated *S. pseudintermedius* protein A (SEQ ID NO:2), recombinant attenuated *S. pseudintermedius* leukotoxin S (SEQ ID NO:4), recombinant attenuated *S. pseudintermedius* leukotoxin F (SEQ ID NO:10), recombinant attenuated *S. pseudintermedius* exotoxin 15 (SEQ ID NO:12), and recombinant attenuated *S. pseudintermedius* spdsa (SEQ ID NO:6).

Example 8—Vaccine Using Recombinant Attenuated *S. pseudintermedius* Immunosuppressive Proteins in Infected Dogs Dogs with pyoderma were cultured to confirm *S. pseudintermedius* infections. Blood was obtained prior to injection and dogs were vaccinated with a vaccine comprising 20 μg each of recombinant attenuated immunosuppressive proteins as set forth in EXAMPLE 7. Antibody reactivity prior to and after injections was determined by ELISA using HRP conjugated anti-canine IgG. Infected dogs had low levels of antibody prior to injection and a strong antibody response to the vaccine (FIG. 31).

Any citations and published gene sequences referred to in this application form a part of the disclosure and are incorporated herein in their entirety by reference. While the terms used herein are believed to be well-understood by one of ordinary skill in the art, definitions are set forth to facilitate explanation of certain of the presently-disclosed subject matter.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter. With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, S, C, and/or O" includes A, S, C, and O individually, but also includes any and all combinations and subcombinations of A, S, C, and O.

The term "antibody" (Ab) as used herein includes monoclonal antibodies, polyclonal antibodies, multispecific antibodies and antibody fragments, as long as they exhibit the desired biological activity. The term "polyclonal antibody" as used herein refers to an antibody obtained from a population of heterogeneous antibodies, i.e., they are secreted by different B cell lineages within the body. The term "monoclonal antibody" as used herein refers to an antibody obtained from a population of substantially homogeneous antibodies, i.e., the individual antibodies that make up the population are identical except for possible naturally occurring mutations. Monoclonal antibodies are highly specific, being directed against a single antigenic site.

The term "antibody" (Ab) as used herein also includes antibody fragments. An "antibody fragment" is a portion of an intact antibody, preferably the antigen binding or variable region of the intact antibody. Examples of antibody fragments include but are not limited to: Fab, Fab', $F(ab')_2$, and Fv fragments; diabodies; linear antibodies; single-chain antibody molecules; and multispecific antibodies formed from antibody fragments.

The foregoing description of preferred embodiments has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the disclosed subject matter and its practical application to thereby enable one of ordinary skill in the art to utilize the invention in various embodiments and with various modifications as are suited to the particular use contemplated. All such modifications and variations are within the scope of the invention as determined by the claims when interpreted in accordance with the breadth to which they are fairly, legally and equitably entitled.

What is claimed is:

1. A multivalent immunogenic therapeutic composition, comprising one or more recombinant proteins selected from the group consisting of an attenuated immunoevasive *Staphylococcus pseudintermedius* Protein A (SEQ ID NO:2) and an attenuated immunoevasive *Staphylococcus pseudintermedius* Leukotoxin S (SEQ ID NO:4).

2. The multivalent immunogenic therapeutic composition of claim 1, further comprising an attenuated immunoevasive *Staphylococcus pseudintermedius* Nucleotidase adenosine synthase protein (AdsA) (SEQ ID NO:6).

3. The multivalent immunogenic therapeutic composition of claim 1, further comprising an attenuated immunoevasive *Staphylococcus pseudintermedius* coagulase (SEQ ID NO:8).

4. The multivalent immunogenic therapeutic composition of claim 1, further comprising an attenuated immunoevasive *Staphylococcus pseudintermedius* Leukotoxin F (SEQ ID NO:10).

5. The multivalent immunogenic therapeutic composition of claim 1, further comprising an attenuated immunoevasive *Staphylococcus pseudintermedius* exotoxin 15 (SEQ ID NO:12).

6. A multivalent immunogenic therapeutic composition, consisting essentially of a recombinant attenuated immunoevasive *Staphylococcus pseudintermedius* Protein A (SEQ ID NO:2), a recombinant attenuated immunoevasive *Staphylococcus pseudintermedius* Leukotoxin S (SEQ ID NO:4), a recombinant attenuated immunoevasive *Staphylococcus pseudintermedius* Nucleotidase adenosine synthase protein (AdsA) (SEQ ID NO:6), a recombinant attenuated immunoevasive *Staphylococcus pseudintermedius* coagulase (SEQ ID NO:8), a recombinant attenuated immunoevasive *Staphylococcus pseudintermedius* Leukotoxin F (SEQ ID NO:10), and a recombinant attenuated immunoevasive *Staphylococcus pseudintermedius* exotoxin 15 (SEQ ID NO:12); and optionally, one or more suitable pharmaceutical or veterinary excipients and carriers.

7. A multivalent chimeric protein comprising the sequence set forth as SEQ ID NO: 14.

8. An immunogenic composition, comprising:

one or more recombinant proteins selected from the group consisting of a recombinant attenuated *Staphylococcus pseudintermedius* Protein A (SEQ ID NO:2) and a recombinant attenuated *Staphylococcus pseudintermedius* Leukotoxin S (SEQ ID NO:4); and one or more of a suitable pharmaceutical or veterinary adjuvant, a suitable pharmaceutical or veterinary excipient, and a suitable pharmaceutical or veterinary carrier.

9. The immunogenic composition of claim 8, further comprising a recombinant attenuated *Staphylococcus pseudintermedius* Nucleotidase adenosine synthase protein (AdsA) (SEQ ID NO:6).

10. The immunogenic composition of claim 8, further comprising a recombinant attenuated *Staphylococcus pseudintermedius* coagulase (SEQ ID NO:8).

11. The immunogenic composition of claim 8, further comprising a recombinant attenuated *Staphylococcus pseudintermedius* Leukotoxin F (SEQ ID NO:10).

12. The immunogenic composition of claim 8, further comprising a recombinant attenuated *Staphylococcus pseudintermedius* exotoxin 15 (SEQ ID NO:12).

13. An immunogenic composition, consisting essentially of a recombinant attenuated *Staphylococcus pseudintermedius* Protein A (SEQ ID NO:2), a recombinant attenuated *Staphylococcus pseudintermedius* Leukotoxin S (SEQ ID NO:4), a recombinant attenuated *Staphylococcus pseudintermedius* Nucleotidase adenosine synthase protein (AdsA) (SEQ ID NO:6), a recombinant attenuated *Staphylococcus pseudintermedius* coagulase (SEQ ID NO:8), a recombinant attenuated *Staphylococcus pseudintermedius* Leukotoxin F (SEQ ID NO:10), and a recombinant attenuated *Staphylococcus pseudintermedius* exotoxin 15 (SEQ ID NO:12); and one or more of a suitable pharmaceutical or veterinary adjuvant, a suitable pharmaceutical or veterinary excipient, and a suitable pharmaceutical or veterinary carrier.

* * * * *

UNITED STATES PATENT AND TRADEMARK OFFICE

CERTIFICATE OF CORRECTION

PATENT NO. : 11,141,473 B2
APPLICATION NO. : 16/636682
DATED : October 12, 2021
INVENTOR(S) : Stephen A. Kania, David Bemis and Mohamed A. Abouelkhair It is certified that error appears in the above-identified patent and that said Letters Patent is hereby corrected as shown below:

In the Specification

At Column 1, Lines 14-18, please replace the REFERENCE TO SEQUENCE LISTING SUBMITTED ELECTRONICALLY paragraph with the following replacement paragraph:
A sequence listing electronically submitted with the present application as an ASCII text file named 1101-016US01ReplacementSequenceListing_ST25.txt, created on 08-06-2024 and having a size of 73,547 bytes, is incorporated herein by reference in its entirety.

Signed and Sealed this
Fifth Day of November, 2024

Katherine Kelly Vidal

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 1272
<212> TYPE: DNA
<213> ORGANISM: Artificial Sequence
```

<220> FEATURE:
<223> OTHER INFORMATION: S. pseudintermedius protein A synthetic gene
      optimized for expression in E.coli

<400> SEQUENCE: 1

```
attggcggaa ggccgtcaag gccgcatgag ctcgcatgag gatccaagct ttgccgaaga     60

aggtgataat aacgccgaag ccaaaaaaaa cgcatttagc gaagttgtga aactgccgaa    120

tctgagcgaa gaacagcgta atggttttat tcagagcctg aaagcagcac cgagcaccag    180

ccaggatgtt ctgaatgaag caaaaaaact gaacgatagc caagaaggta gccagcctgc    240

accggattat agtgatgaaa aaaagaacgc cttctatgaa attctgcatc tgccgaattt    300

gacagaggaa caacgcaatg gttatatcca gtcattaaaa gccgcaccgt cagttagcgc    360

aaatattctg gttgaagcga aaaacatgaa cgttaatcag accccgacac aaccggcacc    420

gagctttgat gaagcgaaga aaaatgcctt ttacgagatt gttaacctgc cgaacttaac    480

cgaagaacaa agaaacggct ttatccaaag tcttaaagca gctccgtctg tgagcaaaga    540

tatcctggtg gaagccaaga aactgaatga ttctcaggca aaaccggatt acaacgaggc    600

aaaaaagaat gcattttatg agatccttca ccttccgaac ctgactgagg aacagagaaa    660

tggattcatt cagtctctga aggctgcacc gagtgttagc agcgatattc tggcagaggc    720

caaaaaactt aatgacagcc aggcaccgaa agaggataac aacgttaaag ataataacag    780

cggtgagaac aaagccgaag ataaaggcaa taaagaaaac aaggcagagg acaaaggtag    840

caaagaagat aaggccgagg ataagggttc aaaagaggac aaggcggaag ataagggctc    900

taaagaagat aaagccaaag acaaggataa caaagaaggt aaagcagccg ataaaggtat    960

ggacaaagca aaagatgcaa tgcatgttgt tcagcctggt gaaaccgttg aaaaaattgc   1020

caaagcaaat aacaccaccg ttgagcagat tgcgaaagat aatcatcttg aggacaagaa   1080

catgattctg cctggtcaga aactggttgt ggataatcag aaagcaatga aggattccaa   1140

agaagccaaa gccaatcacg aaatgaaagc actgccggaa acaggtgaag aaaatgatat   1200

ggcactgttc ggtgcggccg ctcatgcggt accctgggcc tcatgggcct tccgctcacg   1260

ccttccgctc ac                                                       1272
```

<210> SEQ ID NO 2
<211> LENGTH: 393
<212> TYPE: PRT
<213> ORGANISM: artificial sequence
<220> FEATURE:
<223> OTHER INFORMATION: S. pseudintermedius attenuated Protein A

<400> SEQUENCE: 2

```
Pro Ser Phe Ala Glu Glu Gly Asp Asn Asn Ala Glu Ala Lys Lys Asn
1               5                   10                  15

Ala Phe Ser Glu Val Val Lys Leu Pro Asn Leu Ser Glu Glu Gln Arg
            20                  25                  30

Asn Gly Phe Ile Gln Ser Leu Lys Ala Ala Pro Ser Thr Ser Gln Asp
        35                  40                  45

Val Leu Asn Glu Ala Lys Lys Leu Asn Asp Ser Gln Glu Gly Ser Gln
    50                  55                  60

Pro Ala Pro Asp Tyr Ser Asp Glu Lys Lys Asn Ala Phe Tyr Glu Ile
65                  70                  75                  80

Leu His Leu Pro Asn Leu Thr Glu Glu Gln Arg Asn Gly Tyr Ile Gln
                85                  90                  95
```

-continued

```
Ser Leu Lys Ala Ala Pro Ser Val Ser Ala Asn Ile Leu Val Glu Ala
            100                 105                 110

Lys Asn Met Asn Val Asn Gln Thr Pro Thr Gln Pro Ala Pro Ser Phe
        115                 120                 125

Asp Glu Ala Lys Lys Asn Ala Phe Tyr Glu Ile Val Asn Leu Pro Asn
    130                 135                 140

Leu Thr Glu Glu Gln Arg Asn Gly Phe Ile Gln Ser Leu Lys Ala Ala
145                 150                 155                 160

Pro Ser Val Ser Lys Asp Ile Leu Val Glu Ala Lys Lys Leu Asn Asp
                165                 170                 175

Ser Gln Ala Lys Pro Asp Tyr Asn Glu Ala Lys Lys Asn Ala Phe Tyr
            180                 185                 190

Glu Ile Leu His Leu Pro Asn Leu Thr Glu Glu Gln Arg Asn Gly Phe
        195                 200                 205

Ile Gln Ser Leu Lys Ala Ala Pro Ser Val Ser Ser Asp Ile Leu Ala
    210                 215                 220

Glu Ala Lys Lys Leu Asn Asp Ser Gln Ala Pro Lys Glu Asp Asn Asn
225                 230                 235                 240

Val Lys Asp Asn Asn Ser Gly Glu Asn Lys Ala Glu Asp Lys Gly Asn
                245                 250                 255

Lys Glu Asn Lys Ala Glu Asp Lys Gly Ser Lys Glu Asp Lys Ala Glu
            260                 265                 270

Asp Lys Gly Ser Lys Glu Asp Lys Ala Glu Asp Lys Gly Ser Lys Glu
        275                 280                 285

Asp Lys Ala Lys Asp Lys Asp Asn Lys Glu Gly Lys Ala Ala Asp Lys
    290                 295                 300

Gly Met Asp Lys Ala Lys Asp Ala Met His Val Val Gln Pro Gly Glu
305                 310                 315                 320

Thr Val Glu Lys Ile Ala Lys Ala Asn Asn Thr Thr Val Glu Gln Ile
                325                 330                 335

Ala Lys Asp Asn His Leu Glu Asp Lys Asn Met Ile Leu Pro Gly Gln
            340                 345                 350

Lys Leu Val Val Asp Asn Gln Lys Ala Met Lys Asp Ser Lys Glu Ala
        355                 360                 365

Lys Ala Asn His Glu Met Lys Ala Leu Pro Glu Thr Gly Glu Glu Asn
    370                 375                 380

Asp Met Ala Leu Phe Gly Ala Ala Ala
385                 390
```

<210> SEQ ID NO 3
<211> LENGTH: 1037
<212> TYPE: DNA
<213> ORGANISM: artificial sequence
<220> FEATURE:
<223> OTHER INFORMATION: S. pseduintermedius Leukotoxin S synthetic gene optimized for expression in E.coli

<400> SEQUENCE: 3

```
cgaattggcg gaaggccgtc aaggccacgt gtcttgtcca gagctcggat ccaatggtga      60

aaaacaaact gctggcagca accctgagca ttagcctggt tctgccgctg attaccccgt     120

atagcgaaga agcaaaagca gcaaatacca ttgaagaaat tggtgaaggt gcccagatta     180

tcaaacgtac cgaagatgtt agcagccgta aatggggtgt ttttcagaac atccagttcg     240

attttgtgaa agacccgaaa tataataagg acgccctgat cattaaaatg cagggcttta     300

tcaaaagccg taccagcttt accgatgtga aaggtaaagg ttatgaaagc accaaacgta     360
```

-continued

```
tgctgtggcc gtttcagtat aacattgcac tgaaaaccaa tgatccgaat gtgagcctga    420

tcaattatct gcctgcaaac aaaattgaga gcatcgatgt tagtcagacc ctgggttata    480

atgttggtgg taattttcag agcgcaccgc tgttaggtgg taaaggtgca tttaactaca    540

gcaagaaaat cagctacacc cagaaaaact atattagcga agttgcacag cagaacagca    600

aaaacattcg ttgggaagtt aaagccaaca gctttaatac cgaaaatggt caggttagcg    660

catatgatcg tcacctgttt gttcgtagcc cgattggtcc gaatgcacgt gatttttttg    720

ttccgaatga tgaactgcct ccgctgattc agagcggttt taatccggca tttattgcaa    780

ccgttagcca cgaaaaagat aaaggtgata ccagcgaatt tgaaattgcc tatggtcgca    840

atctggatat tacctatgca accttttttc cgcgtaccgg tatttttgca gaacgtcgtc    900

ataatgcact gatgaatcgt aatctggtga ccaaatatga ggtgaactgg aaaacccatg    960

agatcaaagt gaaaggccac aatgcggccg cggtacctgg agcacaagac tggcctcatg   1020

ggccttccgc tcactgc                                                  1037


<210> SEQ ID NO 4
<211> LENGTH: 424
<212> TYPE: PRT
<213> ORGANISM: artificial sequence
<220> FEATURE:
<223> OTHER INFORMATION: S. pseuduintermedius attenuated  Leukotoxin S

<400> SEQUENCE: 4

Ala Thr Thr Thr Thr Thr Gly Cys Ala Gly Ala Ala Cys Gly Thr Cys
1               5                   10                  15

Gly Thr Cys Ala Thr Ala Ala Thr Gly Cys Ala Cys Thr Gly Ala Thr
            20                  25                  30

Gly Ala Ala Thr Cys Gly Thr Ala Ala Thr Cys Thr Gly Gly Thr Gly
        35                  40                  45

Ala Cys Cys Ala Ala Ala Thr Ala Thr Gly Ala Gly Gly Thr Gly Ala
    50                  55                  60

Ala Cys Thr Gly Gly Ala Ala Ala Ala Cys Cys Cys Ala Thr Gly Ala
65                  70                  75                  80

Gly Ala Thr Cys Ala Ala Ala Gly Thr Gly Ala Ala Ala Gly Gly Cys
                85                  90                  95

Cys Ala Cys Ala Ala Thr Gly Cys Gly Gly Cys Cys Gly Cys Gly Ser
            100                 105                 110

Met Val Lys Asn Lys Leu Leu Ala Ala Thr Leu Ser Ile Ser Leu Val
        115                 120                 125

Leu Pro Leu Ile Thr Pro Tyr Ser Glu Glu Ala Lys Ala Ala Asn Thr
    130                 135                 140

Ile Glu Glu Ile Gly Glu Gly Ala Gln Ile Ile Lys Arg Thr Glu Asp
145                 150                 155                 160

Val Ser Ser Arg Lys Trp Gly Val Phe Gln Asn Ile Gln Phe Asp Phe
                165                 170                 175

Val Lys Asp Pro Lys Tyr Asn Lys Asp Ala Leu Ile Ile Lys Met Gln
            180                 185                 190

Gly Phe Ile Lys Ser Arg Thr Ser Phe Thr Asp Val Lys Gly Lys Gly
        195                 200                 205

Tyr Glu Ser Thr Lys Arg Met Leu Trp Pro Phe Gln Tyr Asn Ile Ala
    210                 215                 220

Leu Lys Thr Asn Asp Pro Asn Val Ser Leu Ile Asn Tyr Leu Pro Ala
225                 230                 235                 240
```

-continued

```
Asn Lys Ile Glu Ser Ile Asp Val Ser Gln Thr Leu Gly Tyr Asn Val
                245                 250                 255

Gly Gly Asn Phe Gln Ser Ala Pro Leu Leu Gly Gly Lys Gly Ala Phe
            260                 265                 270

Asn Tyr Ser Lys Lys Ile Ser Tyr Thr Gln Lys Asn Tyr Ile Ser Glu
        275                 280                 285

Val Ala Gln Gln Asn Ser Lys Asn Ile Arg Trp Glu Val Lys Ala Asn
    290                 295                 300

Ser Phe Asn Thr Glu Asn Gly Gln Val Ser Ala Tyr Asp Arg His Leu
305                 310                 315                 320

Phe Val Arg Ser Pro Ile Gly Pro Asn Ala Arg Asp Phe Phe Val Pro
                325                 330                 335

Asn Asp Glu Leu Pro Pro Leu Ile Gln Ser Gly Phe Asn Pro Ala Phe
            340                 345                 350

Ile Ala Thr Val Ser His Glu Lys Asp Lys Gly Asp Thr Ser Glu Phe
        355                 360                 365

Glu Ile Ala Tyr Gly Arg Asn Leu Asp Ile Thr Tyr Ala Thr Phe Phe
    370                 375                 380

Pro Arg Thr Gly Ile Phe Ala Glu Arg Arg His Asn Ala Leu Met Asn
385                 390                 395                 400

Arg Asn Leu Val Thr Lys Tyr Glu Val Asn Trp Lys Thr His Glu Ile
                405                 410                 415

Lys Val Lys Gly His Asn Ala Ala
            420
```

```
<210> SEQ ID NO 5
<211> LENGTH: 1470
<212> TYPE: DNA
<213> ORGANISM: artificial sequence
<220> FEATURE:
<223> OTHER INFORMATION: S. pseuduintermedius Nucleotidase ADsA
      synthetic gene optimized for expression in E.coli

<400> SEQUENCE: 5

atgctgcgtc tgagcgcaaa aaaagcacag ccggaagcaa ccagcattga tcgtgcaagc     60

catgaaaccg cagcaaccac acataccatt ctgcatacca atgcaattgc cggtcgtatg    120

gttgaagaaa aagatcgtgt tttaggtatg gccaaactga aaccctgaa agaacagcag    180

aacccggatc tgctggttga tgccggtgat gcatttcagg gtctgccgct gagcaatcag    240

agcaaaggtg aagaaatggc aaaagcaatg aatgccgttg gttatgatgc aatgaccgca    300

ggtaatgcag aatttgcctt tggctatgat cagctgaaaa aactggaagg catgctgaat    360

tttccgattg ttagcagcaa cgtgtataaa gatggtaaac tggcatttaa accgagcgtg    420

gtgattcaga aaaatggtgt tcgttatggt gtgattggtg ttaccacacc ggaaaccaaa    480

acaaaaacca gtccgaaagg tattgttggt gtgacctttg cagatccgct gaccagcgtt    540

acccgtgaaa tggatcgtct gaatggtcag gttgatgttt ttattgttct gagccatctg    600

ggtattgatc cgaccaccaa agaagcatgg cgaggcgatt atctgacccg tcagctgagc    660

cagaataaac agtatcatca tccgatcttt gtgatcgatg gtcatagcca taccgttatt    720

gaacatggcc agaaatttga tcaggatgtt ctggcacaga ccggcaccgc actggcaaat    780

gtgggtaaac tgaccttcaa acagagcggt cagcagttta gcaatgccga agcaagcctg    840

ctgaatgtta aaaatctggc aaaactgcag ccggatgcag cagttaaagc acaggttgat    900

aaagcaaatg aagcctttct gaaagcgacc agcgaagtta ttattccgaa taacaccgtt    960
```

-continued

```
gattttcagg gcgaacgtga tgatgttcgt acccatgaaa caaatctggg taatgcaatt   1020

accgatgcaa tggaagcata tggtcagaaa ggttttagcc gtccgagcga ttttgcagtt   1080

accaatagcg gtggtattcg tgccagcatt gcaaaaggta aagttaccct gaatgatgtg   1140

attaccgttc tgccgtttgg taataccatt gcacagatta gcgttaaagg ttccgatgtt   1200

tggaaagcct ttgaacatag cctgagcgca ccgaccatga ccacaggtgg tgaaacccag   1260

ctgagcgcca atggtggtct gctgcaggtt agcaaaagca ttcaggttta tttcgacatg   1320

aataaagcac cgggtgaacg tattaatgcc attcgtgttc tgaacaaaca gacaggccag   1380

tttgaagatc tggatatgag ccgtacctat gcagttgcca tgaatgattt taccgcaagc   1440

ggtggtgcag cagcacatgc aaatgcatat                                    1470
```

<210> SEQ ID NO 6
<211> LENGTH: 490
<212> TYPE: PRT
<213> ORGANISM: artificial sequence
<220> FEATURE:
<223> OTHER INFORMATION: S. pseduintermedius attenuated Nucleotidase ADsA

<400> SEQUENCE: 6

```
Met Leu Arg Leu Ser Ala Lys Lys Ala Gln Pro Glu Ala Thr Ser Ile
1               5                   10                  15

Asp Arg Ala Ser His Glu Thr Ala Ala Thr Thr His Thr Ile Leu His
            20                  25                  30

Thr Asn Ala Ile Ala Gly Arg Met Val Glu Glu Lys Asp Arg Val Leu
        35                  40                  45

Gly Met Ala Lys Leu Lys Thr Leu Lys Glu Gln Gln Asn Pro Asp Leu
    50                  55                  60

Leu Val Asp Ala Gly Asp Ala Phe Gln Gly Leu Pro Leu Ser Asn Gln
65                  70                  75                  80

Ser Lys Gly Glu Glu Met Ala Lys Ala Met Asn Ala Val Gly Tyr Asp
                85                  90                  95

Ala Met Thr Ala Gly Asn Ala Glu Phe Ala Phe Gly Tyr Asp Gln Leu
            100                 105                 110

Lys Lys Leu Glu Gly Met Leu Asn Phe Pro Ile Val Ser Ser Asn Val
        115                 120                 125

Tyr Lys Asp Gly Lys Leu Ala Phe Lys Pro Ser Val Val Ile Gln Lys
    130                 135                 140

Asn Gly Val Arg Tyr Gly Val Ile Gly Val Thr Thr Pro Glu Thr Lys
145                 150                 155                 160

Thr Lys Thr Ser Pro Lys Gly Ile Val Gly Val Thr Phe Ala Asp Pro
                165                 170                 175

Leu Thr Ser Val Thr Arg Glu Met Asp Arg Leu Asn Gly Gln Val Asp
            180                 185                 190

Val Phe Ile Val Leu Ser His Leu Gly Ile Asp Pro Thr Thr Lys Glu
        195                 200                 205

Ala Trp Arg Gly Asp Tyr Leu Thr Arg Gln Leu Ser Gln Asn Lys Gln
    210                 215                 220

Tyr His His Pro Ile Phe Val Ile Asp Gly His Ser His Thr Val Ile
225                 230                 235                 240

Glu His Gly Gln Lys Phe Asp Gln Asp Val Leu Ala Gln Thr Gly Thr
                245                 250                 255

Ala Leu Ala Asn Val Gly Lys Leu Thr Phe Lys Gln Ser Gly Gln Gln
            260                 265                 270
```

```
Phe Ser Asn Ala Glu Ala Ser Leu Leu Asn Val Lys Asn Leu Ala Lys
        275                 280                 285

Leu Gln Pro Asp Ala Ala Val Lys Ala Gln Val Asp Lys Ala Asn Glu
    290                 295                 300

Ala Phe Leu Lys Ala Thr Ser Glu Val Ile Ile Pro Asn Asn Thr Val
305                 310                 315                 320

Asp Phe Gln Gly Glu Arg Asp Asp Val Arg Thr His Glu Thr Asn Leu
                325                 330                 335

Gly Asn Ala Ile Thr Asp Ala Met Glu Ala Tyr Gly Gln Lys Gly Phe
            340                 345                 350

Ser Arg Pro Ser Asp Phe Ala Val Thr Asn Ser Gly Gly Ile Arg Ala
        355                 360                 365

Ser Ile Ala Lys Gly Lys Val Thr Leu Asn Asp Val Ile Thr Val Leu
    370                 375                 380

Pro Phe Gly Asn Thr Ile Ala Gln Ile Ser Val Lys Gly Ser Asp Val
385                 390                 395                 400

Trp Lys Ala Phe Glu His Ser Leu Ser Ala Pro Thr Met Thr Thr Gly
                405                 410                 415

Gly Glu Thr Gln Leu Ser Ala Asn Gly Gly Leu Leu Gln Val Ser Lys
            420                 425                 430

Ser Ile Gln Val Tyr Phe Asp Met Asn Lys Ala Pro Gly Glu Arg Ile
        435                 440                 445

Asn Ala Ile Arg Val Leu Asn Lys Gln Thr Gly Gln Phe Glu Asp Leu
    450                 455                 460

Asp Met Ser Arg Thr Tyr Ala Val Ala Met Asn Asp Phe Thr Ala Ser
465                 470                 475                 480

Gly Gly Ala Ala Ala His Ala Asn Ala Tyr
                485                 490


<210> SEQ ID NO 7
<211> LENGTH: 1497
<212> TYPE: DNA
<213> ORGANISM: artificial sequence
<220> FEATURE:
<223> OTHER INFORMATION: S. pseudintermedius coagulase synthetic gene
      optimized for expression in E.coli

<400> SEQUENCE: 7

ggatccaatg atgaaaaaaa agctgctggt tctgagcgca agcgcagttc tggcaagcca     60

ttttctggtt ggtggtgaag ccagcgcagc agcaagcggt gaaaaaaatc cgtataccag    120

caaagcactg agcatcatgg aaaaaagcag caccagcagc gttaccaccg aacagtacaa    180

aaaaagcgca gaaaaagcaa tggcacgtct gaccgcaggc ggttatgaag catatgacga    240

accggcagca gcagccgttg ttaaagcata taaacagcgt tttgcagccg aaatgaatgc    300

catgaatcag tttgcccaag aagagaaagc caaagaaaaa aagaatggtg ccattagcac    360

cgatgcaatt ggtctgaccc atcagcgtta tgataccgca tatgcaagtg ccgaagaaaa    420

cgcaaaagat tttgaacgcg agatcaaaaa actgaacgaa cagcatagcg atctgaaaac    480

ctttaatcgc caagaacaga atgatgcaga tcagaaagca aacgatctgg aaaatcaggc    540

actgatgctg ggccagacct ttatctatca gggtgatgcc attttcaacc tgtataacaa    600

actggatatg agcattggca acctggatta tgaacgggaa gagaaaaaag ccattaacaa    660

acgcatgctg gacaagaaag ttgaggacct ggaaaccatt atcgatgaat tttttgcagc    720

gattgcactg aaacgtccga aagaagcacc ggttctgacc cgtgaaaatg aaaaagatag    780
```

-continued

```
cgcagttaaa gcaaaactgc gtcaggatgc acaggatgcc aaaaatgatg caagcctgcg    840

tcatccgcgt gttctgaaaa agaaaagtac cgatgcaccg agccagccga gcgatcaaga    900

agttgcacag ccgtcagtta atagcattga aattaaagca ccgcaggcag caaccccgaa    960

aaaaccggtt cataccgaaa ccattgttca taccccgatg accgcagttc cgcagaccaa   1020

acatgaagca acctttgaag tgccgcaggg tcgtaatacc cagaccagcg caaccgcaaa   1080

tagcgaacag gcaaccgaaa ccgttgatgt tccgaaagca aatggtcagg ttcagagtga   1140

acaggttacc acaccgggtg ttcagcagac ccatagcatg gcacagcaga gcgaaacacc   1200

gcagccggtt gcagaagaaa ccgaaattat caccgaagca catgttgccg atattgatga   1260

aagcaccacc tttcagaaaa gcggttatct ggcaggcgca agcgaaagcg ataccagcgg   1320

tgcaaccgaa gcagaaaaac gtgcaattcg tcgtgcacat gttcgtgaag cagaagcact   1380

ggcagcacag gcagcagaaa cccatcgtgc ccaggatgca atggcagccc agcagaaagt   1440

tgcaaccctg agcaaagccc atcagaaacg ttttaacaag atgattaacg cggccgc      1497


<210> SEQ ID NO 8
<211> LENGTH: 502
<212> TYPE: PRT
<213> ORGANISM: artificial sequence
<220> FEATURE:
<223> OTHER INFORMATION: S. pseudintermedius  attenuated coagulase

<400> SEQUENCE: 8

Met Lys Lys Lys Leu Leu Val Leu Ser Ala Ser Ala Val Leu Ala Ser
1               5                   10                  15

His Phe Leu Val Gly Gly Glu Ala Ser Ala Ile Val Ser Gly Glu Glu
            20                  25                  30

Asn Pro Tyr Lys Ser Lys Ala Leu Ser Ile Thr Glu Lys Ser Ser Thr
        35                  40                  45

Ser Ser Tyr Thr Ser Glu Gln Tyr Lys Lys Ser Leu Glu Asp Leu Ile
    50                  55                  60

Tyr Lys Leu Thr Ile Ser Gly Tyr Glu Lys Tyr Asp Glu Pro Glu Tyr
65                  70                  75                  80

Ala Ala Ala Val Lys Lys Tyr Gln Gln Arg Phe Met Ala Glu Met Glu
                85                  90                  95

Ala Met Asn Gln Phe Leu Gln Gly Glu Lys Val Lys Glu Arg Lys Arg
            100                 105                 110

Lys Asn Ser Gln Pro Ile Pro Asp Asp Ile Ile Gly Leu Thr Tyr Gln
        115                 120                 125

Arg Tyr Lys Ala Val Tyr Asp Ala Leu Glu Glu Asn Lys Lys Asp Phe
    130                 135                 140

Asp Arg Glu Ile Ala Glu Leu Asn Asp Lys His Pro Glu Leu Lys Thr
145                 150                 155                 160

Phe Asp Ser Lys His Gln Ser Glu Ala Asp Gln Lys Leu Asn Asp Leu
                165                 170                 175

Glu Asn Gln Val Leu Met Leu Gly Lys Thr Phe Ile Arg Lys Asp Glu
            180                 185                 190

Ala Arg Ala Ser Leu Tyr Gln Lys Leu Asp Leu Ser Ile Gly Tyr Thr
        195                 200                 205

Asp Asn Glu Arg Lys Glu Lys Lys Ala Ile Asn Gln Arg Met Leu Asp
    210                 215                 220

Arg Lys Ile Glu Asp Leu Glu Thr Ile Ile Asp Glu Phe Phe Glu Glu
225                 230                 235                 240
```

-continued

```
Ala Asp Leu Ala Arg Pro Lys Glu Ile Pro Val Leu Thr Ala Glu Asn
                245                 250                 255

Glu Tyr Asp Asn Ala Val Lys Asn Lys Leu Arg Glu Asp Ala Asn Lys
            260                 265                 270

Ala Lys Ala Asp Glu Lys Leu Arg His Pro Arg Ala Leu Lys Gln Gln
        275                 280                 285

Ser Ile Asp Ala Pro Ser Gln Pro Ser Asp Gln Glu Val Ala Gln Thr
    290                 295                 300

Ser Val Asn Ser Ile Glu Ile Lys Ala Pro Gln Ala Ala Thr Pro Gln
305                 310                 315                 320

Gln Pro Val His Thr Glu Thr Ile Val His Thr Pro Met Thr Ala Val
                325                 330                 335

Pro Gln Thr Lys His Glu Ala Thr Phe Glu Val Pro Gln Gly Arg Asn
            340                 345                 350

Thr Gln Thr Ser Ala Thr Ala Asn Lys Glu Gln Ala Thr Glu Thr Val
        355                 360                 365

Asp Ala Pro Lys Ala Asn Gly Gln Val Gln Ser Glu Gln Val Ala Thr
    370                 375                 380

Pro Gly Val Gln Gln Thr His Ser Met Ala Gln Gln Ser Glu Thr Pro
385                 390                 395                 400

Gln Pro Val Ala Glu Glu Thr Glu Thr Ile Thr Glu Asn His Val Val
                405                 410                 415

Asp Ile Asp Glu Ser Thr Thr Phe Gln Lys Ser Gly Tyr Leu Tyr Gly
            420                 425                 430

Val Ser Glu Ser Asp Thr Ser Gly Tyr Thr Glu Arg Glu Lys Arg Ala
        435                 440                 445

Ile Arg Arg Asn His Val Arg Glu Ala Glu Ala Leu Val Asn Gln Tyr
    450                 455                 460

Val Glu Thr His Arg Tyr Gln Asp Arg Met Ala Ala Gln Gln Lys Val
465                 470                 475                 480

Asn Thr Leu Ser Lys Ala His Gln Lys Arg Phe Asn Lys Met Ile Asn
                485                 490                 495

Lys Ala Tyr Asn Gly Gln
            500


<210> SEQ ID NO 9
<211> LENGTH: 978
<212> TYPE: DNA
<213> ORGANISM: artificial sequence
<220> FEATURE:
<223> OTHER INFORMATION: S. pseudintermedius Gamma Hemolysin synthetic
      gene optimized for expression in E.coli

<400> SEQUENCE: 9

atgaagatta gcaaagttat taaggcggcg accgcgacca gcgtggcgct gatgctgttt      60

agcaacccgg tgtatgcggc gaaccagatt accccggtga gcgagaagaa agttgacgat     120

aagatcaccc tgtacaaaac caccgcgacc gcggacagcg ataagctgaa catcgaccaa     180

ctgctgacct tcgcgtttat taaggataaa agctacgaca aggataccct ggtgctgaaa     240

gcggcgggta acattaacag cggctataaa agcccgaacc cgaacgacta catctatagc     300

agcttctact ggggtgcgaa gtataacgtg agcattagcg cggaaagcaa aggcgcggtt     360

aacgtggttg actacgcgcc gaagaaccaa aacgaggaat tccaggtgca aaacaccctg     420

ggttatagct ttggtggtga catcagcatt agcaagggtc tgagcggtgg cctgaacggc     480

agcgagagct ttagcgaaac catcaactac aaacaggaga gctatcgtac caccatcgac     540
```

-continued

```
aagcacaccg ataacaaaac cattggttgg ggcgttgaag cgcacaagat catgaacgcg    600

ggttggggtc cgtatggtcg tgacagcttc cacgatctgt atggcaacga gctgtttctg    660

ggtggccgtc agagcaaact gaacgcgggt caaaacttcc tgccgaccag ccagatgccg    720

ctgctggcgc gtggcaactt caacccggaa tttctgagcg tgctgagcca caagccgaac    780

ggtgcgaaaa ccagcaagat taaagttacc taccaacgtg agatggatga atacaccaac    840

tattggaacg gttttcactg gatgggcacc aactacaaaa accagaacaa cgcgaccttc    900

accagctttt atgagatcga ctgggaccaa cataccgtga aactgattaa gacccatagc    960

gatgagaaaa acccgagc                                                  978
```

```
<210> SEQ ID NO 10
<211> LENGTH: 326
<212> TYPE: PRT
<213> ORGANISM: artificial sequence
<220> FEATURE:
<223> OTHER INFORMATION: S. pseudintermedius attenuated Gamma Hemolysin
      protein

<400> SEQUENCE: 10

Met Lys Ile Ser Lys Val Ile Lys Ala Ala Thr Ala Thr Ser Val Ala
1               5                   10                  15

Leu Met Leu Phe Ser Asn Pro Val Tyr Ala Ala Asn Gln Ile Thr Pro
            20                  25                  30

Val Ser Glu Lys Lys Val Asp Asp Lys Ile Thr Leu Tyr Lys Thr Thr
        35                  40                  45

Ala Thr Ala Asp Ser Asp Lys Leu Asn Ile Asp Gln Leu Leu Thr Phe
    50                  55                  60

Ala Phe Ile Lys Asp Lys Ser Tyr Asp Lys Asp Thr Leu Val Leu Lys
65                  70                  75                  80

Ala Ala Gly Asn Ile Asn Ser Gly Tyr Lys Ser Pro Asn Pro Asn Asp
                85                  90                  95

Tyr Ile Tyr Ser Ser Phe Tyr Trp Gly Ala Lys Tyr Asn Val Ser Ile
            100                 105                 110

Ser Ala Glu Ser Lys Gly Ala Val Asn Val Val Asp Tyr Ala Pro Lys
        115                 120                 125

Asn Gln Asn Glu Glu Phe Gln Val Gln Asn Thr Leu Gly Tyr Ser Phe
    130                 135                 140

Gly Gly Asp Ile Ser Ile Ser Lys Gly Leu Ser Gly Gly Leu Asn Gly
145                 150                 155                 160

Ser Glu Ser Phe Ser Glu Thr Ile Asn Tyr Lys Gln Glu Ser Tyr Arg
                165                 170                 175

Thr Thr Ile Asp Lys His Thr Asp Asn Lys Thr Ile Gly Trp Gly Val
            180                 185                 190

Glu Ala His Lys Ile Met Asn Ala Gly Trp Gly Pro Tyr Gly Arg Asp
        195                 200                 205

Ser Phe His Asp Leu Tyr Gly Asn Glu Leu Phe Leu Gly Gly Arg Gln
    210                 215                 220

Ser Lys Leu Asn Ala Gly Gln Asn Phe Leu Pro Thr Ser Gln Met Pro
225                 230                 235                 240

Leu Leu Ala Arg Gly Asn Phe Asn Pro Glu Phe Leu Ser Val Leu Ser
                245                 250                 255

His Lys Pro Asn Gly Ala Lys Thr Ser Lys Ile Lys Val Thr Tyr Gln
            260                 265                 270
```

-continued

```
Arg Glu Met Asp Glu Tyr Thr Asn Tyr Trp Asn Gly Phe His Trp Met
        275                 280                 285

Gly Thr Asn Tyr Lys Asn Gln Asn Asn Ala Thr Phe Thr Ser Phe Tyr
    290                 295                 300

Glu Ile Asp Trp Asp Gln His Thr Val Lys Leu Ile Lys Thr His Ser
305                 310                 315                 320

Asp Glu Lys Asn Pro Ser
                325


<210> SEQ ID NO 11
<211> LENGTH: 717
<212> TYPE: DNA
<213> ORGANISM: artificial sequence
<220> FEATURE:
<223> OTHER INFORMATION: S. pseudintermedius Exotoxin 15 synthetic gene
      optimized for expression in E.coli

<400> SEQUENCE: 11

ggatccaatg aaacagagca ccattctgaa agttagcctg gcagttggta ttctgaccac      60

cggtgtgggt attcatagcc aggcagcagc atttgcaagc gaagcacatg cacagaatgt     120

tcatagcgaa gcccagcagc tgaaagatta ttatagcaaa acctacttcg aatataacga     180

cgtgaccggt tatgtggaag ataacaataa actgagcgtt gtgacaccgc aagaaaccct     240

ggttagcatt agcctgctgg gtaaagatgc aagcacctat accgataaag aaaaagcata     300

tgatggtctg gccctgtttg ttgttccgga aggcaccgat cgtagcgcag aaaccaaaag     360

cattggtggt attaccaaac cgaatcagcg tagctattac gactatgtga aaaagccgaa     420

catcatcatc aacaaaaaat acggtgaact gaccagcagc atgagcacca atgatttttc     480

cattaacaaa gaagaagtga gcctgaaaga gctggatttt aaactgcgtc agaaactgat     540

taacgagtat ggcctgtatc agaatggcag cagtaatggt aaaatcgtga ttaaaatcgg     600

cgacaacgac aaagatatta tgccgctgga actgaacaaa aaactgcaag aacatgcaat     660

gagcgatacc gttgatgtga acaaaattca gcagattacc atcgacctgg cggccgc        717


<210> SEQ ID NO 12
<211> LENGTH: 236
<212> TYPE: PRT
<213> ORGANISM: artificial sequence
<220> FEATURE:
<223> OTHER INFORMATION: S. pseudintermedius attenuated Exotoxin 15
      Protein

<400> SEQUENCE: 12

Met Lys Gln Ser Thr Ile Leu Lys Val Ser Leu Ala Val Gly Ile Leu
1               5                   10                  15

Thr Thr Gly Val Gly Ile His Ser Gln Ala Ala Ala Phe Ala Ser Glu
            20                  25                  30

Ala His Ala Gln Asn Val His Ser Glu Ala Gln Gln Leu Lys Asp Tyr
        35                  40                  45

Tyr Ser Lys Thr Tyr Phe Glu Tyr Asn Asp Val Thr Gly Tyr Val Glu
    50                  55                  60

Asp Asn Asn Lys Leu Ser Val Val Thr Pro Gln Glu Thr Leu Val Ser
65                  70                  75                  80

Ile Ser Leu Leu Gly Lys Asp Ala Ser Thr Tyr Thr Asp Lys Glu Lys
                85                  90                  95

Ala Tyr Asp Gly Leu Ala Leu Phe Val Val Pro Glu Gly Thr Asp Arg
            100                 105                 110
```

-continued

```
Ser Ala Glu Thr Lys Ser Ile Gly Gly Ile Thr Lys Pro Asn Gln Arg
        115                 120                 125

Ser Tyr Tyr Asp Tyr Val Lys Lys Pro Asn Ile Ile Ile Asn Lys Lys
    130                 135                 140

Tyr Gly Glu Leu Thr Ser Ser Met Ser Thr Asn Asp Phe Ser Ile Asn
145                 150                 155                 160

Lys Glu Glu Val Ser Leu Lys Glu Leu Asp Phe Lys Leu Arg Gln Lys
                165                 170                 175

Leu Ile Asn Glu Tyr Gly Leu Tyr Gln Asn Gly Ser Ser Asn Gly Lys
            180                 185                 190

Ile Val Ile Lys Ile Gly Asp Asn Asp Lys Asp Ile Met Pro Leu Glu
        195                 200                 205

Leu Asn Lys Lys Leu Gln Glu His Ala Met Ser Asp Thr Val Asp Val
    210                 215                 220

Asn Lys Ile Gln Gln Ile Thr Ile Asp Leu Ala Ala
225                 230                 235
```

<210> SEQ ID NO 13
<211> LENGTH: 2023
<212> TYPE: DNA
<213> ORGANISM: artificial sequence
<220> FEATURE:
<223> OTHER INFORMATION: S. pseudintermedius Chimeric gene optimized for expression in E.coli

<400> SEQUENCE: 13

```
cactataggg cgaattggcg gaaggccgtc aaggccgcat gcatgaggat ccaccgcagc     60

acagattacc gcaggtattg cactgcatca gagcaatctg aataccgcag ttccgcagac    120

caaacatgaa gcaacctttg aagtgccgca gggtcgtaat acccagacca gcgcaaccgc    180

aaataaagaa caggcaaccg aaaccgttga tgcaccgaaa gcaaatggtc aggttcagag    240

cgaacaggtt gcaacaccgg gtgttcagca gacccatagc atggcacagc agagcgaaac    300

accgcagccg gttgcagaag aaaccgaaac aattaccggt agcatggtga aaaacaaact    360

gctggcagca accctgagca ttagcctggt tctgccgctg attaccccgt atagcgaaga    420

agcaaaagca gcaaatacca ttgaagaaat tggtgaaggt gcccagatta tcaaacgtac    480

cgaagatgtt agcagccgta aatggggtgt ttttcagaac atccagttcg attttgtgaa    540

agacccgaaa tataacaaag acgccctgat catcaaaatg cagggtttta tcaaaagccg    600

taccagcttt accgatgtga aaggtaaagg ttatgaaagc accaaacgta tgctgtggcc    660

gtttcagtat aacattgcac tgaaaaccaa tgatccgaat gtgagcctga tcaattatct    720

gcctgcaaac aaaattgaga gcatcgatgt tagtcagacc ctgggttata atgttggtgg    780

taattttcag agcgcaccgc tgttaggtgg taaaggtgca tttaactaca gcaagaaaat    840

cagctacacc cagaaaaact atattagcga agttgcccag cagaacagca aaaacattcg    900

ttgggaagtt aaagccaaca gctttaatac cgaaaatggc caggttagcg catatgatcg    960

tcacctgttt gttcgtagcc cgattggtcc gaatgcacgt gatttttttg ttccgaatga   1020

tgaactgcct ccgctgattc agagcggttt taatccggca tttattgcaa ccgttagcca   1080

cgaaaaagat aaaggtgata ccagcgaatt tgaaattgcc tatggtcgca atctggatat   1140

tacctatgca acctttttc cgcgtaccgg tatttttgca gaacgtcgtc ataatgcact   1200

gatgaatcgt aatctggtga ccaaatatga ggtgaactgg aaaacccatg agatcaaagt   1260

gaaaggccat aacgcagcaa aaaaagcaca gccggaagca accagcattg atcgtgcaag   1320
```

-continued

```
ccatgaaacc gcagcaacca cacataccat tctgcatacc aatgcaattg ccggtcgtat   1380

ggttgaagaa aaagatcgtg ttctgggtta tgatgcaatg accgcaggca atgcagaatt   1440

tgcctttggt tatgatcagc tgaaaaaact ggaaggcatg ctgaattttc cgattgtgag   1500

cagcaatgtg tacaaacacg aagatccgag ctttgccgaa gaaggtgata ataacgccga   1560

agccaaaaaa aacgccttta gtgaagttgt gaaactgccg aatctgagcg aagaacagcg   1620

taatggtttt attcagagcc tgaaagcagc accgagcacc agccaggatg tgctgaatga   1680

ggcaaaaaaa ctgaatgata gccaagaagg tagccagcct gcaccggatt atagtgatga   1740

aaaaaagaac gcgttttatg aaatccagtc attaaaagcc gcaccgtcag ttagcgcaaa   1800

tattctggtt gaagcgaaaa acatgaacgt taatcagacc ccgacacaac cggcaccgag   1860

ttttgatgaa gcaaaaaaga atgccttcta cgagattgtg aatcaggcca aacctgatta   1920

taacgaggca aagaaaaatg cattctatga aatactgcat ctgccgaatg cggccgctca   1980

tgcctgggcc tcatgggcct tccgctcact gcccgctttc cag                     2023
```

<210> SEQ ID NO 14
<211> LENGTH: 639
<212> TYPE: PRT
<213> ORGANISM: artificial sequence
<220> FEATURE:
<223> OTHER INFORMATION: S. pseudintermedius attenuated chimeric protein

<400> SEQUENCE: 14

```
Thr Ala Ala Gln Ile Thr Ala Gly Ile Ala Leu His Gln Ser Asn Leu
1               5                   10                  15

Asn Thr Ala Val Pro Gln Thr Lys His Glu Ala Thr Phe Glu Val Pro
            20                  25                  30

Gln Gly Arg Asn Thr Gln Thr Ser Ala Thr Ala Asn Lys Glu Gln Ala
        35                  40                  45

Thr Glu Thr Val Asp Ala Pro Lys Ala Asn Gly Gln Val Gln Ser Glu
    50                  55                  60

Gln Val Ala Thr Pro Gly Val Gln Gln Thr His Ser Met Ala Gln Gln
65                  70                  75                  80

Ser Glu Thr Pro Gln Pro Val Ala Glu Glu Thr Glu Thr Ile Thr Gly
                85                  90                  95

Ser Met Val Lys Asn Lys Leu Leu Ala Ala Thr Leu Ser Ile Ser Leu
            100                 105                 110

Val Leu Pro Leu Ile Thr Pro Tyr Ser Glu Glu Ala Lys Ala Ala Asn
        115                 120                 125

Thr Ile Glu Glu Ile Gly Glu Gly Ala Gln Ile Ile Lys Arg Thr Glu
    130                 135                 140

Asp Val Ser Ser Arg Lys Trp Gly Val Phe Gln Asn Ile Gln Phe Asp
145                 150                 155                 160

Phe Val Lys Asp Pro Lys Tyr Asn Lys Asp Ala Leu Ile Ile Lys Met
                165                 170                 175

Gln Gly Phe Ile Lys Ser Arg Thr Ser Phe Thr Asp Val Lys Gly Lys
            180                 185                 190

Gly Tyr Glu Ser Thr Lys Arg Met Leu Trp Pro Phe Gln Tyr Asn Ile
        195                 200                 205

Ala Leu Lys Thr Asn Asp Pro Asn Val Ser Leu Ile Asn Tyr Leu Pro
    210                 215                 220
```

-continued

```
Ala Asn Lys Ile Glu Ser Ile Asp Val Ser Gln Thr Leu Gly Tyr Asn
225                 230                 235                 240

Val Gly Gly Asn Phe Gln Ser Ala Pro Leu Leu Gly Gly Lys Gly Ala
                245                 250                 255

Phe Asn Tyr Ser Lys Lys Ile Ser Tyr Thr Gln Lys Asn Tyr Ile Ser
            260                 265                 270

Glu Val Ala Gln Gln Asn Ser Lys Asn Ile Arg Trp Glu Val Lys Ala
        275                 280                 285

Asn Ser Phe Asn Thr Glu Asn Gly Gln Val Ser Ala Tyr Asp Arg His
    290                 295                 300

Leu Phe Val Arg Ser Pro Ile Gly Pro Asn Ala Arg Asp Phe Phe Val
305                 310                 315                 320

Pro Asn Asp Glu Leu Pro Pro Leu Ile Gln Ser Gly Phe Asn Pro Ala
                325                 330                 335

Phe Ile Ala Thr Val Ser His Glu Lys Asp Lys Gly Asp Thr Ser Glu
            340                 345                 350

Phe Glu Ile Ala Tyr Gly Arg Asn Leu Asp Ile Thr Tyr Ala Thr Phe
        355                 360                 365

Phe Pro Arg Thr Gly Ile Phe Ala Glu Arg Arg His Asn Ala Leu Met
    370                 375                 380

Asn Arg Asn Leu Val Thr Lys Tyr Glu Val Asn Trp Lys Thr His Glu
385                 390                 395                 400

Ile Lys Val Lys Gly His Asn Ala Ala Lys Lys Ala Gln Pro Glu Ala
                405                 410                 415

Thr Ser Ile Asp Arg Ala Ser His Glu Thr Ala Ala Thr Thr His Thr
            420                 425                 430

Ile Leu His Thr Asn Ala Ile Ala Gly Arg Met Val Glu Glu Lys Asp
        435                 440                 445

Arg Val Leu Gly Tyr Asp Ala Met Thr Ala Gly Asn Ala Glu Phe Ala
    450                 455                 460

Phe Gly Tyr Asp Gln Leu Lys Lys Leu Glu Gly Met Leu Asn Phe Pro
465                 470                 475                 480

Ile Val Ser Ser Asn Val Tyr Lys His Glu Asp Pro Ser Phe Ala Glu
                485                 490                 495

Glu Gly Asp Asn Asn Ala Glu Ala Lys Lys Asn Ala Phe Ser Glu Val
            500                 505                 510

Val Lys Leu Pro Asn Leu Ser Glu Glu Gln Arg Asn Gly Phe Ile Gln
        515                 520                 525

Ser Leu Lys Ala Ala Pro Ser Thr Ser Gln Asp Val Leu Asn Glu Ala
    530                 535                 540

Lys Lys Leu Asn Asp Ser Gln Glu Gly Ser Gln Pro Ala Pro Asp Tyr
545                 550                 555                 560

Ser Asp Glu Lys Lys Asn Ala Phe Tyr Glu Ile Gln Ser Leu Lys Ala
                565                 570                 575

Ala Pro Ser Val Ser Ala Asn Ile Leu Val Glu Ala Lys Asn Met Asn
            580                 585                 590

Val Asn Gln Thr Pro Thr Gln Pro Ala Pro Ser Phe Asp Glu Ala Lys
        595                 600                 605

Lys Asn Ala Phe Tyr Glu Ile Val Asn Gln Ala Lys Pro Asp Tyr Asn
    610                 615                 620

Glu Ala Lys Lys Asn Ala Phe Tyr Glu Ile Leu His Leu Pro Asn
625                 630                 635
```